(12) United States Patent
Ross et al.

(10) Patent No.: US 11,819,488 B2
(45) Date of Patent: Nov. 21, 2023

(54) NANOSUSPENSIONS OF SALSALATE AND METHODS OF USING THE SAME

(71) Applicant: RHNanoPharma, Monmouth Beach, NJ (US)

(72) Inventors: Joel Ross, Monmouth Beach, NJ (US); Izhar Hasan, Monmouth Beach, NJ (US)

(73) Assignee: RHNanoPharma, Monmouth Beach, NJ (US)

(*) Notice: Subject to any disclaimer, the term of this patent is extended or adjusted under 35 U.S.C. 154(b) by 0 days.

(21) Appl. No.: 16/971,446

(22) PCT Filed: Feb. 22, 2019

(86) PCT No.: PCT/US2019/019194
§ 371 (c)(1),
(2) Date: Aug. 20, 2020

(87) PCT Pub. No.: WO2019/165240
PCT Pub. Date: Aug. 29, 2019

(65) Prior Publication Data
US 2020/0390737 A1 Dec. 17, 2020

Related U.S. Application Data

(60) Provisional application No. 62/634,575, filed on Feb. 23, 2018.

(51) Int. Cl.
*A61K 31/235* (2006.01)
*A61K 9/51* (2006.01)
*A61K 45/06* (2006.01)

(52) U.S. Cl.
CPC ............ *A61K 31/235* (2013.01); *A61K 9/51* (2013.01); *A61K 45/06* (2013.01)

(58) Field of Classification Search
CPC ......... A61K 31/235; A61K 9/51; A61K 45/06
See application file for complete search history.

(56) References Cited

U.S. PATENT DOCUMENTS

| | | | | |
|---|---|---|---|---|
| 8,821,938 B2* | 9/2014 | Straub | | A61P 35/00 514/952 |
| 8,852,644 B2* | 10/2014 | Baumstuemmler | | B01J 2/04 264/4.4 |
| 9,649,289 B1 | 5/2017 | Vaughn | | |
| 2007/0036831 A1 | 2/2007 | Baker | | |
| 2007/0172653 A1 | 7/2007 | Berkland et al. | | |
| 2011/0064813 A1 | 3/2011 | Vaughn | | |
| 2017/0368080 A1* | 12/2017 | Gan | | A61K 9/0053 |

FOREIGN PATENT DOCUMENTS

| WO | WO 1999/00113 A1 | 1/1999 |
|---|---|---|
| WO | WO 2016115520 | * 7/2016 |

OTHER PUBLICATIONS

Subramanian et al., Enhancement of anti-inflammatory property of aspirin in mice by a nano-emulsion preparation, Elsevier, International Immunopharmacology, (2008) 8, 1533-1539. (Year: 2008).*
International Search Report and Written Opinion issued in International Patent Application No. PCT/US2019/019194, dated May 8, 2019.
Extended Search Report issued in co-pending European Patent Application No. 19757829.7, dated Nov. 16, 2021.
Patel, et al., "Nanosuspension: An Approach to Enhance Solubility of Drugs," *J. Adv. Pharm. Tech. Res.*, vol. 2, No. 2, pp. 81-87 (2011).
Goldfine, et al., "The effects of salsalate on glycemic control in patients with type 2 diabetes: a randomized trial," *Ann Intern Med.*, vol. 152, pp. 346-357 (2010).
Anderson et al., "Salsalate, an Old, Inexpensive Drug with Potential New Indications: A Review of the Evidence from 3 Recent Studies," *American Health & Drug Benefits*, 7 (4), pp. 231-235 (2014).
Harrison et al., "Absorption, Biotransformation, and Pharmacokinetics of Salicylsalicylic Acid in Humans," *J. Clin. Pharmacol.*, vol. 21, pp. 401-404 (1981).
Harrison et al., "Effect of Food on Salsalate Absorption," Therapeutic Drug Monitoring, vol. 14, pp. 87-91 (1992).
Lagraouri et al., "Salsalate treatment following traumatic brain injury reduces inflammation and promotes a neuroprotective and neurogenic transcriptional response with concomitant functional recovery," Brain, Behavior, and Immunity, vol. 61: pp. 96-109 (2017).
Maude et al., "Managing Cytokine Release Syndrome Associated with Novel T Cell-Engaging Therapies," Cancer J., vol. 20, No. 2, pp. 119-122 (2014).
Lee Daniel W, et al., "Current Concepts in the diagnosis and management of cytokine release syndrome," Blood,. 128 (11): 1533 (Sep. 15, 2006).

* cited by examiner

*Primary Examiner* — Mina Haghighatian
(74) *Attorney, Agent, or Firm* — Duane Morris LLP

(57) ABSTRACT

The present invention is directed to nanosuspensions of salsalate and methods of making and using such compositions.

18 Claims, 56 Drawing Sheets

Figure 2
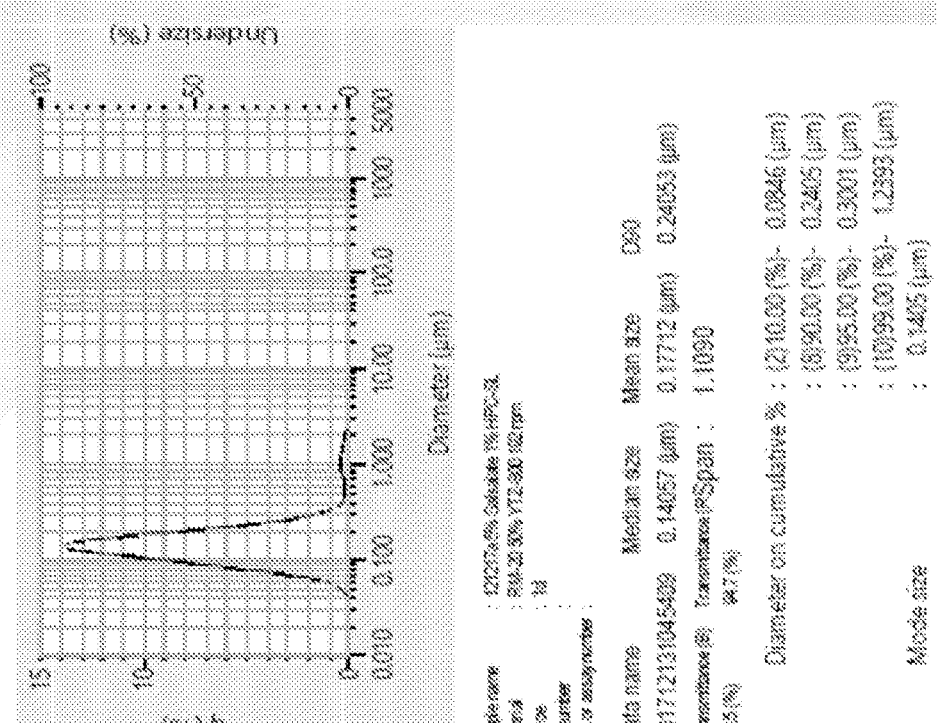
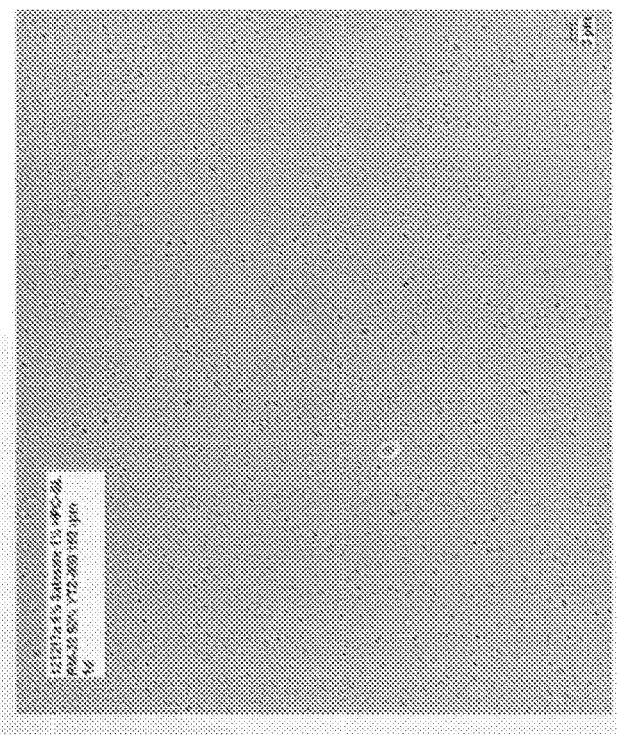

Figure 4
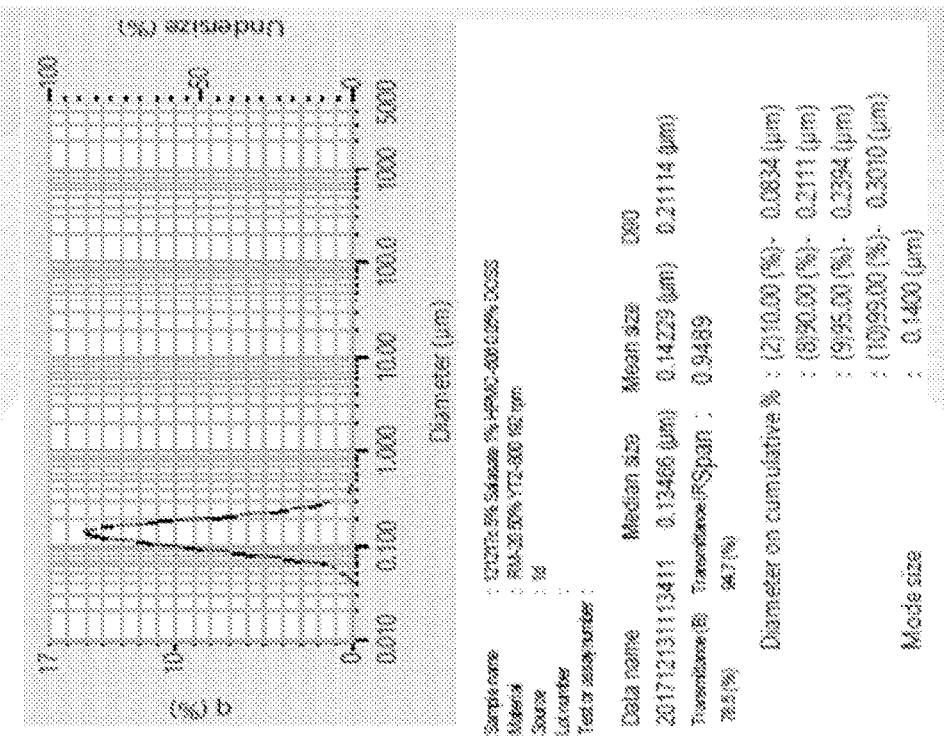
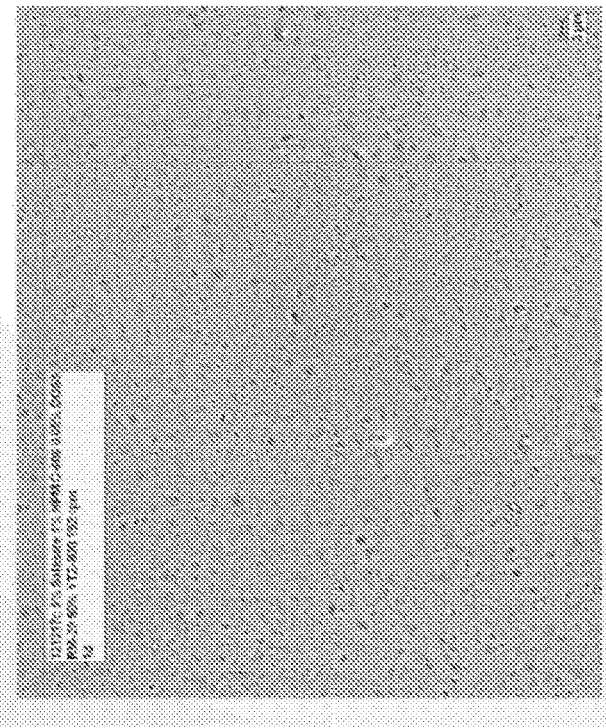

Figure 5
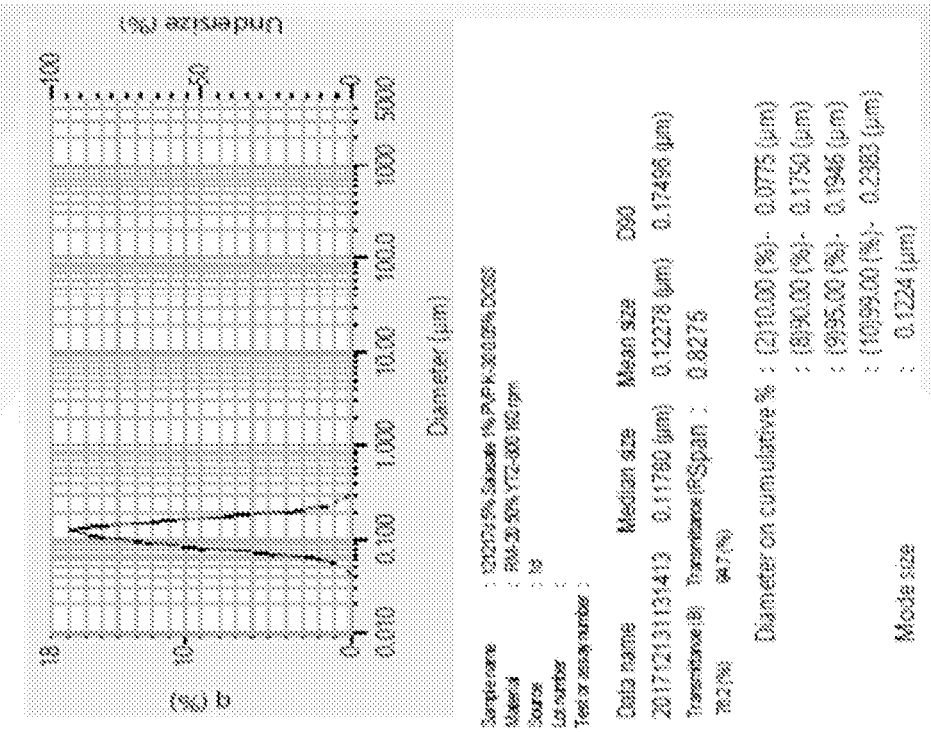
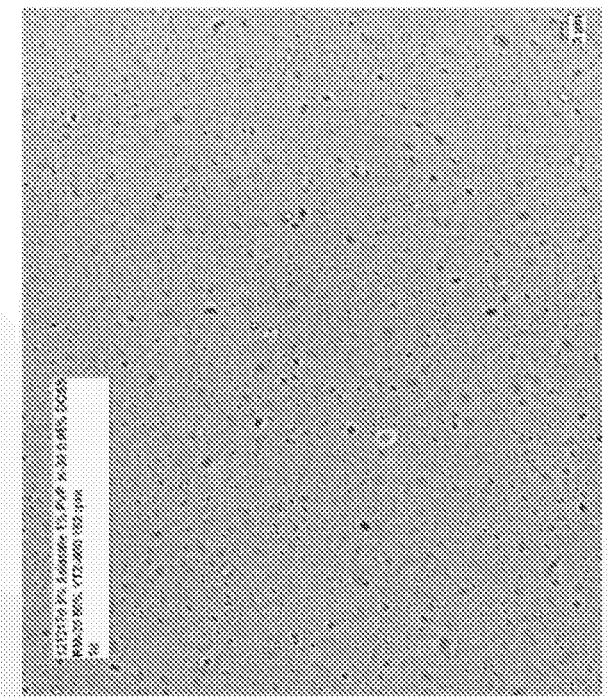

Figure 6
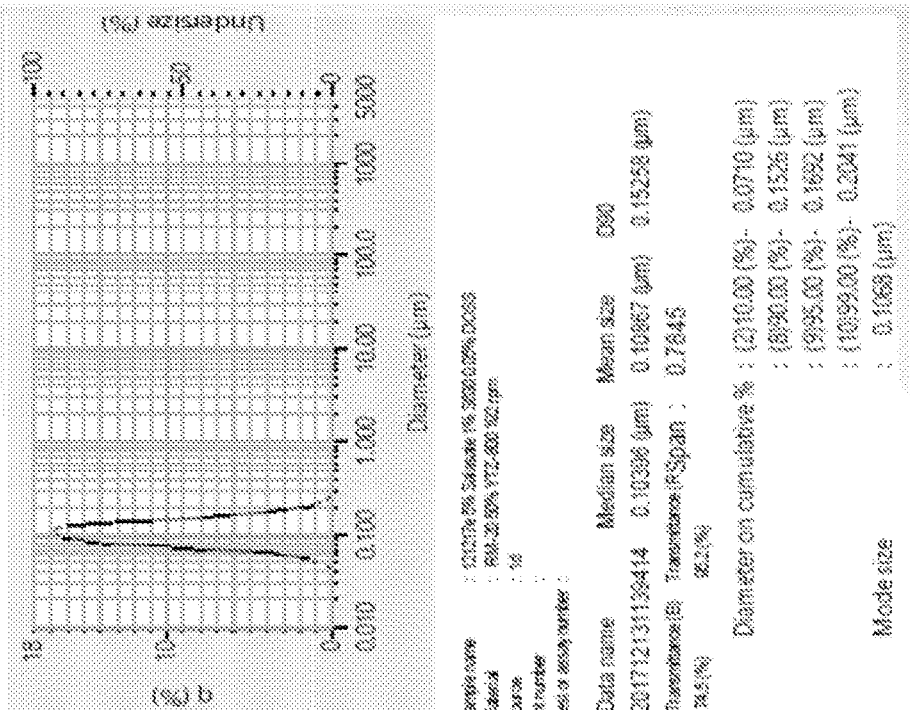
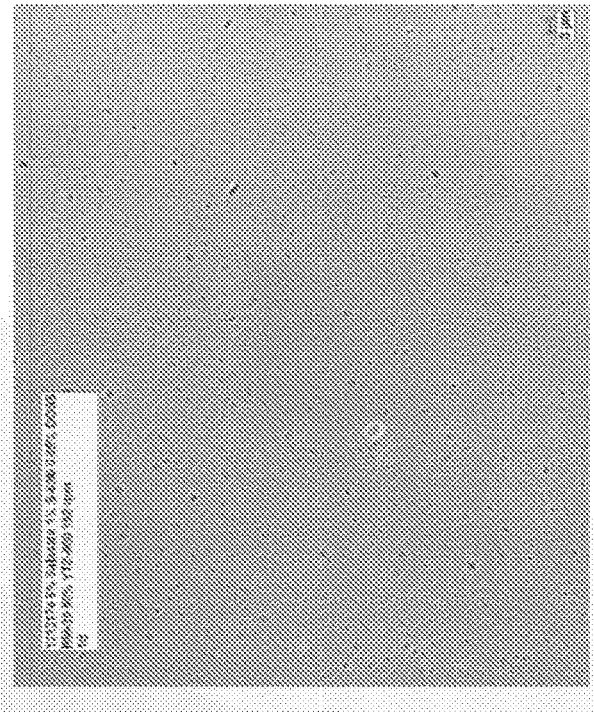

Figure 8
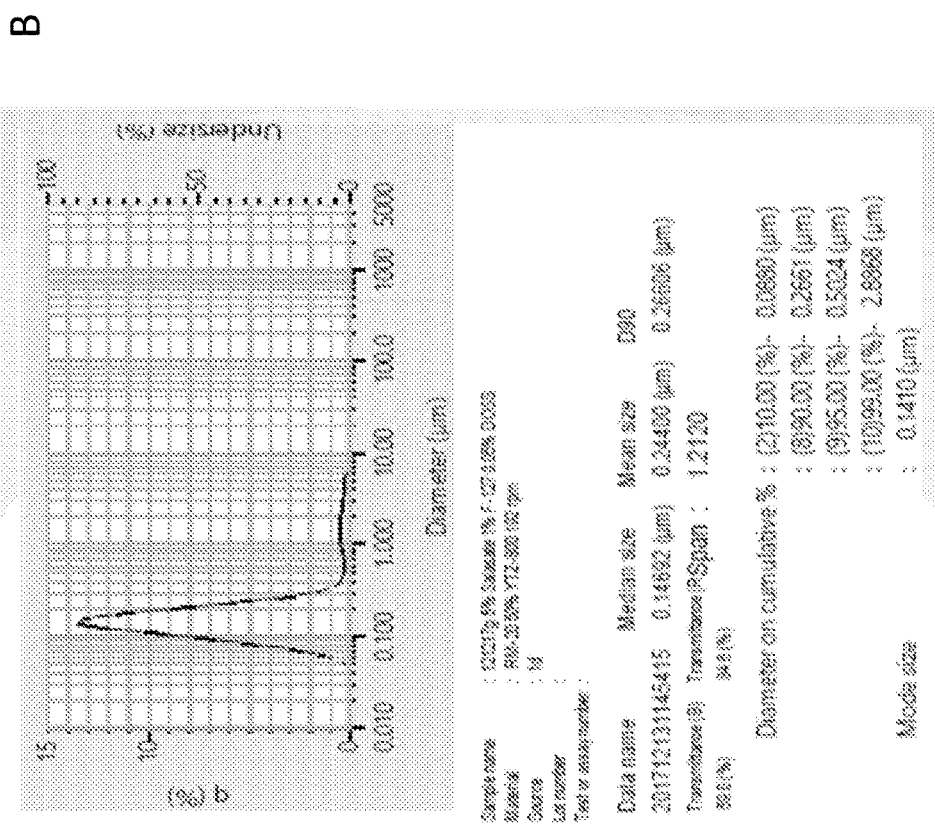
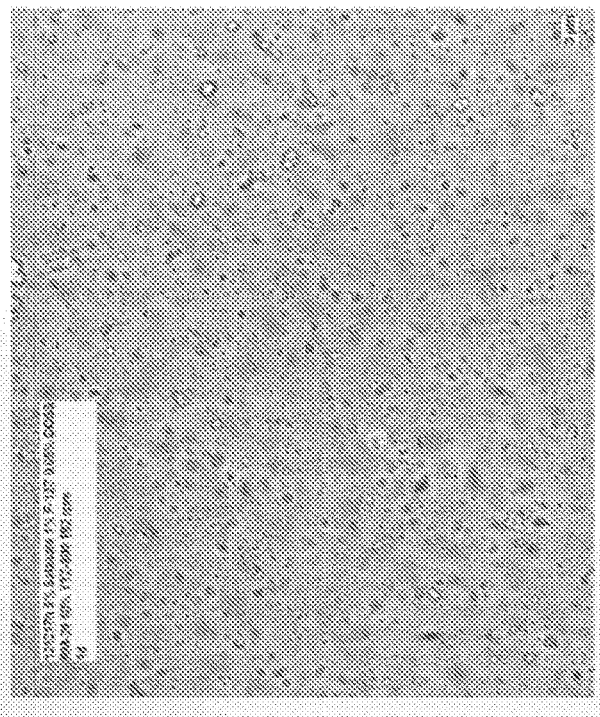

Figure 9
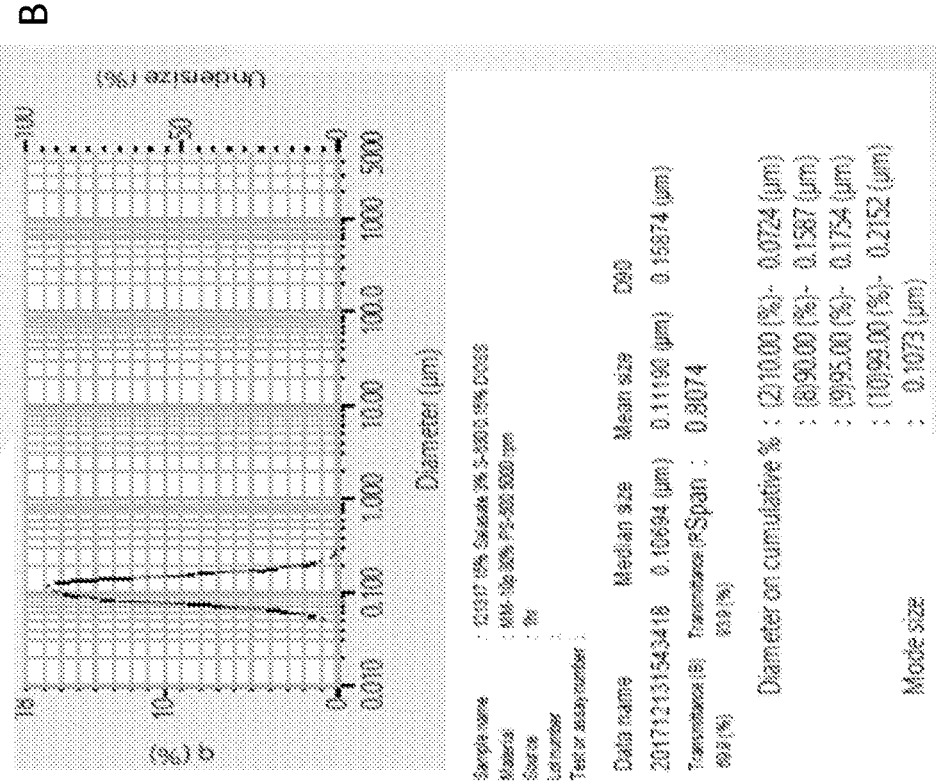
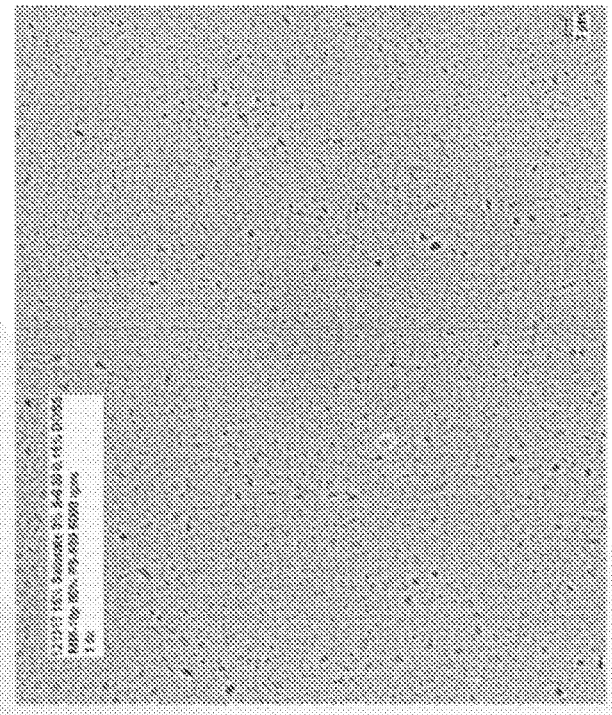

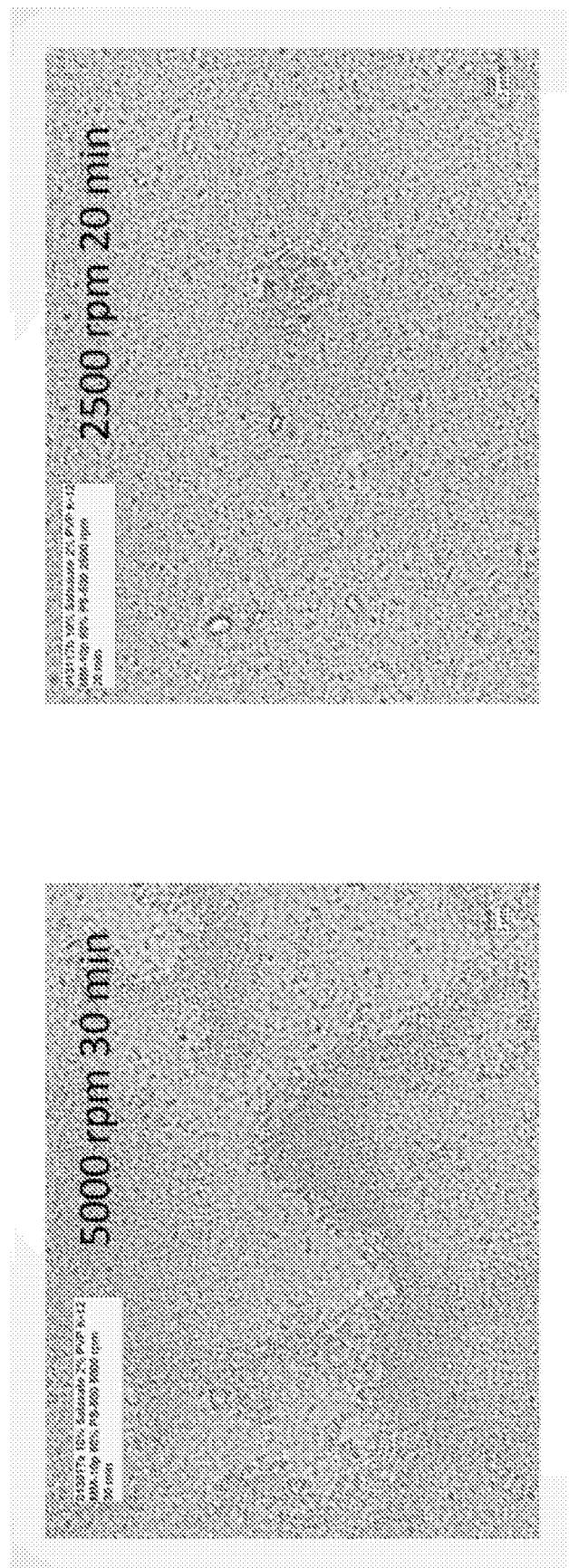
Figure 12A, B

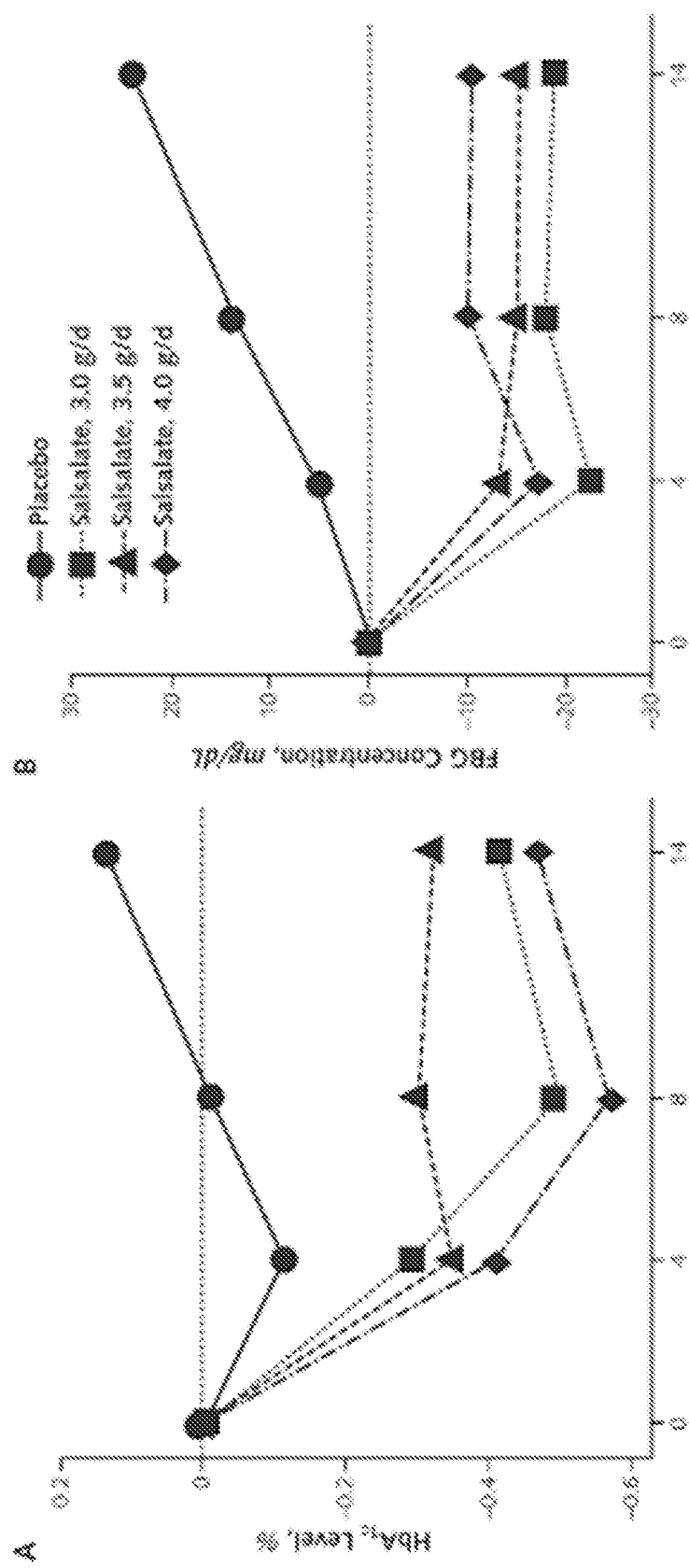
Figure 28A and B

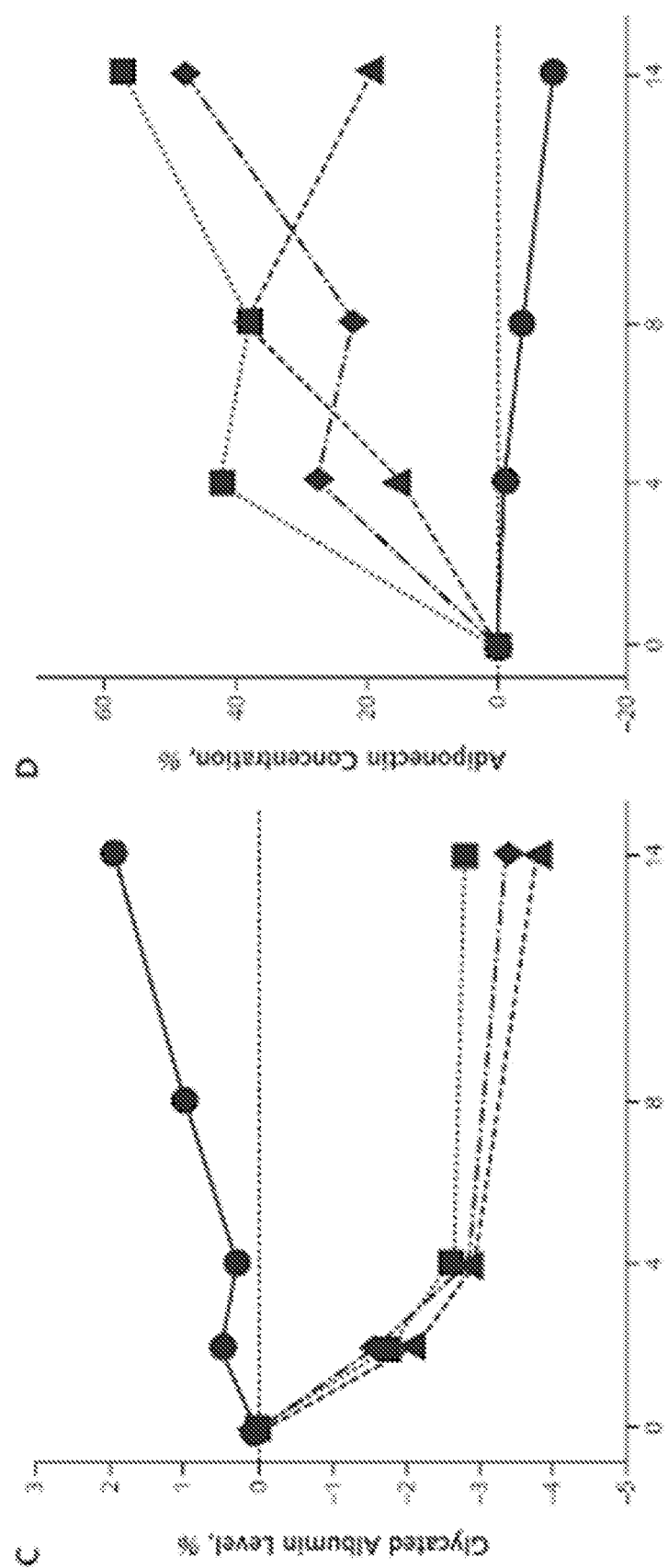
Figure 28C and D

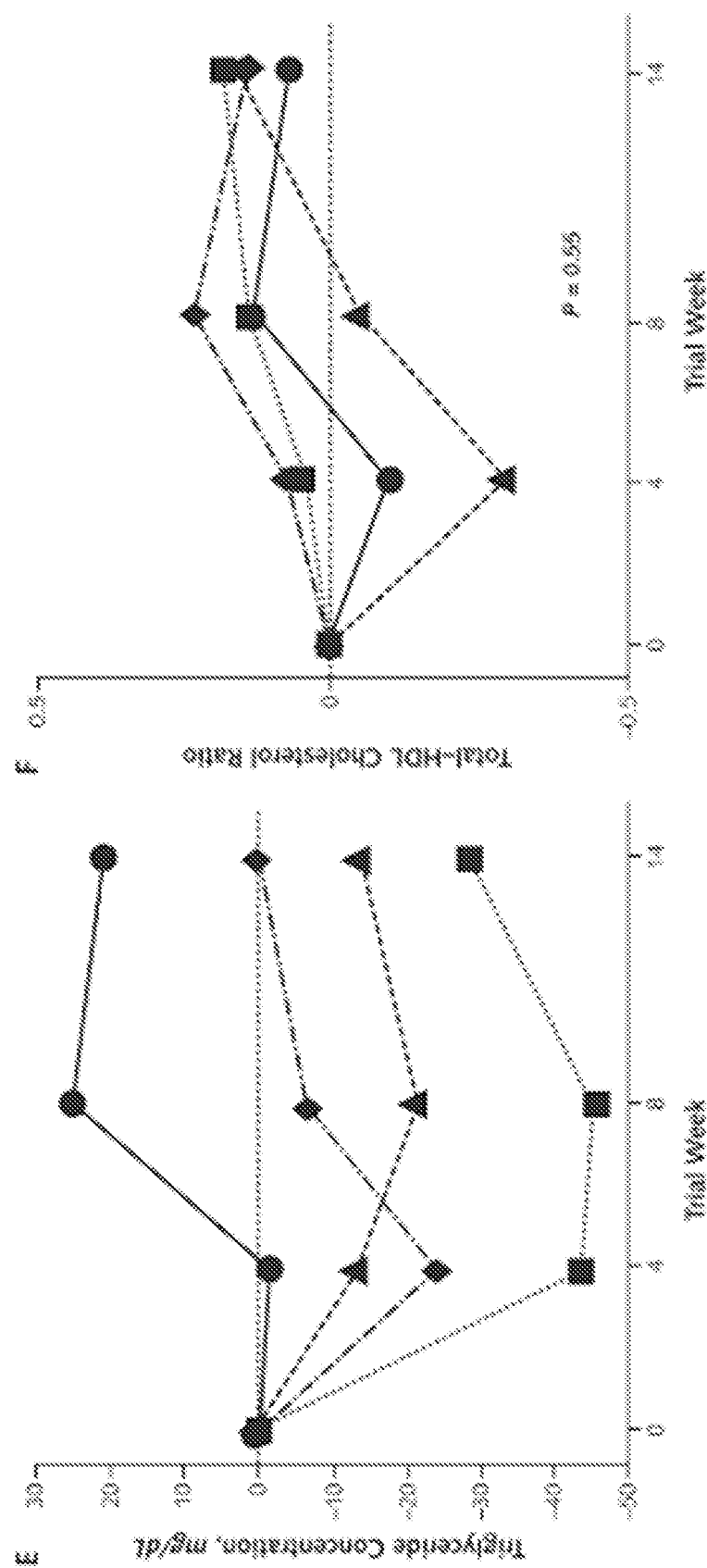
Figure 28E and F

NANOSUSPENSIONS OF SALSALATE AND METHODS OF USING THE SAME

CROSS-REFERENCE TO RELATED APPLICATIONS

This application is a U.S. National Stage Application of International Patent Application No. PCT/US2019/019194, filed Feb. 22, 2019, which claims priority from U.S. Provisional Patent Application No. 62/634,575, filed Feb. 23, 2018, the entire contents of these applications are incorporated herein by reference in their entirety.

FIELD OF THE INVENTION

The present invention is directed to nanosuspensions of salsalate and methods of making and using such compositions.

BACKGROUND

Salsalate (salicylic acid/SSA) (previously available as Disalcid® and various generics) is characterized as a non-acetylated salicylate. Salsalate possesses similar anti-inflammatory and analgesic properties to non-steroidal anti-inflammatory drugs (NSAIDs). The only known active metabolite of salsalate, salicylic acid (SA), has pleiotropic effects, binding to several targets to reduce inflammation and pain via reduction in expression and release of mediators of inflammation. One of the most widely studied sites of SA inhibition is IκB kinase. Binding of SA to IκB kinase results in preventing the release of Nuclear Factor Kappa B (NFKB). This results in a significant reduction of NFKB-mediated transcription of proinflammatory cytokines, such as the interleukins IL-1, IL-6 as well as tumor necrosis factor alpha (TNF-alpha).

There have been eight published clinical trials in which salsalate 3 grams/day was compared to placebo, aspirin, piroxicam, indomethacin, diclofenac or to no control group in patients with rheumatoid arthritis or osteoarthritis. The gastrointestinal safety of salsalate was compared to aspirin, naproxen and piroxicam in healthy subjects and patients with rheumatoid arthritis in five small studies using endoscopy. Those receiving salsalate were found to have a lower rate and severity of endoscopically determined erosions/lesions versus other active treatments.

Pharmacology/Pharmacokinetics: Salsalate is hydrolyzed to 2 molecules of salicylic acid following oral administration. Salsalate is relatively insoluble in gastric/acidic pH but is somewhat soluble in the more basic environment of the small intestine. Acetylsalicylic acid (aspirin) is more soluble in gastric acid than salsalate. Salsalate is chemically distinct from aspirin and in part possesses similar anti-inflammatory activity to aspirin. It is however less toxic to the gastrointestinal tract and does not interfere with platelet aggregation, and therefore bleeding from the gastrointestinal tract. The exact mechanism for its anti-inflammatory benefit and for its greater safety of compared to aspirin is unknown but may be explained in part by it being a pro-drug of salicylic acid and thought to be a weaker inhibitor of prostaglandins. Food has been shown to decrease the absorption rate of the salicylic acid derivative salsalate, meaning that a different drug absorption is obtained when a patient takes the drug with or without food.

FDA Approved Indication(s): Salsalate has not been approved by the FDA since it was available prior to the existence of the formal FDA approval process and as a result does not have any established FDA approved indications. Salsalate is legally prescribable in the US as an oral 500 and 750 mg tablet.

Potential Off-Label Uses: Salsalate has been used for decades for the management of pain and inflammation associated with rheumatoid arthritis and osteoarthritis and other inflammatory or painful conditions. Preliminary evidence shows that salsalate improves glycemic control in patients with prediabetes or those with newly diagnosed Type 2 diabetes. Typical dosage and administration of salsalate is 1500-3000 mg daily given orally in 2 or 3 divided doses.

Side effects: Overall, study withdrawal from the salsalate group for any reason ranged from 17-38% in studies of 3 weeks or more in duration. The most common adverse event leading to discontinuation of salsalate therapy was tinnitus or hearing loss which resolved upon discontinuation. Tinnitus is a commonly reported adverse event with salsalate. Other adverse events or side effects of salsalate can include cardiovascular risk, gastrointestinal bleeding, salicylate sensitivity and skin reactions.

Neither salsalate nor its only known active metabolite salicylic acid have any clinically significant effects on the Cyclooxygenase 1 (COX 1) enzyme, resulting in a very unique profile of gastric safety as well as being free of systemic bleeding concerns. These features distinguish salsalate from the NSAID class of anti-inflammatory/analgesics which have clinically significant gastrointestinal toxicities, cardiovascular risks, and increased risks of systemic bleeding.

There is a need for a safer and more effective therapeutic analgesic and anti-inflammatory agent. This disclosure satisfies these needs.

SUMMARY

In one aspect, provided herein are nanosuspensions comprising salsalate or a pharmaceutical salt thereof, and at least one surfactant. In an exemplary embodiment, encompassed is a salsalate nanosuspension comprising (a) an aqueous dispersion of salsalate or a salt thereof, wherein the salsalate has an effective average particle size of less than about 1 micron; and (b) at least one surfactant. In other embodiments, the salsalate present in the nanosuspension has an effective average particle size selected from the group consisting of less than about 900 nm, less than about 800 nm, less than about 700 nm, less than about 600 nm, less than about 500 nm, less than about 400 nm, less than about 300 nm, less than about 275 nm, less than about 250 nm, less than about 225 nm, less than about 200 nm, less than about 175 nm, less than about 150 nm, less than about 125 nm, less than about 100 nm, less than about 75 nm, and less than about 50 nm.

In another aspect, provided herein are pharmaceutical compositions comprising salsalate or a pharmaceutical salt thereof, and at least one surfactant, and optionally at least one pharmaceutically acceptable carrier, as well as any desired excipients.

The salsalate nanosuspension can be formulated for administration selected from the group consisting of oral, pulmonary, rectal, opthalmic, colonic, parenteral, intravenous, intracisternal, intravaginal, intraperitoneal, local, buccal, nasal, and topical administration. Further, the salsalate nanosuspension can be formulated into a dosage form selected from the group consisting of liquid dispersions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

In another embodiment, the salsalate nanosuspension can comprise (a) salsalate an amount of about 99.5% to about 0.001%, and (b) at least one surfactant in an amount of about 0.5% to about 99.999%.

The salsalate nanosuspension can comprise at least one surfactant, which includes least two surfactants. For example, the salsalate nanosuspension can comprise a surfactant which is an anionic surfactant, a cationic surfactant, an ionic surfactant, a nonionic surfactant, or a zwitterionic surfactant. In other embodiments, the at least one surfactant can be HPC-SL, HPMC, polysorbates such as polysorbate 20 and polysorbate 80, poloxamers such as poloxamer 407 and poloxamer 188, PVP, DOSS, random copolymers of vinylpyrrolidone and vinyl acetate such as Plasdone S-630, lecithin, and any combination thereof.

In yet another embodiment, the salsalate nanosuspension can further comprise at least one non-salsalate active agent.

In one embodiment, the salsalate nanosuspension upon oral administration can have (a) a $T_{max}$ which is less than that of a conventional non-nanosuspension or microcrystalline composition of salsalate, administered at the same dosage; (b) a $C_{max}$ which is greater than that of a conventional non-nanosuspension or microcrystalline composition of salsalate, administered at the same dosage; and/or (c) an AUC which is greater than that of a conventional non-nanosuspension or microcrystalline composition of salsalate, administered at the same dosage. In another embodiment, in comparative pharmacokinetic testing with a conventional non-nanosuspension or microcrystalline composition of salsalate, administered at the same dosage, the salsalate nanosuspension exhibits (a) a $T_{max}$ selected from the group consisting of less than about 100%, less than about 90%, less than about 80%, less than about 70%, less than about 60%, less than about 50%, less than about 40%, less than about 30%, less than about 25%, less than about 20%, less than about 15%, and less than about 10% of the $T_{max}$ exhibited by the conventional non-nanosuspension or microcrystalline composition of salsalate; (b) a $C_{max}$ selected from the group consisting of greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, and greater than about 150% than the $C_{max}$ exhibited by the conventional non-nanosuspension or microcrystalline composition of salsalate; and/or (c) an AUC selected from the group consisting of greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, and greater than about 150% than the AUC exhibited by the conventional non-nanosuspension or microcrystalline composition of salsalate.

In one embodiment, following administration the salsalate nanosuspension has a $T_{max}$ selected from the group consisting of less than about 10 hours, less than about 9 hours, less than about 8 hours, less than about 7 hours, less than about 6 hours, less than about 5.5 hours, less than about 5 hours, less than about 4.5 hours, less than about 4 hours, less than about 3.5 hours, less than about 3 hours, less than about 2.5 hours, less than about 2.25 hours, less than about 2 hours, less than about 1.75 hours, less than about 1.5 hours, less than about 1.25 hours, less than about 1.0 hours, less than about 50 minutes, less than about 40 minutes, less than about 30 minutes, less than about 25 minutes, less than about 20 minutes, less than about 15 minutes, and less than about 10 minutes. In yet another embodiment, following administration the salsalate nanosuspension has a $T_{max}$ between about 10 minutes to about 10 hours.

Also provided herein are methods of making a salsalate nanosuspension comprising salsalate or a pharmaceutical salt thereof, and at least one surfactant. Such methods comprise contacting salsalate with at least one surfactant for a time and under conditions sufficient to provide an salsalate/surfactant nanosuspension, wherein the salsalate has an effective average particle size of less than about 1 micron. In some embodiments, the salsalate or salt thereof is contacted with the surfactant either before, during, or after particle size reduction of the salsalate. In one embodiment, the contacting comprises grinding or homogenization.

The present disclosure is further directed to methods of treatment comprising administering to a subject in need a therapeutically effective amount of a salsalate nanosuspension according to the embodiments described herein.

The methods of treatment can comprise any pharmaceutically acceptable method of administration. In exemplary embodiments, the methods of administration can comprise oral, parenteral, or intravenous administration. In another embodiment, administration can be once or twice daily. Further, in another exemplary embodiment, the salsalate nanosuspension comprises about 1000 mg to about 2000 mg of nanosalsalate suspension administered orally and/or parenterally. In yet another embodiment, following administration the salsalate nanosuspension maintains a plasma concentration of salsalate ranging from about 120 to about 200 μg/ml over a period of at least about 12 to about 24 hours. The subject to be treated can have, for example, a non-central nervous system disorder or a central nervous system disorder.

In yet another embodiment, the subject has an inflammatory disease. For example, the inflammatory disease is selected from the group consisting of cytokine release syndrome/cytokine storm, prediabetes, diabetes, arthritis, inflammatory bowel disease (IBD), and diseases associated with inflammation in the brain. Additionally, the method can be used to treat an arthritis related disease or condition. Further, the arthritis related disease or condition is selected from the group consisting of adult-onset Still's disease, ankylosing spondylitis, back pain, Behçet's disease, bursitis, calcium pyrophosphate deposition disease, carpal tunnel syndrome, chondromalacia patella, chronic fatigue syndrome, complex regional pain syndrome, cryopyrin-associated periodic syndromes, degenerative disc disease, developmental-dysplasia of hip, Ehlers-Danlos, familial Mediterranean fever, fibromyalgia, fifth disease, giant cell arteritis, gout, hemochromatosis, infectious arthritis, inflammatory arthritis, inflammatory bowel disease, juvenile arthritis, juvenile dermatomyositis, juvenile idiopathic arthritis, juvenile scleroderma, Kawasaki disease, lupus, Lyme disease, mixed connective tissue disease, myositis, osteoarthritis, osteoporosis, Pagets, palindromic rheumatism, patellofemoral pain syndrome, pediatric rheumatic diseases, polymyalgia rheumatica, pseudogout, psoriatic arthritis, Raynaud's phenomenon, reactive arthritis, reflex sympathetic dystrophy, Reiter's sydrome, rheumatic fever, rheumatism, rheumatoid arthritis, scleroderma, Sjögren's disease, spinal stenosis, spondyloarthritis, systemic juvenile idiopathic arthritis, systemic lupus erythematosus, systemic sclerosis, temporal arteritis, tendinitis, vasculitis, and Wegener's granulomatosis.

In another embodiment, the diabetes is type II diabetes. In yet another embodiment, diseases associated with inflammation in the brain include traumatic brain injury and non-Alzheimer's tauopathies. Further, the non-Alzheimer's tauopathies can be progressive supranuclear palsy and/or chronic traumatic encephalopathy. In addition, the IBD can be Crohn's disease or ulcerative colitis.

In yet another embodiment, the method of treatment is directed to inhibiting the production of inflammatory cytokines and/or chemokines. For example, the cytokine release syndrome/cytokine storm can be the result of an infection, a disease, an adoptive T-cell therapy, or an antibody drug, graft-versus-host disease (GVHD), acute respiratory distress syndrome (ARDS), sepsis, Ebola, avian influenza, smallpox, and systemic inflammatory response syndrome (SIRS). In another embodiment, wherein the cytokine release syndrome/cytokine storm is the result of a CAR-T therapy. Further, the cytokine release syndrome/cytokine storm can be the result of an antibody therapy. Moreover, the antibody therapy can be CD20 antibody rituximab or CD19 antibody tisagenlecleucel.

The salsalate nanodispersions of the disclosure are also useful in treating an eye disease or related condition. For example, the eye disease or related condition can be optic nerve disorders, retinal disorders, macular degeneration, diabetes-related conditions, dry eye syndrome, allergies, or ocular infections. In this method of treatment, the salsalate nanodispersion can be administered topically to the eye of the subject, but any pharmaceutically acceptable delivery method can be utilized.

The salsalate nanodispersions of the disclosure are also useful in treating subjects with hemophilia.

The salsalate nanodispersions of the disclosure are also useful in treating subjects with coronary artery disease (CAD).

Finally, the subject in the methods of treatment can be mammal, including a human.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIGS. 1A and B. Analysis an OM of an aqueous suspension of salsalate starting active pharmaceutical ingredient (API). FIG. 1A shows an oil immersion photomicroscopy (OM) of 5% unmilled salsalate API in water and FIG. 1B shows the results of a particle size analysis of the dispersion using a Horiba light scattering particle size analyzer.

FIGS. 2A and B. FIG. 2A shows an OM of an aqueous dispersion of 5% salsalate and 1% HPC-SL following roller milling with a Roller-Mill RM20 (ZOZ GmbH) with YTZ-800 grinding media (Tosoh Corp.). FIG. 2B shows the results of a particle size analysis using a Horiba light scattering particle size analyzer.

FIG. 3A shows an OM of an aqueous dispersion of 5% salsalate, 1% HPC-SL, and 0.05% DOSS (docusate sodium) following roller milling with a Roller-Mill RM20 with YTZ-800 grinding media.

FIGS. 4A and B. FIG. 4A shows an OM of an aqueous dispersion of 5% salsalate, 1% HPMC, and 0.05% DOSS (docusate sodium) following roller milling with a Roller-Mill RM20 with YTZ-800 grinding media. FIG. 4B shows the results of a particle size analysis using a Horiba light scattering particle size analyzer.

FIGS. 5A and B. FIG. 5A shows an OM of an aqueous dispersion of 5% salsalate, 1% PVP K-30, and 0.05% DOSS (docusate sodium) following roller milling with a Roller-Mill RM20 with YTZ-800 grinding media. FIG. 5B shows the results of a particle size analysis using a Horiba light scattering particle size analyzer.

FIGS. 6A and B. FIG. 6A shows an OM of an aqueous dispersion of 5% salsalate, 1% Plasdone S-630, and 0.05% DOSS (docusate sodium) following roller milling with a Roller-Mill RM20 with YTZ-800 grinding media. FIG. 6B shows the results of a particle size analysis using a Horiba light scattering particle size analyzer.

FIG. 7A shows an OM of an aqueous dispersion of 5% salsalate and 0.5% Tween 80 following roller milling with a Roller-Mill RM20 with YTZ-800 grinding media.

FIGS. 8A and B. FIG. 8A shows an OM of an aqueous dispersion of 5% salsalate, 1% Pluronic F-127, and 0.05% DOSS (docusate sodium) following roller milling with a Roller-Mill RM20 with YTZ-800 grinding media. FIG. 8B shows the results of a particle size analysis using a Horiba light scattering particle size analyzer.

FIGS. 9A and B. FIG. 9A shows an OM of an aqueous dispersion of 15% salsalate, 3% Plasdone S-630, and 0.15% DOSS following high speed media milling. FIG. 9B shows the results of a particle size analysis using a Horiba light scattering particle size analyzer.

FIGS. 10A, B, C.

FIGS. 11A, B, C, D.

FIGS. 12A, B, C. FIG. 12A shows an OM of an aqueous dispersion of 10% salsalate and 2% PVP K-12 following high speed milling in a MM-10p High Speed Media Mill, with 80% PS-500 media, at 5000 rpm, for 30 min; FIG. 12B shows an OM of an aqueous dispersion of 10% salsalate and 2% PVP K-12 following high speed milling in a MM-10p High Speed Media Mill, with 80% PS-500 media, at 2500 rpm, for 20 min.

FIG. 13A shows an OM of an aqueous dispersion of 10% salsalate and 2% PVP K-12 following high speed media milling.

FIG. 15A shows an OM of an aqueous dispersion of 10% salsalate, 1% Tween 20, and 1% lecithin following high speed media milling.

FIG. 16A shows an OM of an aqueous dispersion of 10% salsalate, 1% Tween 20, and 1% lecithin following high speed media milling.

FIG. 17A shows an OM of an aqueous dispersion of 10% salsalate, 1% Tween 20, and 1% lecithin following high speed media milling.

FIG. 18A shows an OM of an aqueous dispersion of 10% salsalate, 1% Tween 80, and 1% lecithin following high speed media milling.

FIG. 18A shows an OM of an aqueous dispersion of 10% salsalate, 1% Tween 80, and 1% lecithin following high speed media milling.

FIG. 20 shows an OM of an aqueous dispersion of 10% salsalate and 1% Tween 80 following high speed media milling.

FIG. 21A shows an OM of an aqueous dispersion of 10% salsalate and 1% Tween 80, following high speed media milling.

FIG. 22A shows an OM of an aqueous dispersion of 10% salsalate and 1% Tween 80, following high speed media milling.

FIG. 23A shows an OM of an aqueous dispersion of 10% salsalate and 1% Tween 80, following high speed media milling.

FIG. 25A: A first human subject administered a 750 mg po of 4.28 ml of an oral salsalate nanosuspension. FIG. 25B: A second human administered a 750 mg po of 4.28 ml of an oral salsalate nanosuspension. FIG. 25C: A human subject administered one tablet of salsalate distributed and/or manufactured by ECI Pharma (Florida, USA) of also 750 mg dose.

FIGS. 28A-F. Provides data regarding various oral doses of twice daily non nano (regular/standard formulation microcrystalline) salsalate at three different daily doses of 3.0, 3.5 and 4.0 grams over a 4 week period in patients with type two diabetes mellitus. FIG. 28A=Trends in HbAlc level over time. FIG. 28B=Trends in FBG concentration over time. FIG. 28C=Trends in glycated albumin level over time. FIG. 28D=Trends in adiponectin concentration over time. FIG. 28E=triglyceride concentration over time. FIG. 28F=total HDL-cholesterol ratio over time.

FIG. 33A shows an oil immersion photomicrograph (OM) of an aqueous dispersion of 10% salsalate and 1% Tween 80, following high speed milling with MM-10p High Speed Media Mill, 80% PS-500 media, 5000 rpm, depicted 1 hr before centrifugation.

FIG. 34A shows a OM of an aqueous dispersion of 10% salsalate and 1% Tween 80, following high speed milling with MM-10p High Speed Media Mill, 80% PS-500 media, 5000 rpm, 1 hr spin.

FIG. 35A shows a OM of an aqueous dispersion of 10% salsalate and 1% Tween 80, following high speed milling with MM-10p High Speed Media Mill, 80% PS-500 media, 5000 rpm, 1 hr spin, and one day at 5° C.

FIG. 36A shows a OM of an aqueous dispersion of 10% salsalate and 1% Tween 80, following high speed milling with MM-10p High Speed Media Mill, 80% PS-500 media, 5000 rpm, 1 hr spin, and three days at 5° C.

FIG. 37A shows a OM of an aqueous dispersion of 10% salsalate and 1% Tween 80, following high speed milling with MM-10p High Speed Media Mill, 80% PS-500 media, 5000 rpm, 1 hr spin, and five days at 5° C.

DETAILED DESCRIPTION

I. Overview

Figure 1:
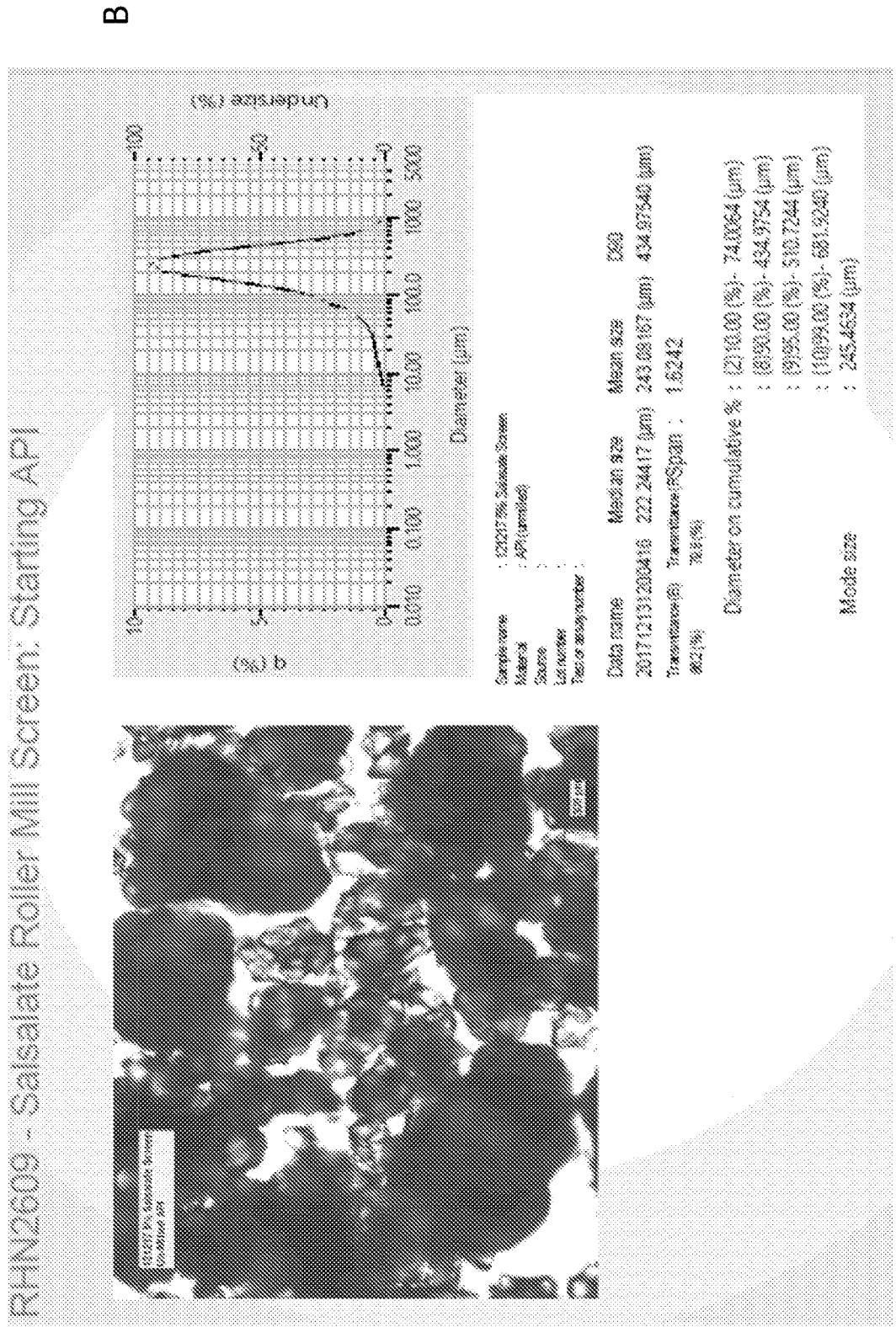

The present disclosure is directed to the surprising and unexpected discovery that stable nanosuspensions of salsalate can be made. The salsalate nanosuspensions provide ameliorative/beneficial effects by reducing the production of mediators of inflammation and as such reduce the severity of inflammatory conditions.

The nanosuspensions of the invention comprise salsalate or a salt thereof and at least one surfactant, preferably adsorbed to the surface of the salsalate drug particles. Further, the salsalate drug particles have an effective average particle size of less than about 1 micron. In an exemplary embodiment, an oral formulation of a salsalate nanosuspension comprises a combination of DOSS and Plasdone S-630 as surfactants in concentrations that are GRAS (Generally Recognized As Safe) by FDA standards. In another exemplary embodiment, an intravenous salsalate nanosuspension comprises as a surfactant PVP, Tween 20, Tween 80, Lecithin or any combination thereof, in concentrations that are GRAS (Generally Recognized As Safe) by FDA standards. Other useful surfactant and surfactant combinations are described herein.

Not all combinations of salsalate and surfactants were found to produce stable nanosuspensions. See e.g., Examples 1 and 2. It is preferable to utilize surfactants recognized by the FDA or EMEA as GRAS (generally recognized as safe). GRAS surfactants suitable for oral administration are not generally the same as those suitable for injectable administration.

It was surprisingly found that nanosuspensions of salsalate (1) produce significantly less gastrointestinal irritation as compared to conventional crystalline salsalate as well as NSAIDs; (2) require smaller doses to obtain the same or better pharmacological effect as compared to conventional microcrystalline forms of salsalate; (3) produce improved pharmacokinetic profiles as compared to conventional microcrystalline forms of salsalate, including increased $C_{max}$ and AUC, and/or decreased $T_{max}$; (4) reduced side effects, such as eliminating or lessening tinnitus or hearing, cardiovascular risk, gastrointestinal bleeding, salicylate sensitivity and skin reactions; (5) minimizing or eliminating the need for multiple daily salsalate doses to obtain a therapeutic effect, thereby increasing patient compliance (multiple doses a day correlate with decreased patient compliance); (6) decreased fed/fasted absorption variability; (7) faster onset of action; (8) increased bioavailability as compared to conventional microcrystalline forms of salsalate; (9) provide a higher mass per volume loading as compared to conventional microcrystalline forms of salsalate, a crucial feature when high dosing and/or low administration volume is required; and (10) other benefits described herein.

Reduction in the production of mediators of inflammation by the mechanism of inhibition of the enzyme called IKKb (a kinase that phosphorylates the protein called KK responsible for keeping nuclear factor Kappa B held tightly bound in the cytoplams) represents a novel approach not shared by any of the current treatment modalities. Nuclear Factor Kappa B (NFKb) has been shown on a molecular level to be held "in check" by salsalate only active metabolite, salicylic acid. Additionally salicylic acid has effects on reducing expression and production of mediators of inflammation via alternative pathways such as inhibiting two pro-inflammatory enzymes called Human Growth Box Mobility I (HMGB1) and Glyceraldehyde 3-phosphate dehydrogenase (GAPDH). Such mediators include but are not limited to interleukin 1, interleukin 6, tumor necrosis factor alpha, interleukin 10, IFN-alpha as well as markers of inflammation such as C-reactive protein and serum ferritin.

Figure 29:
FIG. 29. Shows the chemical structure of aspirin (acetylsalicyclic acid) vs salsalate (salicylsalicylic acid/salsalate). The lack of an "acetyl" group of salsalate accounts for the better GI, hematological and renal safety of the compound as compared to aspirin.

Salsalate is a dimer of salicylic acid or derivative of salicylic acid, which upon hydrolysis yields two molecules of salicylic acid. Salsalate has been found to have significantly less side effects than aspirin, as well as a safer side effect profile compared to the class of anti-inflammatory agents called non-steroidal anti-inflammatory drugs or NSAIDs, including prescription and over the counter types of NSAIDs. Brand names for salsalate include Mono-Gesic, Salflex, Disalcid, and Salsitab. Salsalate is not an NSAID as it does not bind to what is referred to as the cyclooxygenase enzymes known as COX-I and COX-2. FIG. 29 shows the structure of acetylsalicyclic acid (aspirin) and salicyclsalicylic acid (salsalate). The lack of an acetyl group for salsalate is believed to account for the better GI, hematological, and renal safety as compared to aspirin.

The slightly lower levels of salicylic acid (in terms of salicylic acid equivalents) in plasma after salsalate administration compared to that found after aspirin administration may reflect direct biotransformation of some of the salsalate to salsalate conjugates (e.g., glucuronide conjugates), without hydrolysis to salicylic acid.

Based on relative AUC values for salicylic acid, salsalate is hydrolyzed in the body to give approximately 84% of the salicylic acid obtained from an equivalent dose (in terms of salicylic acid equivalents) of aspirin (acetylsalicylic acid). It has been also found that salsalate causes significantly less gastrointestinal bleeding and gastric erosions at anti-inflammatory doses than does aspirin (Harrison et al., *J Clin Pharmacol.*, 21: 401-404 (1981)). The reduction in adverse gastric effects has been attributed to the differences in solubility for the two agents; salsalate undergoes particulate dispersion (dissolution) in the pH of the stomach and is soluble in the pH of the small intestine, while aspirin is soluble in the acidic pH of the stomach (Harrison et al., *Therapeutic Drug Monitoring.*, 14: 87-91 (1992)). Additionally, as mentioned above, salsalate and its active metabolite salicylic acid does not inhibit cyclooxygenase I and II. All NSAIDs including aspirin inhibit cyclooxygenase I and II leading to gastric and renal toxicities. Salsalate has not been associated with any significant gastrointestinal, renal, bleeding or cardiovascular toxicity unlike the NSAID group of anti-inflammatory agents.

Figure 26:
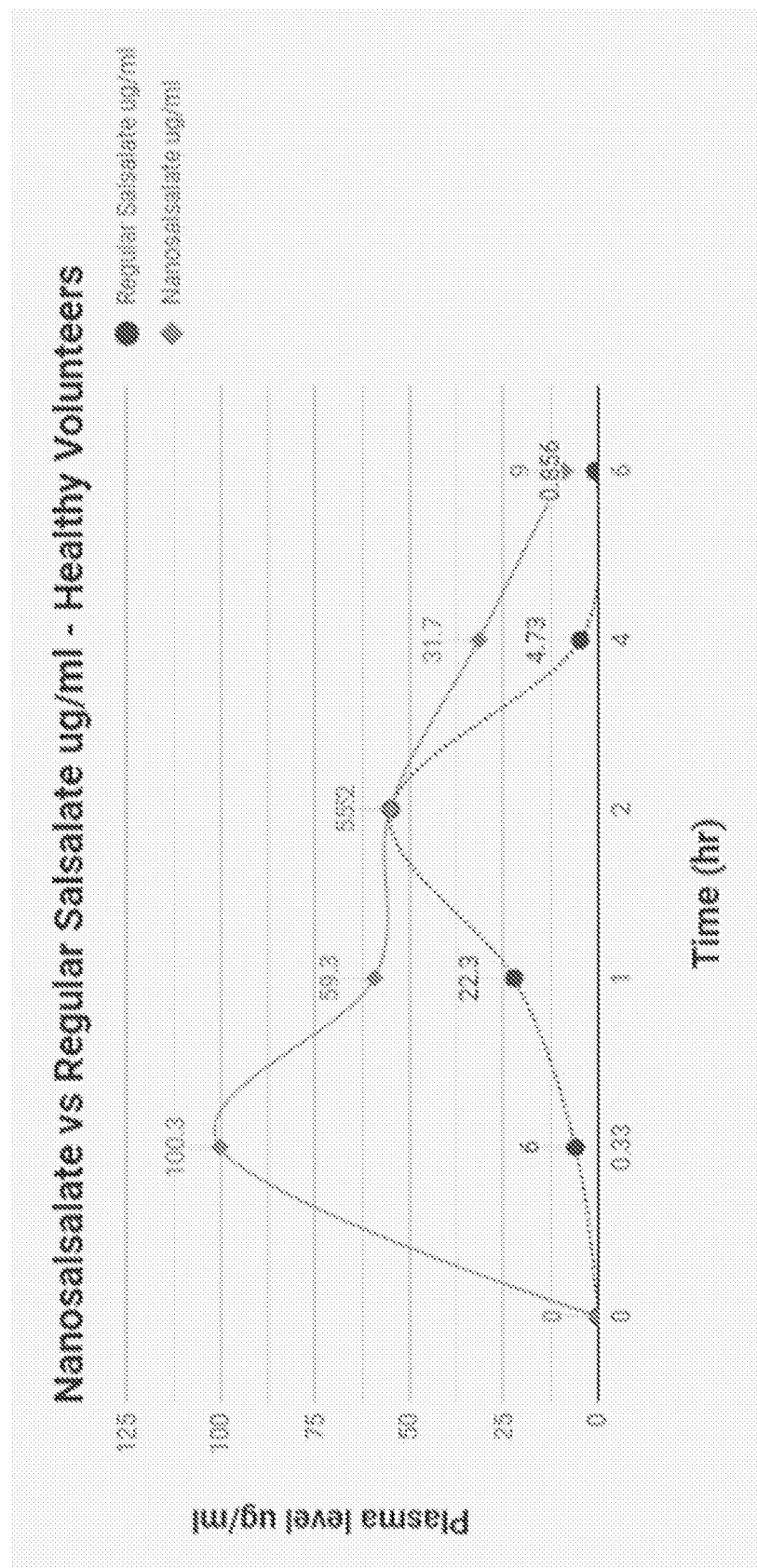
FIG. 26. Provides data on the serum level of both the parent compound salsalate (SSA) and the active metabolite salicylic acid (SA) from two healthy volunteers who have ingested a 750 mg nanosuspension of salsalate (diamond data point line). The line corresponding to the circle data points indicates a healthy subject who ingested a standard microcrystalline salsalate 750 mg tablet.
Figure 27:
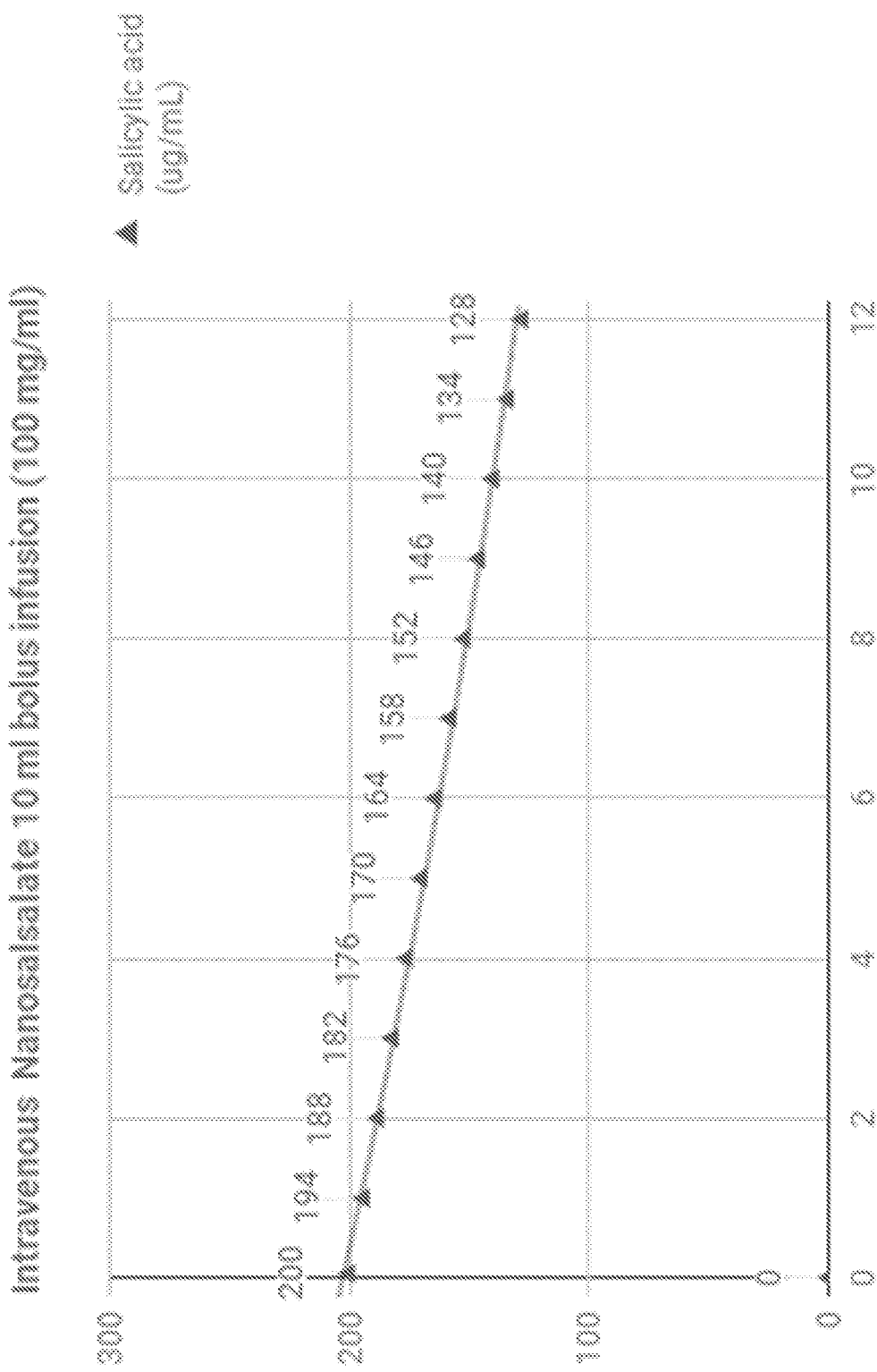
FIG. 27. Provides an ideal therapeutic window of 128-200 µg inclusive with 1000 mg intravenous salsalate nanosuspension according to the present disclosure.

The $C_{max}/T_{max}/AUC$ of both salsalate and salicylic acid using a standard oral 750 mg salsalate in a healthy volunteer was compared to the $C_{max}/T_{max}/AUC$ of a nanosuspension of 750 mg salsalate. As seen in FIG. 26, there is a dramatic increase in the $C_{max}$, shorter time to $T_{max}$ and significantly larger area under the curve (AUC) of both salsalate and salicylic acid using a nanosuspension of salsalate vs the standard microcrystalline salsalate tablet. It is expected that an intravenous formulation of a salsalate nanosuspension will lead to an even faster onset of action as there will be no "first pass effect" (liver uptake is avoided with parenteral administration) or delayed absorption due to the gastrointestinal phase of dissolution and absorption.

Salsalate nanosuspensions may be used for inflammatory disorders such as rheumatoid arthritis or noninflammatory disorders such as osteoarthritis. It is known that the risk of bleeding is a common concern with use of the NSAID class of medications, and that the bleeding risk associated with salsalate is lower than that associated with aspirin use. However, conventional, microcrystalline forms of salsalate can have significant common side effects, including upset stomach, heartburn, or mild dizziness. Such side effects are problematic for medication that is routinely taken for chronic conditions, such as osteoarthritis, as such side effects generally correlate with poor patient compliance with dosing instructions.

Data shown in the examples demonstrates that salsalate nanosuspensions have greater bioavailability as compared to microcrystalline salsalate formulations given at the same dosage. See e.g., FIGS. 24, 25A and 25B, which show plasma concentrations over time for a single 750 mg dose of a salsalate nanosuspension, as compared to FIG. 25C, which shows plasma concentration over time for a single 750 mg dose of a microcrystalline salsalate dosage form. The dramatic difference in higher $C_{max}$, lower $T_{max}$, and higher AUC for the salsalate nanosuspensions as compared to microcrystalline salsalate dosage forms given at the same dosage means that the salsalate nanosuspensions of the invention will have a greater therapeutic effect for a longer period of time.

In an exemplary embodiment, the salslate nanosuspension is formulated as a dosage form which can be an oral nanosuspension that has a "milky' color. An intravenous salslate nanosuspension formulation can also be a nanosuspension with a "milky color".

In an exemplary embodiment, the maximum oral dose taken once or twice daily of a salsalate nanosuspension is a total 24 hours dose of no greater than 4500 mg for Cytokine release prevention/treatment as well as for any other inflammatory diseases and disorders such as, but not limited to metabolic syndrome, prediabetes, and diabetes. A liquid salsalate nanosuspension for oral dosing is expected to be in a concentration of about 150-about 200 mg/ml. An intravenous salsalate nanosuspension is expected to be in a concentration of about 150-about 200 mg/ml.

In an exemplary embodiment, for inflammatory diseases such as the cytokine release syndrome/cytokine storm as well as in other inflammatory disorders the total daily dose taken may be as high as 4500 mg. Monitoring of each individual's serum salicylate level can be done to maintain optimal salicylate blood levels. Each individual taking salsalate will have different serum levels and this is the uniqueness of serum salicylate testing to achieve and maintain therapeutic serum levels of salicylic acid.

The ideal "flat" release profile for salsalate to maintain a desired PK, average plasma level of about 120-about 200 μg/mL for about 24 hours, could be a single bolus infusion of between about 1000 and about 2000 mg. Depending on the individual's serum plasma pK at $T_{max}$, the prescribing/treating physician will be able to decide the next dose period as well as need for a repeat bolus or a continuous intravenous "drip" of IV nanosalsalte.

A. Exemplary Characteristics of Salsalate Nanosuspensions

Fast onset: Conventional formulations of microcrystalline salsalate are not ideal due to delayed onset of action. In contrast, the salsalate nanosuspensions of the invention exhibit faster therapeutic effects. See e.g., Example 3. Preferably, following administration the salsalate nanosuspensions of the disclosure have a $T_{max}$ of less than about 10 hours, less than about 9 hours, less than about 8 hours, less than about 7 hours, less than about 6 hours, less than about 5 hours, less than about 4 hours, less than about 3 hours, or less than about 2 hours, less than about 1.0 hour, less than about 50 minutes, less than about 40 minutes, less than about 30 minutes, less than about 25 minutes, less than about 20 minutes, less than about 15 minutes, or less than about 10 minutes. In an exemplary embodiment, the $T_{max}$ is between about 10 minutes to about 9 hours Increased bioavailability: The salsalate nanosuspension compositions of the disclosure preferably exhibit increased bioavailability, at the same dose of salsalate, and require smaller doses, as compared to prior conventional microcrystalline salsalate compositions.

Any drug, including salsalate, can have adverse side effects. Thus, lower doses of salsalate which can achieve the same or better therapeutic effects as those observed with larger doses of conventional microcrystalline salsalate are desired. Such lower doses can be realized with the salsalate nanosuspensions of the disclosure, because the greater bioavailability observed with the salsalate nanosuspensions as compared to conventional microcrystalline salsalate means that smaller doses of salsalate are required to obtain the desired therapeutic effect.

Pharmacokinetic Profiles: The present disclosure provides salsalate nanosuspensions having a desirable pharmacokinetic profile when administered to mammalian subjects. Preferably, the $T_{max}$ of an administered dose of a salsalate nanosuspension is less than that of a conventional composition of microcrystalline salsalate, administered at the same dosage. In addition, preferably the $C_{max}$ of a salsalate nanosuspension is greater than the $C_{max}$ of a conventional composition of microcrystalline salsalate, administered at the same dosage.

In comparative pharmacokinetic testing with conventional composition of microcrystalline salsalate, a salsalate nanosuspensions, administered at the same dosage, preferably exhibits a $T_{max}$ which is less than about 100%, less than about 90%, less than about 80%, less than about 70%, less than about 60%, less than about 50%, less than about 40%, less than about 30%, less than about 25%, less than about 20%, less than about 15%, or less than about 10% of the $T_{max}$ exhibited by the conventional composition of microcrystalline salsalate.

In comparative pharmacokinetic testing with a conventional composition of microcrystalline salsalate, a salsalate nanosuspensions, administered at the same dosage, preferably exhibits a $C_{max}$ which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the $C_{max}$ exhibited by the conventional composition of microcrystalline salsalate.

The desirable pharmacokinetic profile, as used herein, is the pharmacokinetic profile measured after an initial dose of a salsalate nanosuspension. The compositions can be formulated in any way as described below.

B. Components of the Salsalate Nanosuspensions

The nanosuspensions of the disclosure comprise salsalate or a salt thereof and at least one surfactant. Surfactants useful herein associate with the surface of the salsalate particle, but do not chemically react with the salsalate molecule or itself (e.g., the surfactant is not cross-linked). Preferably, individually adsorbed molecules of the surfactant are essentially free of intermolecular cross-linkages.

The present disclosure also includes salsalate nanosuspensions having at least one surfactant associated with the surface thereof, formulated into compositions together with one or more non-toxic physiologically acceptable carriers, adjuvants, or vehicles, collectively referred to as carriers.

The present invention also includes salsalate nanosuspensions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like.

1. Salsalate

As used herein, the "drug" or "salsalate drug" or "salsalate" refers to a nanocrystal/active chemical which includes pharmaceutically acceptable salts, esters, ethers, and other derivatives of salsalate which after ingestion or parenteral administration metabolizes to salicylic acid. The nanosuspensions of the disclosure comprise salsalate which is dispersible in at least one liquid medium.

The salsalate exists as a discrete crystalline phase, as an amorphous phase, a semi-crystalline phase, a semi-amorphouse phase, or a combination thereof. The crystalline phase differs from a non-crystalline or amorphous phase which results from precipitation techniques. By "poorly soluble" it is meant that the salsalate has a solubility in a liquid dispersion medium of less than about 30 mg/mL, less than about 20 mg/mL, less than about 10 mg/mL, or less than about 1 mg/mL. Useful liquid dispersion mediums include, but are not limited to, water, aqueous salt solutions, safflower oil, and solvents such as ethanol, t-butanol, hexane, and glycol. A preferred liquid dispersion medium is water.

The salsalate is present in the nanosuspensions of the invention in a particulate form; e.g., the drug is not solubilized. As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The salsalate particles present in the nanosuspensions of the disclosure have an effective average particle size of less than about 1 micron. In other embodiments, the salsalate particles present in the nanosuspensions of the disclosure have an effective average size of less than about 900 nm, less than about 800 nm, less than about 700 nm, less than about 600 nm, less than about 500 nm, less than about 400 nm, less than about 300 nm, less than about 275 nm, less than about 250 nm, less than about 225 nm, less than about 200 nm, less than about 175 nm, less than about 150 nm, less than about 125 nm, less than about 100 nm, less than about 75 nm, or less than about 50 nm, when measured by the above techniques.

By "an effective average particle size of less than about 1 micron" it is meant that at least 50% of the salsalate particles have a particle size of less than about 1 micron, by weight, when measured by the above techniques. Preferably, at least about 70%, about 90%, about 95%, or about 99% of the particles have a particle size of less than the effective average, i.e., less than about 900 nm, less than about 800 nm, less than about 700 nm, less than about 600 nm, etc. When 70% of the salsalate particles are below a designated size, then that size is referred to as the "D70" value. The same is true for the D90, D95, etc. values.

2. Surfactants

Useful surfactants, without being bound by theory, are believed to include those which associate with the surface of the salsalate particles. In some embodiments, the surfactant is associated with the surface of the salsalate in an amount sufficient to maintain the salsalate particles at an effective average particle size of less than about 1 micron. Furthermore, in some embodiments, the individually adsorbed molecules of the surfactant are preferably essentially free of intermolecular cross-linkages. Two or more surfactants can be employed in the compositions and methods of the disclosure.

Suitable surfactants can preferably be selected from known organic and inorganic pharmaceutical excipients. Such excipients include various polymers, low molecular weight oligomers, natural products, and surfactants. Surfactants include nonionic, cationic, zwitterionic, and ionic surfactants.

Representative examples of surfactants include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3350 and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose (including grades SL and SSL), hypromellose including HPMC-606), hydroxypropylmethyl-cellulose phthalate, noncrystalline cellulose, magnesium aluminium silicate, triethanolamine, polyvinyl alcohol (PVA), polyvinylpyrrolidone (PVP), 4-(1, 1,3,3-tetramethylbutyl)-phenol polymer with ethylene oxide and formaldehyde (also known as tyloxapol, superione, and triton), poloxamers (e.g., Pluronics F68®, F127®, and F108®, which are block copolymers of ethylene oxide and propylene oxide); poloxamines (e.g., Tetronic 908 ®, also known as Poloxamine 908 ®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (DOSS) (American Cyanamid)); docusate salts such as docusate calcium, docusate sodium, and docusate potassium, Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxy-poly-(glycidol), also known as Olin-10G® or Surfactant 10G® (Olin Chemicals, Stamford, CT); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.); polysorbate 80; decanoyl-N-methylglucamide; n-decyl β-D-glucopyranoside; n-decylβ-D-maltopyranoside; n-dodecylβ-D-glucopyranoside; n-dodecylβ-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noylβ-D-glucopyranoside; octanoyl-N-methylglucamide; n-octyl-β-D-glucopyranoside; octylβ-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

Examples of useful cationic surfactants include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammonium-bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™) POLYQUAT 10™ (polyquaternium 10; Buckman Laboratories, TN), tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ (quaternized ammonium salt polymers) and ALKAQUAT™ (benzalkonium chloride) (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surfactants and other useful cationic surfactants are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surfactants are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$. (i) none of $R_1$-$R_4$ are $CH_3$; (ii) one of $R_1$-$R_4$ is $CH_3$; (iii) three of $R_1$-$R_4$ are $CH_3$; (iv) all of $R_1$-$R_4$ are $CH_3$; (v) two of $R_1$-$R_4$ are $CH_3$, one of $R_1$-$R_4$ is $C_6H_5CH_2$, and one of $R_1$-$R_4$ is an alkyl chain of seven carbon atoms or less; (vi) two of $R_1$-$R_4$ are $CH_3$, one of $R_1$-$R_4$ is $C_6H_5CH_2$, and one of $R_1$-$R_4$ is an alkyl chain of nineteen carbon atoms or more; (vii) two of $R_1$-$R_4$ are $CH_3$ and one of $R_1$-$R_4$ is the group $C_6H_5(CH_2)_n$, where n>1; (viii) two of $R_1$-$R_4$ are $CH_3$, one of $R_1$-$R_4$ is $C_6H_5CH_2$, and one of $R_1$-$R_4$ comprises at least one heteroatom; (ix) two of $R_1$-$R_4$ are $CH_3$, one of $R_1$-$R_4$ is $C_6H_5CH_2$, and one of $R_1$-$R_4$ comprises at least one halogen; (x) two of $R_1$-$R_4$ are $CH_3$, one of $R_1$-$R_4$ is $C_6H_5CH_2$, and one of $R_1$-$R_4$ comprises at least one cyclic fragment; (xi) two of $R_1$-$R_4$ are $CH_3$ and one of $R_1$-$R_4$ is a phenyl ring; or (xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Plasdone™ S-630 polymer (Ashland Global Specialty Chemicals Inc., Kentucky, USA) is a 60:40 linear random copolymer of N-vinyl-2-pyrrolidone and vinyl acetate. Plasdone S-630 is soluble in water and in many organic solvents and acts as a film-former. It is also used as a tablet binder.

Exemplary surfactants include, but are not limited to, HPC-SL, polysorbates such as polysorbate 20 (Tween 20) and polysorbate 80 (Tween 80), poloxamers such as poloxamer 407 (Pluronic F-127, which is a triblock copolymer consisting of a central hydrophobic block of polypropylene glycol flanked by two hydrophilic blocks of polyethylene glycol (PEG)) and poloxamer 188 (Pluronic F-68), PVP, combinations of HPC-SL and DOSS, combinations of HPMC and DOSS, combinations of PVP and DOSS, combinations of Plasdone S-630 (a 60:40 linear random copolymer of N-vinyl-2-pyrrolidone and vinyl acetate) and DOSS, and combinations of polysorbate 20 (Tween 20) and lecithin.

The surfactants are commercially available and/or can be prepared by techniques known in the art. Most of these surfactants are known pharmaceutical excipients and are described in detail in the *Handbook of Pharmaceutical*

*Excipients*, published jointly by the American Pharmaceutical Association and The Pharmaceutical Society of Great Britain (The Pharmaceutical Press, 2000), specifically incorporated by reference.

3. Concentration of Salsalate and Surfactant

The relative amount of salsalate and one or more surfactants can vary widely. The optimal amount of the surfactant(s) can depend, for example, the hydrophilic lipophilic balance (HLB), melting point, water solubility of the surfactant, and the surface tension of water solutions of the stabilizer, etc.

The concentration of the salsalate can vary from about 99.5% to about 0.001%, from about 85% to about 0.1%, or from about 50% to about 0.5%, by weight, based on the total combined weight of the at least one salsalate and at least one surfactant, not including other excipients. In particular embodiments, the concentration of salsalate is from about 0.01% to about 0.1%, about 0.1% to about 1%, about 1% to about 20%, about 1% to about 10%, about 5% to about 15%, or about 1% to about 50%. In exemplary embodiments, the concentration of salsalate is about 5%, about 10%, about 15%, or about 20%.

The concentration of the one or more surfactants can vary from about 0.5% to about 99.999%, from about 15% to about 99.9%, or from about 50% to about 99.5%, by weight, based on the total combined dry weight of the salsalate and at least one surfactant, not including other excipients. In exemplary embodiments, the concentration of the one or more surfactants is about 10%, about 9%, about 8%, about 7%, about 6%, about 5%, about 4%, about 3%, about 2%, about 1%, about 0.5%, or about 0.1%, by (w/w).

4. Other Pharmaceutical Excipients

Salsalate nanosuspensions according to the disclosure may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™) Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The salsalate nanosuspensions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the salsalate nanodispersion is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to salsalate, the liquid dosage forms may comprise inert diluents commonly used in the art, such as water or other solvents, solubilizing agents, and emulsifiers. Besides such inert diluents, the composition can also include adjuvants, such as wetting agents, emulsifying and suspending agents, sweetening, flavoring, and perfuming agents.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles including water, ethanol, polyols (propylene glycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

5. Non-Salsalate Active Agents

The salsalate nanosuspensions of the disclosure can additionally comprise one or more non-salsalate active agents.

Such active agents can be, for example, a pharmaceutical agent, including biologics such as amino acids, proteins, peptides, and nucleotides. The active agent can be selected from a variety of known classes of drugs, including, for example, amino acids, proteins, peptides, nucleotides, anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (anti-parkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's *The Extra Pharmacopoeia*, 31$^{st}$ Edition (The Pharmaceutical Press, London, 1996), specifically incorporated by reference. The active agents are commercially available and/or can be prepared by techniques known in the art.

The compound to be administered in combination with a salsalate nanodispersion of the disclosure can be formulated separately from the salsalate composition or co-formulated with the salsalate composition. Where an salsalate composition is co-formulated with a second active agent, the second active agent can be formulated in any suitable manner, such as immediate-release, rapid-onset, sustained-release, or dual-release form.

II. Methods of Making Salsalate Nanodispersions

The salsalate nanosuspensions can be made using, for example, milling, precipitation, or homogenization techniques.

The salsalate nanosuspensions can be utilized in any pharmaceutically acceptable dosage form, including solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

Milling: Milling of an aqueous suspension of salsalate to obtain a nanodispersion comprises dispersing salsalate particles in a liquid dispersion medium in which the salsalate is poorly soluble, followed by applying mechanical means in the presence of grinding media to reduce the particle size of the salsalate to the desired effective average particle size. The salsalate particles can be reduced in size in the presence of at least one surfactant. Alternatively, the salsalate particles can be contacted with one or more surfactants either before or after particle size reduction. Other compounds, such as a diluent, can be added to the salsalate/surfactant composition either before, during, or after the salsalate size reduction process. Dispersions can be manufactured continuously or in a batch mode.

Homogenization: An exemplary homogenization method comprises dispersing salsalate particles in a liquid dispersion medium, followed by subjecting the dispersion to homogenization to reduce the particle size of the salsalate to the desired effective average particle size. The salsalate particles can be reduced in size in the presence of at least one surfactant. Alternatively, the salsalate particles can be contacted with one or more surfactants either before or after particle size reduction. Other compounds, such as a diluent, can be added to the salsalate/surfactant composition either before, during, or after the size reduction process. Dispersions can be manufactured continuously or in a batch mode.

III. Methods of Using Salsalate Nanosuspensions

One of ordinary skill will appreciate that effective amounts of salsalate can be determined empirically and can be employed in pure form or, where such forms exist, in pharmaceutically acceptable salt, ester, or prodrug form. Actual dosage levels of salsalate in the nanosuspensions of the disclosure may be varied to obtain an amount of active ingredient that is effective to obtain a desired therapeutic response for a particular composition and method of administration. The selected dosage level therefore depends upon the desired therapeutic effect, the route of administration, the desired duration of treatment, and other factors.

The salsalate nanosuspension dose may be administered in single or multiple doses. It will be understood, however, that the specific dose level for any particular patient will depend upon a variety of factors including the body weight, general health, sex, diet, time and route of administration, potency of the administered salsalate nanosuspension, rates of absorption and excretion, combination with other drugs and the severity of the particular disease being treated, and like factors well known in the medical arts.

Preferably, the daily dose of salsalate in the nanosuspensions of the invention is less than the typical dose of microcrystalline salsalate, e.g., less than about 1500-3000 mg daily given orally in 2 or 3 divided doses. In another embodiment, the salsalate nanosuspension is given once or twice daily, including 25 mg up to about 3000 to about 4500 mg. In some embodiments, the dose of salsalate administered to the subject is selected from about 0.1 mg to about 1 gram, about 0.1 mg to about 1 mg, about 0.1 mg to about 10 mg, about 0.1 mg to about 50 mg, about 0.1 mg to about 75 mg, about 0.1 mg to about 100 mg, about 0.1 mg to about 200 mg, about 0.1 mg to about 300 mg, about 0.1 mg to about 400 mg, about 0.1 mg to about 500 mg, about 0.1 mg to about 600 mg, about 0.1 mg to about 700 mg, about 0.1 mg to about 800 mg, about 0.1 mg to about 900 mg, about 0.1 mg to about 1000 mg, about 1 mg to about 10 mg, about 10 mg to about 500 mg, about 50 mg to about 200 mg, about 100 mg to about 500 mg, about 100 mg to about 800 mg, about 100 mg to about 1000 mg, about 100 mg to about 1100 mg, about 100 mg to about 1200 mg, about 100 mg to about 1300 mg, about 100 mg to about 1400 mg, about 100 mg to about 2000 mg, about 100 mg to about 2500 mg, about 100 mg to about 3000 mg, about 100 mg to about 3500 mg, or about 100 mg to about 4500 mg, daily (or in multiple doses).

In particular embodiments, the dose of salsalate in the nanosuspension administered to the subject is about 100 mg, about 150 mg, about 200 mg, about 250 mg, about 300 mg, about 350 mg, about 400 mg, about 500 mg, about 750 mg, about 1000 mg, about 1100 mg, about 1200 mg, about 1300 mg, or about 1400 mg. In some embodiments the salsalate nanosuspension is administered to the subject once per day, twice per day, three times per day, four times per day, or as needed. In some embodiments, the salsalate nanosuspension is administered to the subject once every two days, once every three days, once every four days, once every five days, once every six days, or once per week.

The salsalate nanosuspensions of the present disclosure can be administered to humans and animals in any pharmaceutically acceptable manner, including, but not limited to orally, pulmonary, rectally, ocularly, colonicly, parenterally (e.g., intravenous, intramuscular, or subcutaneous), intravenously, intracisternally, intravaginally, intraperitoneally, locally (e.g., powders, ointments, or drops), buccally, nasal, and topically. In particular embodiments, administration is oral or intravenous. As used herein, the term "subject" is used to mean an animal, preferably a mammal, including a human or non-human. The terms patient and subject may be used interchangeably.

The present disclosure describes methods of using the formulations described herein to treat subjects (humans, veterinary animals (dogs, cats, reptiles, birds, etc.), livestock (horses, cattle, goats, pigs, chickens, etc.), and research animals (monkeys, rats, mice, fish, etc.). Subjects in need of a treatment (in need thereof) are subjects having inflammatory diseases and conditions.

The present disclosure describes a method of treating inflammatory diseases or conditions. The method includes administering to a subject in need thereof a formulation that includes salsalate. The formulation can also include other active agents, such as acetaminophen and caffeine.

In embodiments, the present disclosure describes a method of inducing analgesia in a subject in need thereof. The method includes administering the subject a single dose for analgesia pre-op or peri-op or post operatively. In embodiments, the present disclose also describes a method of reducing fever of a subject. The method includes administering to the subject a once daily long acting formulation described herein.

The salsalate nanosuspensions of the disclosure are useful in treating a subject with chronic pain. The method includes administering a formulation that includes a salsalate nanosuspension as described herein to a subject diagnosed with chronic pain.

The salsalate nanosuspensions of the disclosure are also useful in treating a subject with acute pain. The method includes administering a formulation that includes a salsalate nanosuspension as described herein to a subject diagnosed with acute pain. In some embodiments, the method includes administration of a single dose or repeated administration until the acute pain is resolved.

The salsalate nanosuspensions of the disclosure are useful in treating inflammatory diseases and conditions including but not limited to cytokine release syndrome/cytokine storm, prediabetes, diabetes, inflammatory bowel disease, Alzheimer's and non-Alzheimer's tauopathy. In other embodiments, the diabetes is Type II diabetes and the non-Alzheimer's tauopathy is PSP, CTE, or TBI. The compositions of the invention are also useful for reducing fever and pain.

The salsalate nanosuspensions of the disclosure are useful in treating diseases of the eye and related conditions including but not limited to optic nerve disorders, retinal disorders, macular degeneration, diabetes-related conditions, dry eye syndrome, allergies, and ocular infections. The method includes administering a topical formulation of the salsalate nanosuspensions described herein to the subject.

The salsalate nanosuspensions of the disclosure are useful in treating a subject diagnosed with hemophilia. The method includes administering a formulation that includes a salsalate nanosuspension as described herein to a subject diagnosed with hemophilia.

The salsalate nanosuspensions of the disclosure are useful in treating a subject diagnosed with coronary artery disease (CAD). The method includes administering a formulation that includes a salsalate nanosuspension as described herein to a subject diagnosed with coronary artery disease.

The salsalate nanosuspensions of the disclosure are useful in treating a subject diagnosed with hemophilia. The method includes administering a formulation that includes a salsalate nanosuspension as described herein to a subject diagnosed with hemophilia.

In an exemplary embodiment, a plasma concentration of 120 to 200 μg/mL of salicylic acid is maintained for a desired treatment period. In some embodiments, the desired treatment period is 2 hours or less, 4 hours or less, 6 hours or less, 12 hours or less, 18 hours or less, one day, two days, three days, four days, five days, six days, one week, two weeks, three weeks, four weeks, five weeks, six weeks, seven weeks, eight weeks, nine weeks, 10 weeks, 11 weeks, 12 weeks, 16 weeks, 20 weeks, 24 weeks, 28 weeks, 36 weeks, 40 weeks, 44 weeks, 48 weeks, 52 weeks, or longer as needed.

The salsalate nanosuspensions described herein can be administered in combination with another therapy. For example treatment of diabetes with salsalate nanosuspensions can combined with existing type II diabetes treatments, such as metformin therapy. In another example, salsalate nanosuspensions can be administered as monotherapy or add on therapy for central nervous system disorders referenced herein, as well as in combined or as monotherapy for other non central nervous system inflammatory disorders or diseases.

A. Inflammatory Conditions

The salsalate nanosuspension compositions of the disclosure are useful in treating or preventing, for example, diseases, conditions, or symptoms associated with inflammation and/or pain.

Inflammation is a protective immune response to harmful stimuli including pathogens, irritants, and damaged cells. The response involves immune cells, blood vessels, and molecular mediators which function to eliminate the harmful externally produced or internally produced stimuli and begin the healing process, such as tissue repair. Inflammation can be acute or chronic. Acute inflammation is the initial response to the harmful stimuli. It starts rapidly and becomes severe very quickly. Symptoms are present for a few days or a few weeks. Examples of diseases and conditions associated with acute inflammation include acute allergic reactions, acute bronchitis, acute appendicitis, acute dermatitis, acute meningitis, and acute sinusitis. Chronic inflammation is long-term inflammation which lasts for months or years and even for a life-time. It can also result from an autoimmune response to self-antigen. Examples of diseases and conditions associated with chronic inflammation include asthma, diabetes, tuberculosis, rheumatoid arthritis, osteoarthritis, diabetes, chronic periodontitis, Alzheimer's Disease, traumatic brain injury, ulcerative colitis, Crohn's disease, chronic sinusitis, metabolic syndrome.

Inflammation is part of the body's immune response to destroy and eliminate foreign and damaged cells. Inflammation is necessary for wound healing. However, uncontrolled inflammation which damages healthy tissues results in inflammatory disorders and diseases. Inflammation is defined in the Stedman's Medical Dictionary 1977 as "A fundamental pathologic process consisting of a dynamic complex of cytologic and histologic reactions that occur in the affected blood vessels and adjacent tissues (of man and other animals) in response to an injury or abnormal stimulation caused by a physical, chemical, or biologic agent (or combinations of such agents), including the (1) local reactions and resulting morphologic changes, (2) the destruction or removal of the injurious material, and (3) the responses that lead to repair and healing" (Stedman's Medical Dictionary).

Inflammatory diseases and conditions include those that are adhesive, allergic, alternative, atrophic, catarrhal, chronic, croupous, degenerative, exudative, fibrinopurulent, fibrinous, fibroid, granulomatous, hyperplastic, immune, interstitial, necrotic/necrotizing, parenchymatous, productive, proliferative, pseudomembranous, purulent, sclerosing, serofibrinous, serous, subacute, and supportive types. All diseases or conditions that end with the letters "itis" means inflammation.

Some examples of inflammatory diseases and conditions include all forms of arthritis, for example, osteoarthritis, rheumatoid arthritis, psoriatic arthritis; inflammatory bowel diseases, such as Crohn's disease and ulcerative colitis; asthma; systemic lupus erythematosus (SLE); dermatitis; diverticulitis; atherosclerosis; cancer; obesity; metabolic syndrome; prediabetes; and diabetes including Type I and Type II diabetes. These are the non central nervous system inflammatory diseases or disorders.

Obesity, metabolic syndrome, and prediabetes are conditions that are in a state of chronic inflammation (K. Anderson et al., American Health & Drug Benefits, 2014, Vol. 7 (4), 231-235). As a result of chronic inflammation, there is production of inflammatory cytokines, such as interleukin-6 (IL-6), tumor necrosis factor-alpha (TNF-α), C-reactive protein (CRP), and others. Id. Nuclear factor-κP (NF-κβ) is also elevated in patients with one of these three conditions. Increased cytokine production has been shown to interfere with the regulation of glucose and insulin and induce the progression of prediabetes to diabetes. Id.

Prediabetes is defined as having blood glucose levels that are higher than normal but not high enough to be diagnosed as diabetes. Id. Patients diagnosed with prediabetes have impaired glucose tolerance and impaired fasting glucose or both. Impaired glucose tolerance, as defined by the American Diabetes Association (ADA), is having a glucose level of 140 mg/dL to 199 mg/dL for two hours, based on a 75 g oral glucose tolerance test. Id. The ADA defines impaired fasting glucose as having a fasting blood glucose level ranging from 100 mg/dL to 125 mg/dL. Id. As is well-known, both impaired glucose tolerance and impaired fasting glucose are associated with altered insulin sensitivity and promotes the progression of prediabetes to diabetes. Id.

Diabetes is a group of metabolic diseases in which there is a high blood sugar level over a prolonged period. There are three main types of diabetes: Type 1 diabetes (insulin-dependent diabetes or childhood-onset diabetes), Type 2 diabetes (non-insulin-dependent diabetes or adult-onset diabetes), and gestational diabetes. Type 1 diabetes is caused by the autoimmune destruction of insulin producing beta-cells in the pancreas. Type 2 diabetes is caused by a combination of insulin resistance and inadequate insulin secretion. Gestational Diabetes is a loss of blood sugar control (hyperglycemia) that occurs during pregnancy and resolves after birth of the baby.

Type 1 diabetes results from a lack of insulin production due to an autoimmune mediated destruction of the beta cells of the pancreas. Patients require daily administration of insulin for survival and are at risk for ketoacidosis and other complications. Patients with Type 1 diabetes exhibit little or no insulin secretion as manifested by low or undetectable levels of insulin, causing hyperglycemia.

Type 2 diabetes results from insensitivity to insulin and is due to poor dietary habits, obesity, and lack of exercise. Type 2 diabetes is a growing public health issue because it is characterized by peripheral insulin resistance and failure of the pancreatic beta-cells to keep up with the increased insulin requirements, resulting in hyperglycemia. These elevated glucose levels have detrimental effects on various tissues leading to complications. Type 2 DM may be treated with medications with or without insulin. Insulin and some oral medications cause significant hypoglycemia.

Current treatment of diabetes includes administration of insulin and monitoring, using various types of instruments and devices, for the level of glucose, administration of oral hypoglycemic agents, and pancreatic beta-cell transplantation. There are great similarities between diabetes and Alzheimer's disease. Specifically, both are characterized by a metabolic disorder known as insulin resistance.

Other inflammatory diseases and conditions include in particular, those associated with inflammation of the brain or the central nervous system (CNS) including, Alzheimer's disease and non-Alzheimer's tauopathies such as Progressive Supranuclear Palsy (PSP), Chronic Traumatic Encephalopathy (CTE), and traumatic brain injury (TBI).

Neuroinflammation plays an important role in the pathogenesis of TBI (M. Lagraouri et al., Brain, Behavior, and Immunity, 2017, Vol. 61, 96-109). Tissue damage as a result of TBI involves a primary injury which is the direct damage to the brain tissue as a result of physical insult, and a secondary injury which is tissue damage caused by consequent processes such as tissue necrosis, ischemia, and activation of the inflammatory cascade. Id. Neuroinflammatory responses following TBI include activation of microglia and astrocytes, infiltration of peripheral leukocytes, and secretion of inflammatory cytokines. Upon activation, microglial cells release pro-inflammatory mediators, such as cytokines, chemokines, reactive oxygen species, and nitric oxide, and astrocytes undergo phenotypic changes, i.e. increasing in size, upregulating production of glial fibrillary acid protein and vimentin, and releasing inflammatory mediates. Id., at 97. It has been shown that post-TBI inflammatory responses persist for decades in human and persistent neuroinflammation after TBI is a cause of neurodegeneration. Id.

As mentioned above, inflammation is necessary to start the wound healing process. However, uncontrolled inflammation, left untreated, can cause more serious diseases and conditions. There is a need to develop a safe anti-inflammatory therapy for treating inflammation without inducing unacceptable adverse side effects.

Salicylates are Nonsteroidal Anti-Inflammatory Drugs (NSAIDs) that have been used to treat pain since 5th century BC. Salicylates exist in two different forms. The first form is the acetylated form, aspirin, and the second is the non-acetylated form, salsalate (salicylsalicylic acid). Aspirin has been used to treat pain, fever, inflammation, heart attacks and strokes. However, aspirin induces adverse side effects such as rash, gastrointestinal ulcerations, abdominal pain, upset stomach, heartburn, drowsiness, headache, cramping, nausea, gastritis, and bleeding.

An example of a condition routinely treated with NSAIDs is arthritis, including osteoarthritis (OA). OA is the most common form of arthritis, affecting 25-35 million people in the US. Symptomatic OA of the knee occurs in 10-13% of individuals over the age of 60. OA is caused by inflammation of the soft tissue and bony structures of the joint which worsens over time and leads to progressive thinning of articular cartilage, narrowing of the joint space, synovial membrane thickening, osteophyte formation and increased density of subchondral bone. These changes eventually result in chronic pain and disability, and deterioration of the joint despite drug therapy may require eventual surgery for total joint replacement.

Current drug treatments for OA rely on pain control with analgesics, such as narcotics and anti-inflammatory treatments with NSAIDs as well as intra-articular injections of steroids or hyaluronates. These treatments have been shown to have mixed results and may have significant limitations due to various adverse effects from the NSAIDs such as gastrointestinal erosions, ulcers, and bleeding.

Salsalate nanosuspensions may be used for inflammatory disorders such as rheumatoid arthritis or noninflammatory disorders such as osteoarthritis, and arthritis. Arthritis is defined herein as joint inflammation. Non-limiting examples of symptoms associated with arthritis include pain, stiffness, swelling, redness, and decreased range of motion.

Non-limiting examples of diseases or conditions associated with arthritis and which may be treated with the salsalate nanosuspensions of the invention include the arthritis related disease or condition selected from the group consisting of adult-onset Still's disease, ankylosing spondylitis, back pain, Behçet's disease, bursitis, calcium pyrophosphate deposition disease, carpal tunnel syndrome, chondromalacia patella, chronic fatigue syndrome, complex regional pain syndrome, cryopyrin-associated periodic syndromes, degenerative disc disease, developmental-dysplasia of hip, Ehlers-Danlos, familial mediterranean fever, fibromyalgia, fifth disease, giant cell arteritis, gout, hemochromatosis, infectious arthritis, inflammatory arthritis, inflammatory bowel disease, juvenile arthritis, juvenile dermatomyositis, juvenile idiopathic arthritis, juvenile scleroderma, Kawasaki disease, lupus, Lyme disease, mixed connective tissue disease, myositis, osteoarthritis, osteoporosis, Pagets, palindromic rheumatism, patellofemoral pain syndrome, pediatric rheumatic diseases, polymyalgia rheumatica, pseudogout, psoriatic arthritis, Raynaud's phenomenon, reactive arthritis, reflex sympathetic dystrophy, Reiter's sydrome, rheumatic fever, rheumatism, rheumatoid arthritis, scleroderma, Sjögren's disease, spinal stenosis, spondyloarthritis, systemic juvenile idiopathic arthritis, systemic lupus erythematosus, systemic sclerosis, temporal arteritis, tendinitis, vasculitis, and Wegener's granulomatosis. In particular embodiments, the diseases or conditions associated with arthritis are osteoarthritis and/or rheumatoid arthritis.

In some embodiments, treatment can be combined with one or more conventional therapies for arthritis-related diseases, conditions, or symptoms. Examples of conventional therapies for arthritis-related diseases, conditions, or symptoms include but are not limited to Abaloparatide (parathyroid hormone), Abatacept, Acetaminophen (children and infants), Acetaminophen 325 mg, Acetaminophen 500 mg, Acetaminophen 650 mg, Acetaminophen with codeine, Acetylsalicylic acid (aspirin), Actemra, Activella, Actonel, Adalimumab, Addaprin, Advil, Alendronate, Alendronate with vitamin D, Aleve, Allopurinol, Ambien, Ambien CR, Amitriptyline hydrochloride, Amrix, Anacin, Anacin (aspirin free), Anakinra, Anaprox, Anaprox DS, Apremilast, Arava, Arthrotec, Atelvia, Avinza, Azasan, Azathioprine, Azulfidine, Azulfidine EN-Tabs, Baycadron, Bayer, Belimumab, Benlysta, Betamethasone, Binosto, Boniva, Brisdelle, Bufferin, Calcitonin (nasal spray), Cambia, Canakinumab, Cataflam, Celebrex, Celecoxib, Celestone, CellCept, Certolizumab pegol, Cevimeline, Children's Tylenol, Cimzia, Climara Pro, Clinoril, Cocet, Cocet Plus, Colchicine, Colcrys, Combunox, Conjugated estrogens/bazedoxifene, ConZip, Cortef, Cortisone acetate, Cosentyx, Cyclobenzaprine, Cyclophosphamide, Cyclosporine, Cyclosporine ophthalmic emulsion, Cymbalta, Daypro, Denosumab, Dexamethasone, DexPak, Diclofenac, Diclofenac potassium, Diclofenac sodium, Diclofenac Sodium liquid/gel, Diclofenac sodium with misoprostol, Diflunisal, Dolophine, Duavee, Duexis, Duloxetine, Dyspel, EC-Naprosyn, Ecotrin, Effexor XR, Embeda, Enbrel, Endocet, Endodan, Estrace, Estratab, Estrogens, Estrogens with progesterone, Etanercept, Etodolac, Evista, Evoxac, Excedrin, Febuxostat, Feldene, Fenoprofen calcium, FeverAll, Fexmid, Flexeril, Fluoxetine, Flurbiprofen, Forteo, Fortical, Fosamax, Fosamax Plus D, Gabapentin, Gengraf, Genpril, Golimumab, Gralise, Horizant, Humira, Hycet, Hydrocet, Hydrocodone bitartrate, Hydrocodone bitartrate with acetaminophen, Hydrocodone bitartrate with ibuprofen, Hydrocortisone, Hydrogesic, Hydroxychloroquine sulfate, Hydroxypropyl cellulose pellets, Hysingla ER, Ibandronate, Ibuprofen (over-the-counter), Ibuprofen (prescription), Ibuprofen with famotidine, Ilaris, Imuran, Indocin, Indomethacin, Infant's Tylenol, Inflectra (infliximab-dyyb, biosimilar to Remicade), Infliximab, Intermezzo, I-Prin, ixekizumab, Kadian, Ketoprofen, Kevzara, Kineret, Krystexxa, KS Ibuprofen, Lacrisert, Leflunomide, lesinurad, Lorcet, Lortab, Lyrica, M, Magnacet, Maxidone, Meclofenamate sodium, Mediproxen, Medrol, Mefenamic acid, Meloxicam, Menest, Menostar, Methadone hydrochloride, Methadose, Methotrexate, Methylprednisolone, Miacalcin, Millipred, Milnacipran, Mitigare, Mobic, Morphine sulfate, Morphine sulfate oral solution, Morphine sulfate with naltrexone, Motrin, Motrin IB, MS Contin, Mycophenolate mofetil, Nabumetone, Nalfon, Naprelan, Naprosyn, Naproxen and esomeprazole magnesium, Naproxen sodium (over-the-counter), Naproxen sodium (prescription), Neoral, Neurontin, Norco, Opana, Oramorph SR, Oxapred, Orencia, Otezla, Otrexup, Oxaprozin, Oxycodone, Oxycodone hydrochloride with acetaminophen, Oxycodone with aspirin, Oxycodone with ibuprofen, OxyContin, Oxymorphone hydrochloride, Paroxetine, Paxil, PediaCare Fever Reducer/Pain Reliever, Pediapred, Pegloticase, Pennsaid, Percocet, Percodan, Pexeva, Pilocarpine, Piroxicam, Plaquenil, Ponstel, Prednisolone, Prednisone, Prednisone Intensol, Pregabalin, Prelone, Premphase, Prempro, Primlev, Probenecid, Probenecid and colchicine, Prolia, Prozac, Raloxifene hydrochloride, Rasuvo, Rayos, Reclast, Remicade, Renflexis (infliximab-abda, biosimilar to Remicade), Reprexain, Restasis, Rheumatrex, Risedronate sodium, Rituxan, Rituximab, Roxicet, Roxicodone, Rybix ODT, Ryzolt, Salagen, Sandimmune, Sarafem, Sarilumab, Savella, secukinumab, Sertraline, Simponi, Simponi Aria, Stelara, Sulfasalazine, Sulfazine, Sulfazine EC, Sulindac, Taltz, Teriparatide (parathyroid hormone), TH Ibuprofen, Therafeldamine, Tivorbex, Tocilizumab, Tofacitinib (extended release), Tofacitinib (immediate release), Tolmetin sodium, Tramadol, Tramadol (extended release), Tramadol with acetaminophen, Trexall, Tylenol Arthritis Pain, Tylenol Extra Strength, Tylenol Regular Strength, Tylenol with Codeine No. 2, Tylenol with Codeine No. 3, Tylenol with Codeine No. 4, Tymlos, Uloric, Ultracet, Ultram, Ultram-ER, Ustekinumab, Venlafaxine, Veripred 20, Vicodin, Vicoprofen, Vimovo, Vivlodex, Voltaren, Voltaren XR, Xatmep, Xeljanz, Xeljanz XR, Xodol, Xolox, Zamicet, Zipsor, Zohydro ER, Zoledronic acid, Zoloft, Zolpidem, Zolvit, Zometa, Zorvolex, Zurampic, Zydone, and Zyloprim, Success of treatment can be determined by detecting a reduction or amelioration of one or more symptoms of an inflammatory disease or condition, or a delay in the progression of an inflammatory disease or condition.

B. Cytokine Release Syndrome

Another indication that can be treated with the salsalate nanosuspensions of the invention is cytokine release syndrome/cytokine cascade. Cytokine-associated toxicity, also known as cytokine release syndrome (CRS), is a non-antigen-specific toxicity that occurs as a result of high-level immune activation. Symptoms include fever, fatigue, loss of appetite, muscle and joint pain, nausea, vomiting, diarrhea, rashes, fast breathing, rapid heartbeat, low blood pressure, seizures, headache, confusion, delirium, hallucinations, tremor, and loss of coordination.

Lab tests and clinical monitoring show low blood oxygen, widened pulse pressure, increased cardiac output (early), potentially diminished cardiac output (late), high nitrogen levels in blood, elevated D-dimer, elevated transaminases, factor I deficiency and excessive bleeding, higher-than-normal level of bilirubin.

It has surprisingly been discovered that the salsalate nanosuspensions of the invention are useful in treating cytokine release syndrome/cytokine storm.

Any pharmaceutically acceptable method of administering a salsalate nanosuspension can be used. As an exemplary protocol, the use of intravenous and/or oral formulations of a salsalate nanosuspension offers significant and unique advantages over the current treatment for CRS/cytokine storm due to the safety profile of salsalate's only known active metabolite, salicylic acid (SA). Salicylic acid has been recognized for centuries to be one of the most effective anti-inflammatory, analgesic and anti-pyretic agents. The anticipated rapid achievement of safe and therapeutic serum levels of salicylic acid from a bolus infusion of an intravenous salsalate nanodispersion should permit a reduction in the symptoms and signs if not delay onset of the cytokine release syndrome/cytokine storm. Further, oral dosing of a salsalate nanosuspension can also be used to maintain therapeutic serum levels of salicylic acid until all signs, symptoms and markers of inflammation have returned to normal. After oral administration of a salsalate nanodispersion (see FIGS. 24, 25A, and 25B) there is a very rapid elevation of both serum salsalate and serum salicylic acid, well ahead of the standard microcrystalline salsalate (FIG. 25C).

Moreover, it was found that after a rapid intravenous infusion of about 500-about 1000 mg of salsalate in a salsalate nanosuspension, a plasma concentration of salicylic acid ranging from about 120 to about 250 μg/mL is maintained over a period of at least about 12 hours for cytokine release syndrome/cytokine storm treatment and prevention. In an exemplary treatment protocol, after about 12 hours if a patient can tolerate oral medicines, the use of an oral nanosuspension of salsalate in doses specifically tailored (customized/personalized medical care) for each patient can be administered. If a patient cannot tolerate oral medicines, then a salsalate nanosuspension can be administered via gastric feeding tube or nasogastric feeding tube if in place or intravenous continuous drip to maintain a therapeutic serum salicylic acid level.

Cytokine release syndrome is a form of systemic inflammatory response syndrome that arises as a complication of some diseases or infections, and is also an adverse effect of some monoclonal antibody drugs, as well as adoptive T-cell therapies. Severe cases have been called "cytokine storms". The term "cytokine storm" appears to have been first used in 1993 in a discussion of graft vs. host disease; CRS as an adverse effect has been known since the approval of the first monoclonal antibody drug, muromonab-CD3, which causes CRS, but people working in the field of drug development at biotech and pharmaceutical companies, regulatory agencies, and academia began to more intensely discuss methods to classify it and how to mitigate its risk following the disastrous 2006 Phase I clinical trial of TGN 1412, in which the six subjects experienced severe CRS. CRS can also be referred to as an "infusion reaction".

CRS occurs when large numbers of white blood cells, including B cells, T cells, and natural killer cells, macrophages, dendritic cells, and monocytes are activated and release inflammatory cytokines, which in turn activate yet more white blood cells. This can occur when the immune system is fighting pathogens, cytokines signal immune cells such as T-cells and macrophages to travel to the site of infection. In addition, cytokines activate those cells, stimulating them to produce more cytokines.

CRS has also arisen with biotherapeutics intended to suppress or activate the immune system through receptors on white blood cells. Muromonab-CD3, an anti-CD3 monoclonal antibody, was intended to suppress the immune system to prevent rejection of organ transplants, alemtuzumab against CD52 and used to treat blood cancers as well as multiple sclerosis in organ transplants, rituximab against CD20 also used to treat blood cancers and autoimmune disorders, all cause CRS. Adoptive T-cell therapies with T-cells modified with chimeric antigen receptors (CAR-T) also causes CRS. It appears that interleukin 6 is a key mediator of CRS.

Severe CRS or cytokine storms can occur in a number of infectious and non-infectious diseases including graft-versus-host disease (GVHD), acute respiratory distress syndrome (ARDS), sepsis, Ebola, avian influenza, smallpox, and systemic inflammatory response syndrome (SIRS).[8] Cytokine storm may also be induced by certain medications, such as the CD20 antibody rituximab and the CD19 antibody tisagenlecleucel. The experimental drug TGN1412 caused extremely serious symptoms when given to six participants in a Phase I trial.[

Figure 30:
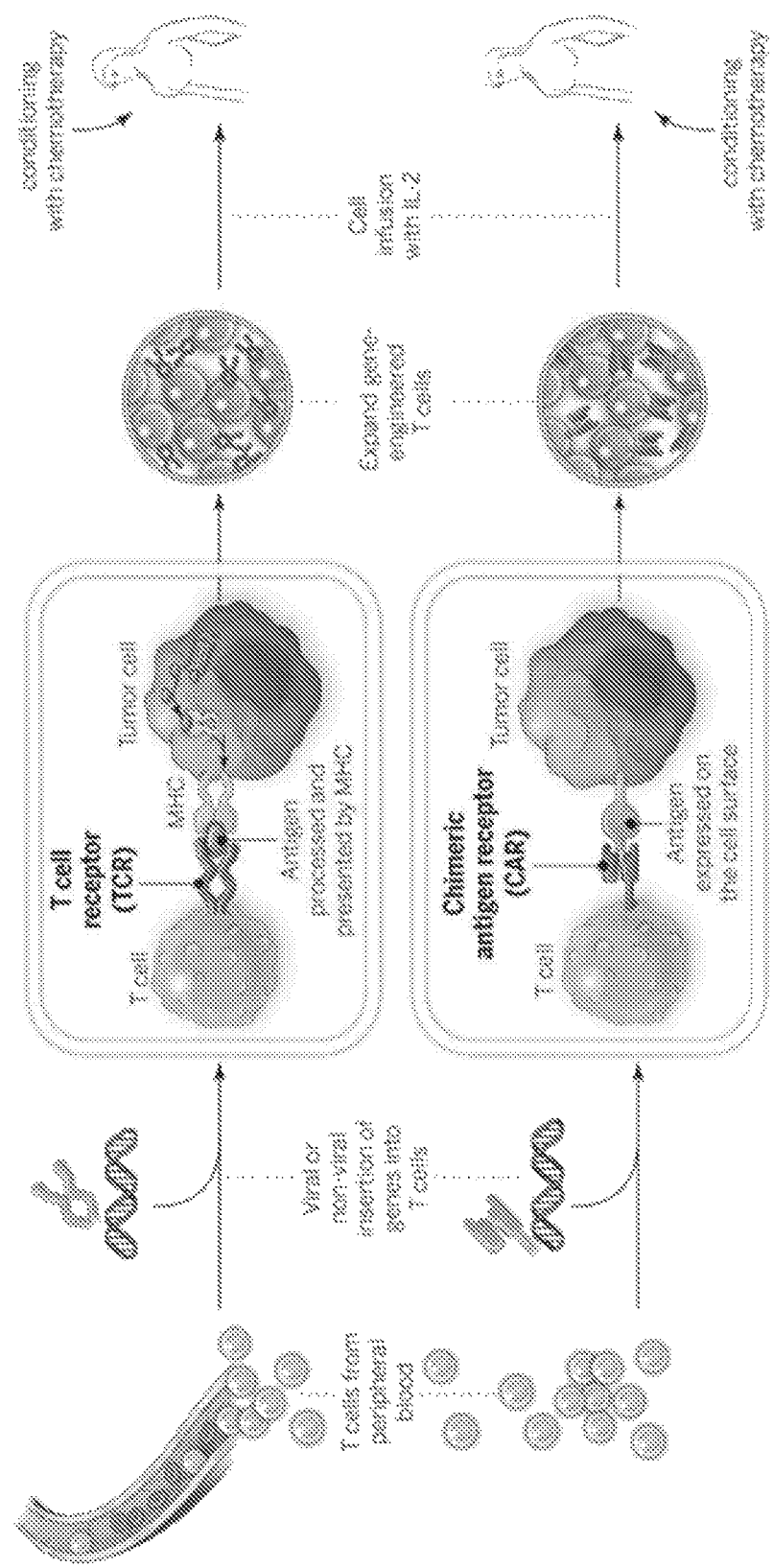
FIG. 30. Shows a pictorial of typical CAR-T therapy.

The CAR-T (Chimeric Antigen Receptor-T cell) therapy is a very new form of cancer treatment that utilizes a patient's own white blood cells referred to as "T cells" to fight blood cancers such as acute lymphoblastic leukemia. It is also being tested in solid tumors. See e.g., FIG. 30, which shows a pictorial of typical CAR-T therapy. In this type of immunotherapy the patients T cells (a form of lymphocyte) are "harvested" from the patient and treated outside the patient's body in specialized centers with advanced equipment that "tags" or "labels" on the surface of such T cells a unique antigen that is shared with the leukemia/cancer cell's surface (similar antigen on both the artificially created T-Cell as well as the/leukemia-cancer cell. When such a "treated CAR-T cell" is reinfused into the bloodstream of the leukemia/cancer patient, such treated T-cells can act as an "attacker" to the cancer cell and begin to destroy such cancer cells.

In the process of physically "binding" to the cancer cell and destroying the cancer cell, the activated CAR-T cells also release a great deal of what are referred to as "cytokines", chemical mediators of inflammation such as interleukin 6 (IL-6) and tumor necrosis factor alpha as well as other numbered interleukins and related mediators/markers of inflammation such as Interleukin-10, C-reactive protein and serum ferritin.

When the amount of such released cytokines becomes greater in amount in the body than is physiologically required, there can occur a pathological condition referred to as "cytokine release syndrome" and in the most severe form, it is called "cytokine storm". It can be fatal in severe cases and there is no effective, FDA approved treatment for prevention, slowing, delaying onset or reversing the symptoms and signs of a cytokine release syndrome or cytokine storm. Such symptoms and signs often include high fever, confusion, blood coagulation disorders, respiratory distress syndrome as well as renal disorders to name but a few. Current treatments for the cytokine release syndrome (CRS) and cytokine storm rely upon supportive measures such as medicines to raise low blood pressure such as dopamine and epinephrine as well as ventilator support for respiratory failure/distress. Use of high dose corticosteroids is also used as well as the off label use of an interleukin 6 (IL-6) receptor antigen antagonist called tocilizumab (Actemra®).

Treatment for less severe CRS is supportive, addressing the symptoms like fever, muscle pain, or fatigue. Moderate CRS requires oxygen therapy and giving fluids and antihypotensive agents to raise blood pressure. For moderate to severe CRF, the use of immunosuppressive agents like corticosteroids may be necessary, but judgement must be used to avoid negating the effect of drugs intended to activate the immune system. Tocilizumab, an anti-IL6 monoclonal antibody, has been used in some medical centers to treat severe CRS. Both steroids and tocilizumab are associated with severe and potentially life threatening complications superimposed upon at times critically ill patients battling CRS and cytokine storm conditions.

Thus, CRS is a form of systemic inflammatory response syndrome and is an adverse effect of some drugs. The Common Terminology Criteria for Adverse Events classifications for CRS as of version 4.03 issued in 2010 are shown in Table 1 below.

TABLE 1

| | |
|---|---|
| Grade 1 | Mild reaction, infusion interruption not indicated; intervention not indicated |
| Grade 2 | Therapy or infusion interruption indicated but responds promptly to symptomatic treatment (e.g., antihistamines, NSAIDS, narcotics, IV fluids); prophylactic medications indicated for <=24 hrs |
| Grade 3 | Prolonged (e.g., not rapidly responsive to symptomatic medication and/or brief interruption of infusion); recurrence of symptoms following initial improvement; hospitalization indicated for clinical sequelae (e.g., renal impairment, pulmonary infiltrates) |
| Grade 4 | Life-threatening consequences; pressor or ventilatory support indicated |
| Grade 5 | Death |

Success of treatment can be determined by detecting a reduction or amelioration of one or more symptoms of cytokine release syndrome/cytokine cascade, a delay in the progression of the cytokine release syndrome/cytokine cascade, or a reduction in the intensity of the cytokine release syndrome/cytokine cascade.

Figure 31:
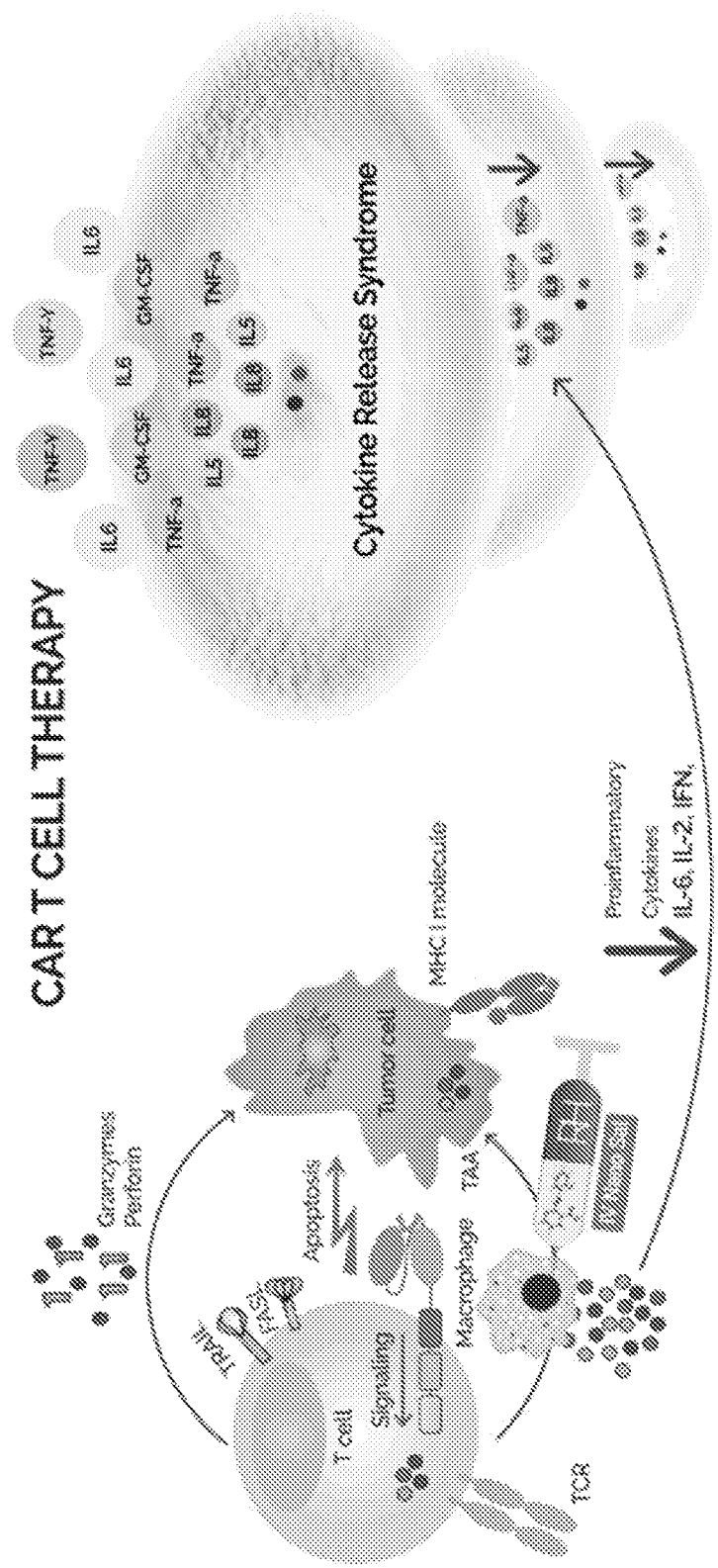
FIG. 31. Shows a pictorial representation of cytokine release syndrome/cytokine storm (CRS/CS) with respect to CAR-T cell therapy, and how a salsalate nanosuspension is expected to prevent the release of excessive IL-6 and other cytokines, pre-symptomatically and symptomatically.
Figure 32:
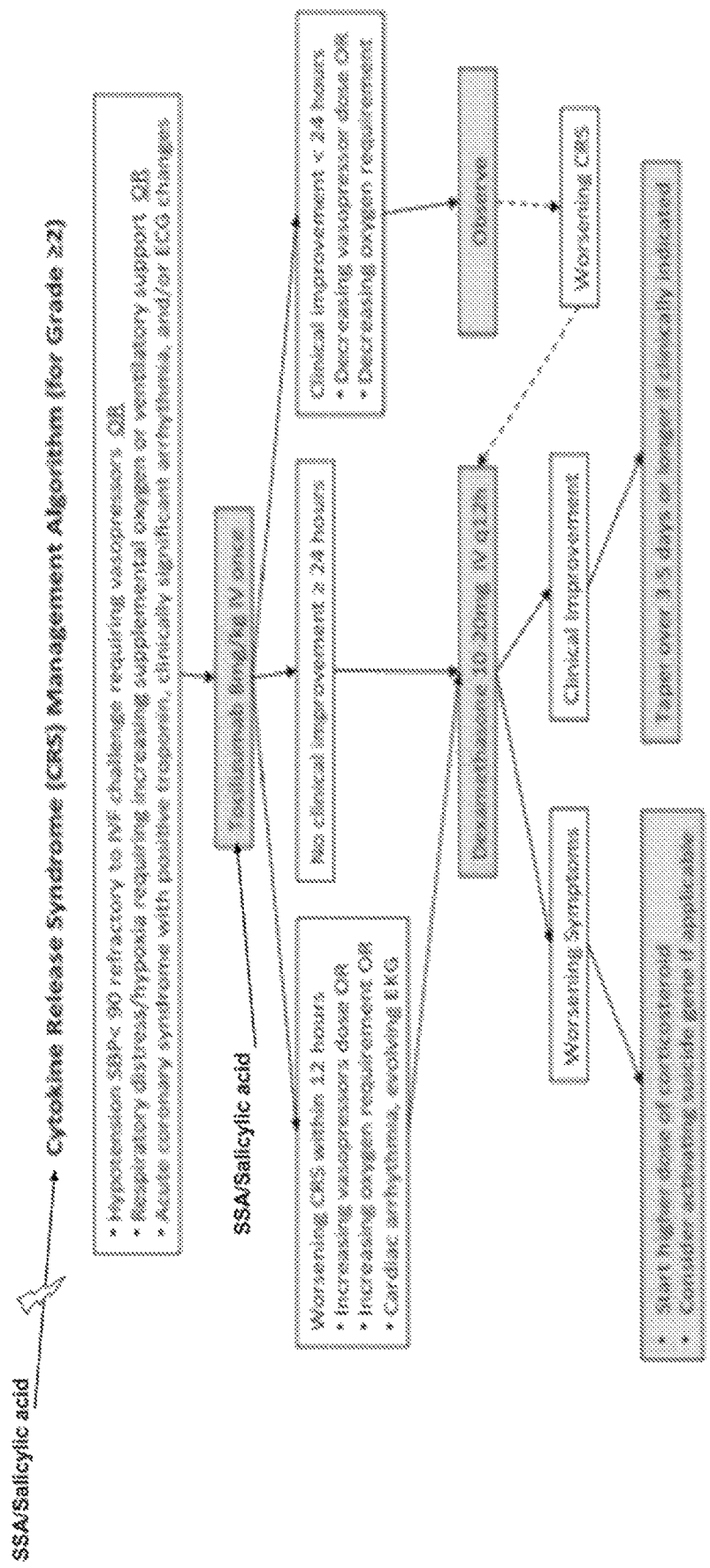
FIG. 32. Shows a flow chart algorithm of cytokine release syndrome management at Memorial Sloan Kettering Cancer Center (MSKCC). The diagram shows the updated management guideline of Grade 2 or higher cytokine release syndrome in patients being treated with 19-28z CAR-T cells at MSKCC.

FIG. 31 shows a pictorial representation of cytokine release syndrome/cytokine storm (CRS/CS) with respect to CAR-T cell therapy, and how a salsalate nanosuspension is expected to prevent the release of excessive IL-6 and other cytokines, pre-symptomatically and symptomatically. In particular, salsalate nanosuspensions of the disclosure are expected to prevent, delay onset, as well as slow the progression of CRS/CS in subjects in need; for example, in leukemia patients undergoing CAR-T therapy. As such, salsalate nanosuspensions of the disclosure are expected to be preventative as well as interventional for CRS/CS. See also, FIG. 32, which shows a flow chart algorithm of cytokine release syndrome management at Memorial Sloan Kettering Cancer Center (MSKCC). The diagram shows the updated management guideline of Grade 2 or higher cytokine release syndrome in patients being treated with 19-28z CAR-T cells at MSKCC.

C. Eye Diseases and Conditions

The salsalate nanosuspensions of the disclosure are useful in treating or preventing, diseases, conditions, or symptoms associated with the eye. Eye diseases, conditions, or symptoms include but are not limited to disorders of the eyelid, lacrimal system, orbit, conjunctiva, sclera, cornea, iris, ciliary body, choroid, retina, vitreous body, globe, optic nerve, visual pathways, ocular muscles, binocular movement, accommodation, refraction, vision, and adnexa.

The salsalate nanosuspensions of the present disclosure are useful in overcoming the safety challenges and delivery challenged faced by conventional topical ophthalmic NSAIDs. Conventional NSAIDs are commonly used in the treatment of diseases or conditions associated with the eye such as post-operative inflammation following cataract extraction and various surgical refractive procedures. They are also used in the prevention and treatment of cystoid macular oedema and for the treatment of allergic conjunctivitis. Absorption of topical ophthalmic NSAIDs through the nasal mucosa results in systemic exposure and the occurrence of adverse systemic events, including exacerbation of bronchial asthma. Local irritant effects of topical ophthalmic NSAIDs include conjunctival hyperaemia, burning, stinging and corneal anaesthesia. A more serious complication involves the association of topical ophthalmic NSAIDs with indolent corneal ulceration and full-thickness corneal melts.

Non-limiting examples of diseases or conditions associated with the eye and which may be treated with the salsalate nanosuspensions of the disclosure include the eye related disease or condition selected from the group consisting of age-related macular degeneration, albinism, amblyopia, anisocoria, astigmatism, bacterial keratitis, Bell's palsy, black eye, blepharitis, blocked tear duct, branch retinal vein occlusion (BRVO), cataracts and/or post-operative inflammation following cataract surgery, cellulitis, central retinal vein occlusion, central serous chorioretinopathy, chalazia and stye, choroidal neovascular membranes, chronic angle-closure glaucoma, coloboma, color blindness, conjunctivitis (pink eye), contact lens-related eye infections, corneal abrasion, corneal dystrophies, corneal erosion, corneal laceration, corneal ulcer, cytomegalovirus retinitis, detached or torn retina, diabetic retinopathy, drusen, dry eye, eye allergies, eye cancer, eye lymphoma, eyelid spasm and twitching, farsightedness (hyperopia), floaters and flashes, Fuchs' dystrophy, fungal keratitis, giant cell arteritis, glaucoma, Graves disease, hemangioma, herpes keratitis, herpes zoster (shingles), heterochromia, histoplasmosis, HIV/AIDS, hyphema, iridocorneal endothelial syndrome, ischemic optic neuropathy, juvenile idiopathic arthritis uveitis, juvenile macular degeneration, keratitis, keratoconus, lazy eye (amblyopia), low vision, macular edema, macular hole, macular pucker, macular telangiectasia, Marfan syndrome, microvascular cranial nerve palsy, migraine, myasthenia gravis, myopia, nevus, nystagmus, ocular hypertension, ocular melanoma, onchocerciasis (African river blindness), optic neuritis, orbital fracture, photokeratitis, pigment dispersion syndrome, pinguecula and pterygium, pink eye (conjunctivitis), posterior vitreous detachment, presbyopia, ptosis, retinal artery occlusion, retinal detachment, retinitis pigmentosa, retinoblastoma, retinopathy of prematurity, river blindness (onchocerciasis), scleritis, shingles (herpes zoster), Sjögren's syndrome, Stargardt disease, Stickler syndrome, strabismus, subconjunctival hemorrhage, trachoma, trichiasis, Usher syndrome, uveitis, and vitamin A deficiency.

The salsalate nanosuspensions of the disclosure are useful in the treatment of dry eye syndrome. Dry eye is a common multifactorial disease that can be characterized by changes in the ocular surface epithelia related to reduced tears quantity and ocular surface sensitivity, leading to inflammatory reaction. Current treatments include management of eye inflammation, use of topically applied artificial tear products/lubricants, tear retention management, stimulation of tear secretion, and use of anti-inflammatory drugs. Symptoms of dry eye syndrome include but are not limited to burning sensation, itchy eyes, aching sensations, heavy eyes, fatigued eyes, sore eyes, dryness sensation, red eyes, photophobia (light sensitivity), blurred vision.

Any pharmaceutically acceptable method of administering a salsalate nanosuspension to the eye or regions near the eye can be used. Nonlimiting examples of salsalate nanosuspension drug formulations suitable for use in or near the eye include but are not limited to ocular inserts, minitablets, and topical formulations such as eye drops, ointments, and in situ gels. In some embodiments, a contact lens is coated with a salsalate nanosuspension of the present disclosure. In some embodiments, the ocular formulation of salsalate nanosuspension is sterile.

Eye drops comprise a sterile liquid formulation that can be administered directly to the eye. In some embodiments, eye drops comprising a salsalate nanosuspension of the present disclosure further comprise one or more preservatives. The optimum pH for eye drops equals that of tear fluid and is about 7.4.

In situ gels are viscous liquids, showing the ability to undergo sol-to-gel transitions when influenced by external factors, like appropriate pH, temperature, and the presence of electrolytes. This property causes slowing of drug drainage from the eyeball surface and increase of the active ingredient bioavailability. Polymers commonly used in in situ gel formulations include but are not limited to gellan gum, poloxamer, and cellulose acetate phthalate.

Ointments are semisolid dosage forms for external use. In some embodiments, ointments comprise a solid or semisolid hydrocarbon base of melting or softening point close to human body temperature. After applying the ointment to the eye, it decomposes into small drops, which stay for a longer time period in conjunctival sac, thus increasing drug's bioavailability.

Ocular inserts are solid or semisolid dosage forms without disadvantages of traditional ophthalmic drug forms. They are less susceptible to defense mechanisms like outflow through nasolacrimal duct, show the ability to stay in conjunctival sac for a longer period, and are more stable than conventional dosage forms. They also offer advantages such as accurate dosing of salsalate, slow salsalate release with constant speed, and limiting of salsalate's systemic absorption. In some embodiments, an ocular insert comprises a salsalate nanosuspension of the present disclosure and one or more polymeric materials. The polymeric materials include but are not limited to methylcellulose and its derivatives (e.g., hydroxypropyl methylcellulose (HPMC)), ethylcellulose, polyvinylpyrrolidone (PVP K-90), polyvinyl alcohol, chitosan, carboxymethyl chitosan, gelatin, and various mixtures of the aforementioned polymers.

Minitablets are biodegradable, solid drug forms, that, after application to conjunctival sac, transit into gels, which extends the time period of contact between active ingredient and the eyeball surface, which in turn increases the active ingredient's bioavailability. The advantages of minitablets include easy application to conjunctival sac, resistance to defense mechanisms like tearing or outflow through nasolacrimal duct, longer contact with the cornea caused by presence of mucoadhesive polymers, and gradual release of salsalate from the formulation in the place of application due to the swelling of the outer carrier layers. Minitablets comprise salsalate nanosuspensions of the present disclosure and one or more polymers. Non-limiting examples of polymers suitable for use in in a minitablet formulation include cellulose derivatives, like hydroxypropyl methylcellulose (HPMC), hydroxyethyl cellulose (HEC), sodium carboxymethyl cellulose, ethyl cellulose, acrylates, that is, polyacrylic acid and its cross-linked forms, Carbopol or Carbomer, chitosan, starch, for example, and drum-dried waxy maize starch. In some embodiments, minitablets further comprise one or more excipients. Nonlimiting examples of excipients include mannitol and magnesium stearate. Minitablets are developed applying the method of direct compression or indirect method, the latter involving tableting the earlier obtained granules. The advantage of indirect method is the dry granulation stage, which increases flow properties of powders often containing bioadhesive polymers, which enables minitablets production on a larger than laboratory scale.

In some embodiments, the viscosity of the salsalate nanosuspension is increased to improve contact with the cornea and bioavailability in the eye. Viscosity can be increased by the addition of hydrophilic polymers of high molecular weight which do not diffuse through biological membranes and which form three-dimensional networks in the water. Non-limiting examples of such polymers include polyvinyl alcohol, poloxamers, hyaluronic acid, carbomers, and polysaccharides, cellulose derivatives, gellan gum, and xanthan gum.

It is anticipated that the ocular salsalate nanosuspensions described herein provide advantages over traditional formulations including increased bioavailability through reduced susceptibility to defense mechanisms of the human eye, extending contact time of drug with the cornea, increasing the penetration through the complex anatomical structure of the eye, and providing controlled release of salsalate into the eye tissues, which can lead to a reduction in the drug application frequency.

In some embodiments, the method includes administration of a single dose of the ocular salsalate nanosuspension. In other embodiments, the method includes administration of a dose every 2 hours, every 3 hours, every 4 hours, every 5 hours, every 6 hours, every 7 hours, every 8 hours, every 9 hours, every 10 hours, every 11 hours, every 12 hours, every 14 hours, every 16 hours, every 18 hours, daily, every 2 days, every 3 days, every 4 days, every 5 days, every 6 days, every week, or as needed.

Success of treatment can be determined by detecting a reduction or amelioration of one or more symptoms associated with an eye disease or condition or a delay in the progression of the eye disease or condition. Symptoms of diseases or conditions associated with the eye include but are not limited to blood in the eye, bloodshot eye, blurriness, burning eyes, bulging eyes, crusty eyelid or eyelashes, dark spots in vision, dilated pupil, discharge from eye, distorted vision, double vision, drooping eyelid, dryness, enlarged pupil, eyelid turns out, flashes of light, floaters in vision, grittiness, halos around lights, headache behind eye, irritation, itchiness, inflammation, light sensitivity, limited movement of eyelid, limited movement of eyes, lump on eyelid, night vision problems, pain around eye, pain behind eye, pain in eye, pink eye (symptom), red eye, reduced vision, shadow or dark curtain in vision, spasm and/or twitching, brown, cloudy, white, red or pink, or yellow spots on the eye, colored spots on an eyelid, starbursts around lights, swelling around the eye, swollen eye, tearing, tunnel vision, vision loss, central, and general or peripheral vision loss.

D. Hemophilia

The salsalate nanosuspension compositions of the disclosure are useful in treating subjects diagnosed with hemophilia. In particular embodiments, the salsalate nanosuspensions of the disclosure are useful in the management of pain, treating inflammation, and/or treating one or more symptoms of hemophilia in subjects diagnosed with hemophilia.

Hemophilia is a disorder that involves an impaired ability to form blood clots. As a result, patients with hemophilia exhibit spontaneous bleeding and bleeding longer after an injury, easy bruising, and an increased risk of bleeding inside joints or the brain. Patients with a mild case of hemophilia may exhibit symptoms only after an accident or during surgery. Bleeding into a joint can result in permanent damage while bleeding in the brain can result in long term headaches, seizures, or a decreased level of consciousness. Symptoms of hemophilia include but are not limited to excessive bleeding, spontaneous nosebleeds, blood in the urine, blood in the stool, large bruises, bleeding in the joints, tightness of joints, swollen joints, painful joints, bleeding in the brain, headaches, neck pain, neck stiffness, repeated vomiting, sleepiness, changes in behavior, sudden weakness or clumsiness of the limbs, double vision, and convulsions or seizures.

The two major types of hemophilia are hemophilia A, which occurs due to a deficiency in clotting factor VIII, and hemophilia B, which occurs due to a deficiency in clotting factor IX. Hemophilia is typically an inherited genetic disorder. Some rare forms of hemophilia may be acquired through spontaneous genetic mutation or development of antibodies to a clotting factor. Other types include haemophilia C, which occurs due to a deficiency in factor XI, and parahaemophilia, which occurs due a deficiency in factor V.

The management of pain and inflammation in hemophilic arthropathy is challenging due to the lack of anti-inflammatory analgesic agents suitable for use in a population of patients with bleeding disorders. Use of NSAIDs in patients with hemophilia is limited due to increased risk of bleeding from the upper gastrointestinal tract. The salsalate nanosuspensions of the present disclosure are useful in overcoming the safety challenges faced by conventional NSAIDs because they have reduced risk of adverse events such as bleeding.

Any pharmaceutically acceptable method of administering a salsalate nanosuspension to a subject can be used to treat a subject with hemophilia. In some embodiments, the formulation is an oral formulation such as a tablet. In an exemplary embodiment, a plasma concentration of about 120 to about 200 µg/mL of salicylic acid is maintained for a desired treatment period.

In some embodiments, the method includes administration of a single dose of a salsalate nanosuspension. In other embodiments, the method includes administration of a dose every 2 hours, every 3 hours, every 4 hours, every 5 hours, every 6 hours, every 7 hours, every 8 hours, every 9 hours, every 10 hours, every 11 hours, every 12 hours, every 14 hours, every 16 hours, every 18 hours, daily, every 2 days, every 3 days, every 4 days, every 5 days, every 6 days, every week, or as needed.

Success of treatment can be determined by a reduction in the amount or degree of pain experienced by the subject, detecting decreased inflammation in the subject, and/or detecting a reduction or amelioration of one or more symptoms associated with hemophilia in the subject.

E. Coronary Artery Disease

The salsalate nanosuspension compositions of the disclosure are useful in treating or preventing coronary artery disease. They are also useful in managing pain, treating inflammation, and/or reducing the risk of stroke, heart attack, kidney failure, and congestive heart failure in subjects diagnosed with coronary artery disease.

Coronary artery disease (CAD) involves a reduction of blood flow and oxygen to the heart muscle due to atherosclerosis of the arteries of the heart. CAD may also refer to diseases including but not limited to stable angina, unstable angina, myocardial infarction, and sudden cardiac death. Symptoms of CAD include but are not limited to angina, (defined as discomfort, heaviness, tightness, pressure, aching, burning, numbness, fullness, or squeezing of the chest, left shoulder, arms, neck, back or jaw), pain or discomfort in other areas of the upper body including the arms, back, or stomach, difficulty breathing or shortness of breath, sweating, fullness, indigestion, nausea, vomiting, light-headedness, dizziness, extreme weakness, anxiety, and rapid or irregular heartbeat. Subjects with CAD have an increased risk of stroke, heart attack, kidney failure, and congestive heart failure.

Because NSAIDs, particularly nonselective NSAIDs and COX2 selective NSAIDs, bear an increased risk of adverse cardiovascular events, they are not suitable for use in treating subjects diagnosed with CAD. The salsalate nanosuspensions of the present disclosure are useful in overcoming the safety challenges faced by these NSAIDs because they have reduced risk of cardiovascular adverse events.

Any pharmaceutically acceptable method of administering a salsalate nanosuspension to a subject can be used. In some embodiments, the formulation is an oral formulation such as a tablet. In an exemplary embodiment, a plasma concentration of 120 to 200 µg/mL of salicylic acid is maintained for a desired treatment period.

In some embodiments, a salsalate nanosuspension of the present disclosure is administered to a subject at risk of developing CAD. Risk factors for CAD include but are not limited high blood pressure, smoking, diabetes, lack of exercise, obesity, high blood cholesterol, poor diet, depression, and excessive alcohol. The nanosuspensions are administered every 12 hours, daily, every 48 hours, or as needed to reduce the risk of developing CAD. Treatment with the salsalate nanosuspension results in reduced risk of developing CAD and/or prevention of CAD.

In some embodiments, the method includes administration of a single dose of a salsalate nanosuspension. In other embodiments, the method includes administration of a dose every 2 hours, every 3 hours, every 4 hours, every 5 hours, every 6 hours, every 7 hours, every 8 hours, every 9 hours, every 10 hours, every 11 hours, every 12 hours, every 14 hours, every 16 hours, every 18 hours, daily, every 2 days, every 3 days, every 4 days, every 5 days, every 6 days, every week, or as needed.

Success of treatment can be determined by a reduction in the amount or degree of pain experienced by the subject, detecting decreased inflammation in the subject, and/or detecting a reduction or amelioration of one or more symptoms associated with CAD in the subject.

F. Chronic and Acute Pain

The salsalate nanosuspension compositions of the disclosure are useful in treating pain. In some embodiments, the salsalate nanosuspension compositions of the disclosure are useful in treating acute pain. In other embodiments, the salsalate nanosuspension compositions of the disclosure are useful in treating chronic pain. In some embodiments, the salsalate nanosuspension compositions of the disclosure are useful in inducing analgesia in a subject in need thereof.

Pain is an unpleasant sensory and emotional experience associated with actual or potential tissue damage, or described in terms of such damage. Different types of pain include but are not limited to nociceptive pain, which is pain caused by stimulation of sensory nerve fibers, neuropathic pain, which is pain caused by damage or disease affecting any part of the nervous system, allodynia, which is pain experienced in response to normally painless stimuli, phantom pain, which is pain felt in a part of the body that has been amputated or from which the brain no longer receives signals, psychogenic pain, which is pain caused, increased, or prolonged by mental, emotional, or behavioral factors, and breakthrough pain, which is transitory acute pain that is common in cancer patients. Pain can regarded as a stand-alone disease or condition, or a symptom of an underlying disease or condition.

Pain can also be classified by duration. Acute pain is pain that lasts for a period of less than 30 days. Chronic pain is pain with sustained duration for a period lasting at least 30 days. Chronic pain may originate in the body, brain, or spinal cord and is difficult to treat. Severe chronic pain is associated with increased 10 year mortality, particularly from heart disease and respiratory disease. People with chronic pain tend to have higher rates of depression, anxiety, and sleep disturbances and may contribute to decreased physical activity due to fear of exacerbating pain, often resulting in weight gain. Chronic pain includes but is not limited to chronic primary pain, chronic cancer pain, chronic posttraumatic pain, chronic neuropathic pain, chronic headache and orofacial pain, chronic visceral pain, and chronic musculoskeletal pain.

Pain can be categorized and/or assessed by any method known in the art including but not limited to the International Association for the Study of Pain (IASP) classification, the visual analog scale (VAS), and the multidimensional pain inventory (MPI). The IASP classification describes pain according to five characteristics: region of the body involved, system whose dysfunction may be causing the pain, duration and pattern of occurrence, intensity and time since onset, and cause. The VAS scale is a psychometric response scale that comprises a continuous line anchored by verbal or visual descriptors, one for each extreme of pain where a higher score indicates greater pain intensity. Cut-offs for pain classification may include: no pain, mild pain, moderate pain, and severe pain. MPI is a questionnaire designed to assess the psychosocial state of a person with chronic pain. The questionnaire identifies three classes of subjects with chronic pain: (a) dysfunctional: subjects who perceive the severity of their pain to be high, report that pain interfers with much of their lives, report a higher degree of psychological distress caused by pain, and report low levels of activity; (b) interpersonally distressed: subjects with a common perception that significant others were not very supportive of their pain problems; and (c) adaptive copers: subjects who report high levels of social support, relatively low levels of pain and perceived interference, and relatively high levels of activity. The MPI or VAS may be combined with the IASP classification.

Currently, NSAIDs are used extensively as analgesics in the management of chronic pain as well as acute pain due to trauma, surgery, headache, musculoskeletal injuries, and cancer. However, despite the long-term use of NSAIDs is a leading cause of drug-related morbidity, especially in elderly subjects who often have comorbidities which require treatment with medications with which NSAIDs are known to interact (e.g., aspirin, anti-coagulants, anti-depressants, and, anti-hypertensives), and those patients with risk factors, such, as a history of peptic ulcer, myocardial infarction, stroke, or heart failure, or with impaired renal function. The salsalate nanosuspensions of the present disclosure provide an alternative analgesic treatment for chronic and acute pain that avoids the safety challenges faced by conventional NSAIDs.

Any pharmaceutically acceptable method of administering a salsalate nanosuspension to a subject can be used. In some embodiments, the formulation is an oral formulation such as a tablet. In some embodiments, the formulation further comprises other active agents such as acetaminophen and caffeine. In an exemplary embodiment, a plasma concentration of 120 to 200 µg/mL of salicylic acid is maintained for a desired treatment period.

In some embodiments, the method includes administration of a single dose of a salsalate nanosuspension. In other embodiments, the method includes administration of dose every 2 hours, every 3 hours, every 4 hours, every 5 hours, every 6 hours, every 7 hours, every 8 hours, every 9 hours, every 10 hours, every 11 hours, every 12 hours, every 14 hours, every 16 hours, every 18 hours, every day, every two days, or as needed until the pain is reduced or resolved.

Success of treatment can be determined by resolution of the subject's pain or by detecting a reduction in the amount, degree, or frequency of pain experienced by the subject. In some embodiments, pain reduction is identified by an improvement in the subject's VAS score, IASP classification, and/or MPI identification.

IV. Definitions

"About" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term. When further clarity is required, the term "about" has the meaning reasonably ascribed to it by a person skilled in the art when used in conjunction with a stated numerical value or range, i.e. denoting somewhat more or somewhat less than the stated value or range, to within a range of ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

As used herein with reference to stable drug particles, 'stable' means that salsalate particles do not appreciably flocculate or agglomerate due to interparticle attractive forces or otherwise increase in particle size.

"Therapeutically effective amount" as used herein with respect to a drug dosage, shall mean that dosage that provides the specific pharmacological response for which the drug is administered in a significant number of subjects in need of such treatment. It is emphasized that 'therapeutically effective amount,' administered to a particular subject in a particular instance will not always be effective in treating the diseases described herein, even though such dosage is deemed a 'therapeutically effective amount' by those skilled in the art. It is to be further understood that drug dosages are, in particular instances, measured as oral dosages, or with reference to drug levels as measured in blood.

"Conventional active agents or drugs" refers to non-nanoparticulate or solubilized active agents or drugs. Non-nanoparticulate active agents have an effective average particle size of greater than about 1 micron.

As used herein, "salsalate" refers to a chemical of the following structural formula and any pharmaceutically acceptable salt, ester, or prodrug form thereof:

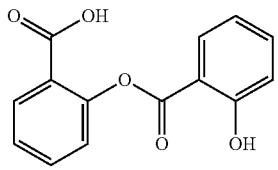 [SMILES: O=C(Oc1ccccc1C(=O)O)c1ccccc1O]

The IUPAC name of salsalate is 2-hydroxybenzoyloxy benzoic acid. Salsalate has a molecular weight of 258.229 and the empirical formula is $C_{14}H_{10}O_5$. The USP reported melting point of salsalate is 147° C. The acidic functions calculated pKa is 3.4. Salsalate is available, for example, from Anthem Biosciences (India).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The following examples are given to illustrate the present invention. It should be understood, however, that the invention is not to be limited to the specific conditions or details described in the examples. Throughout the specification, any and all references to a publicly available document, including a U.S. patent, are specifically incorporated by reference.

Example 1

This example describes preparation of formulations of salsalate nanosuspensions.

Formulation Summary

A roller mill excipient screen was conducted with salsalate using standard oral Center for Drug Evaluation and Research ("CDER") listed inactive ingredients. The pH of salsalate in water was slightly below 4, so no pH adjustment was attempted. The samples were analyzed using Horiba light scattering particle size distributions (PSD). One of several acceptable formulations was selected to scale up to a higher concentration of API using high speed media milling.

Starting API

Analysis of an unmilled aqueous suspension of 5% salsalate is shown in FIGS. 1A and 1B. FIG. 1A shows an OM of aqueous 5% suspension of unmilled salsalate, and FIG. 1B shows the results of a particle size analysis of the composition using a Horiba light scattering particle size analyzer. As detailed in FIG. 1B, the unmilled salsalate composition had a median, mean, and D90 particle sizes of 222.24, 244, and 435 µm, respectively.

Formulations

Eight different aqueous nanosuspensions of salsalate, with differing surfactants or combinations of surfactants, were prepared and analyzed for particle size. The first 7 formulations were made by roller milling with a Roller-Mill RM20 (ZOZ GmbH) with YTZ-800 grinding media (Tosoh Corp.) at 192 rpm. The $8^{th}$ formulation was made via high speed media milling (5000 rpm). The particle sizes of the resultant compositions were then analyzed using a Horiba light scattering particle size analyzer. The compositions and results of the particle size analyses are shown below in Table 2 and in FIGS. 2A, 2B, 3A, 3B etc. through 9A and 9B.

TABLE 2

Figure 3:
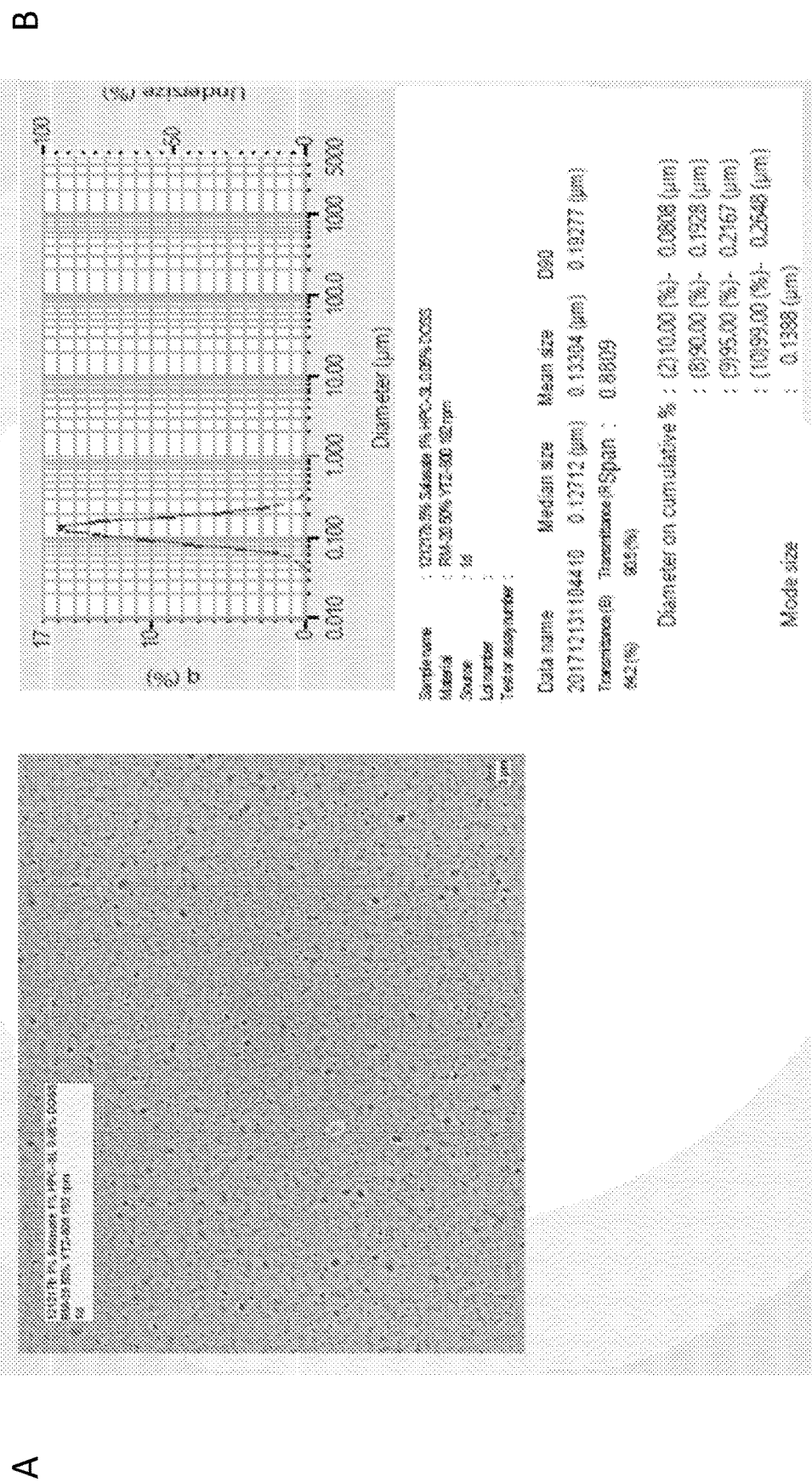
FIGS. 3A and B.
FIG. 3B shows the results of a particle size analysis using a Horiba light scattering particle size analyzer.
Figure 7:
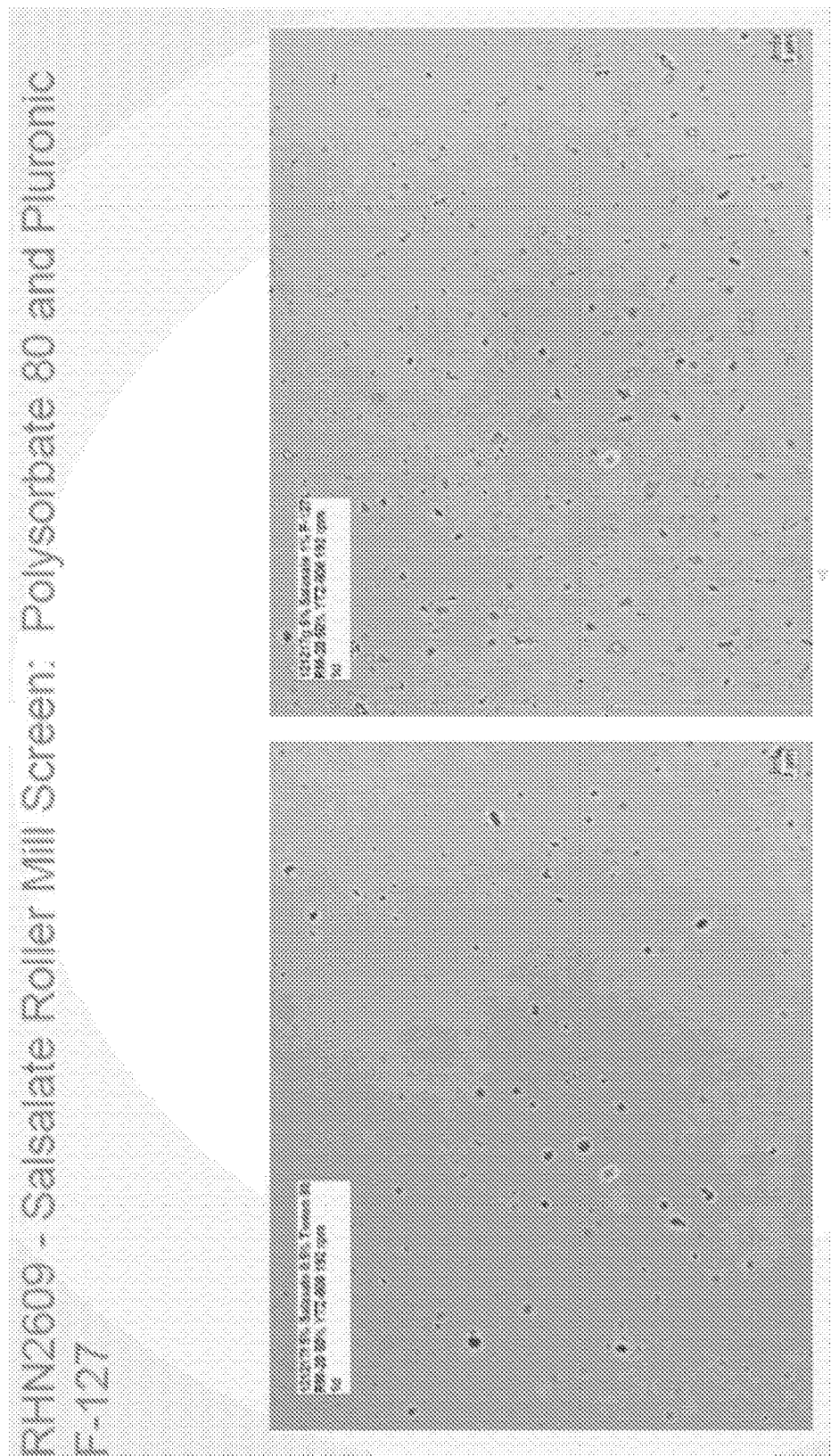
FIGS. 7A and B.
FIG. 7B shows an OM of an aqueous dispersion of 5% salsalate and 1% Pluronic F-127 following roller milling with a Roller-Mill RM20 with YTZ-800 grinding media.
Figure 10:
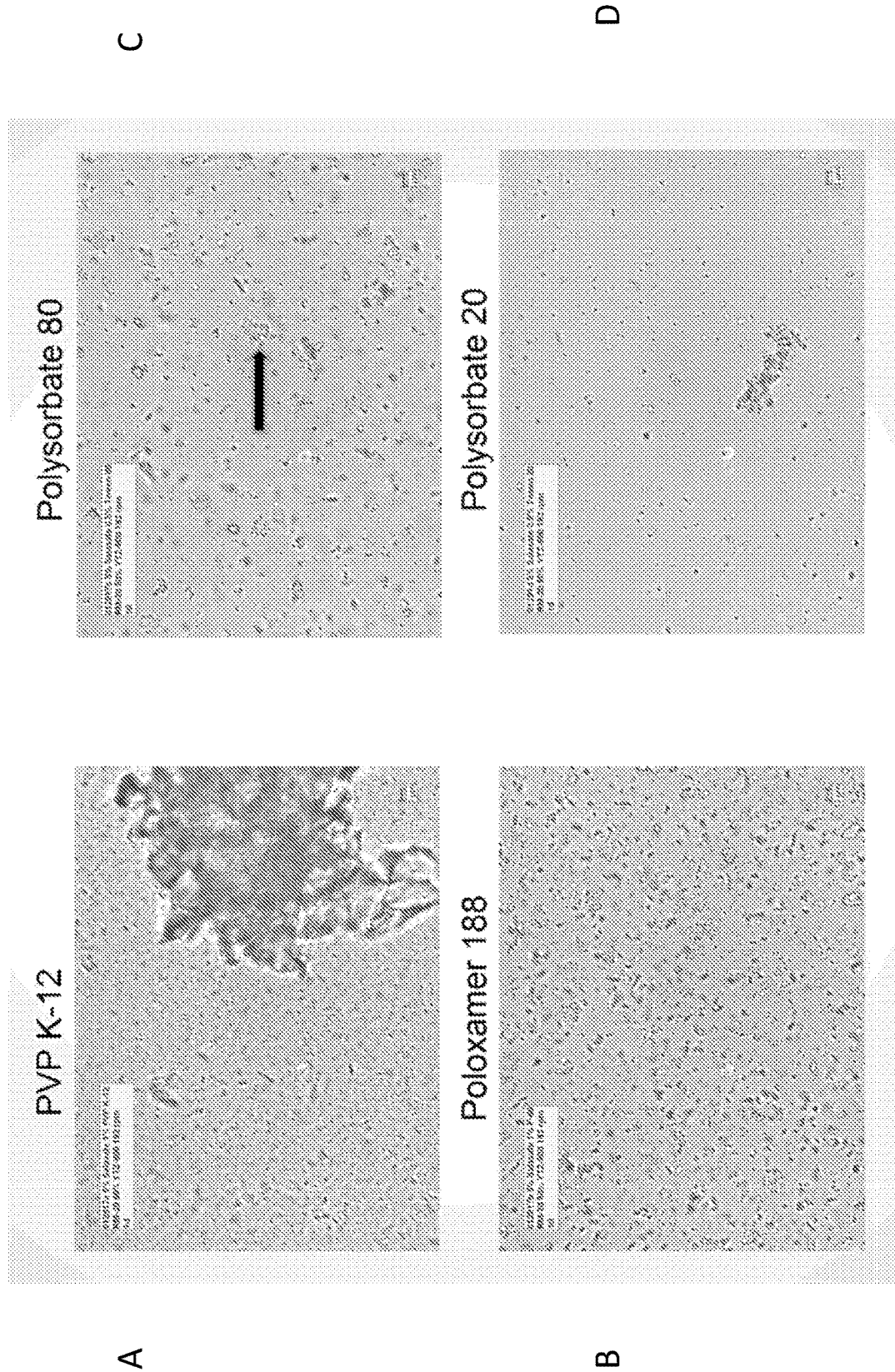
FIG. 10 shows an OM of an aqueous dispersion of 5% salsalate and 1% PVP K-12 (FIG. 10A); 5% salsalate and 1% Poloxamer 188 (Pluronic F-68) (FIG. 10B); 5% salsalate and 0.5% Tween 80 (FIG. 10C); and 5% salsalate and 0.5% Tween 20 (FIG. 10D), all following Roller Milling in an RM-20 Roller Mill with 50% YTZ-800 milling media at 192 rpm for 1 day.
Figure 11:
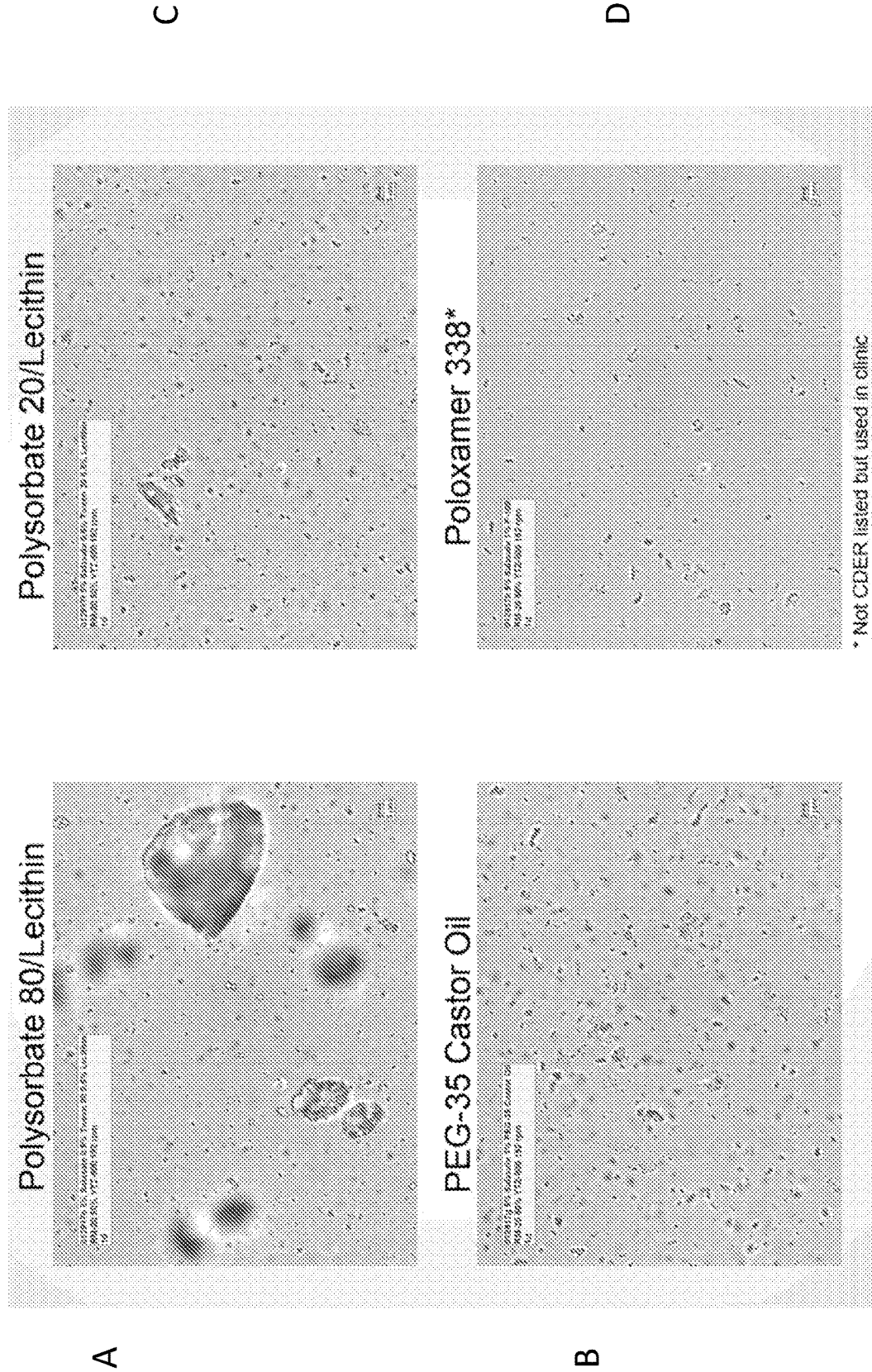
FIG. 11 shows an OM of an aqueous dispersion of 5% salsalate, 0.5% Tween 80, and 0.5% lecithin (FIG. 11A); 5% salsalate and 1% PEG-35 Castor Oil (FIG. 11B); 5% salsalate, 0.5% Tween 20, and 0.5% lecithin (FIG. 11C); and 5% salsalate and 1% Poloxamer 338 (Pluronic F-108) (FIG. 11D), all following Roller Milling in an RM-20 Roller Mill with 50% YTZ-800 milling media at 192 rpm for 1 day.
Figure 12C:
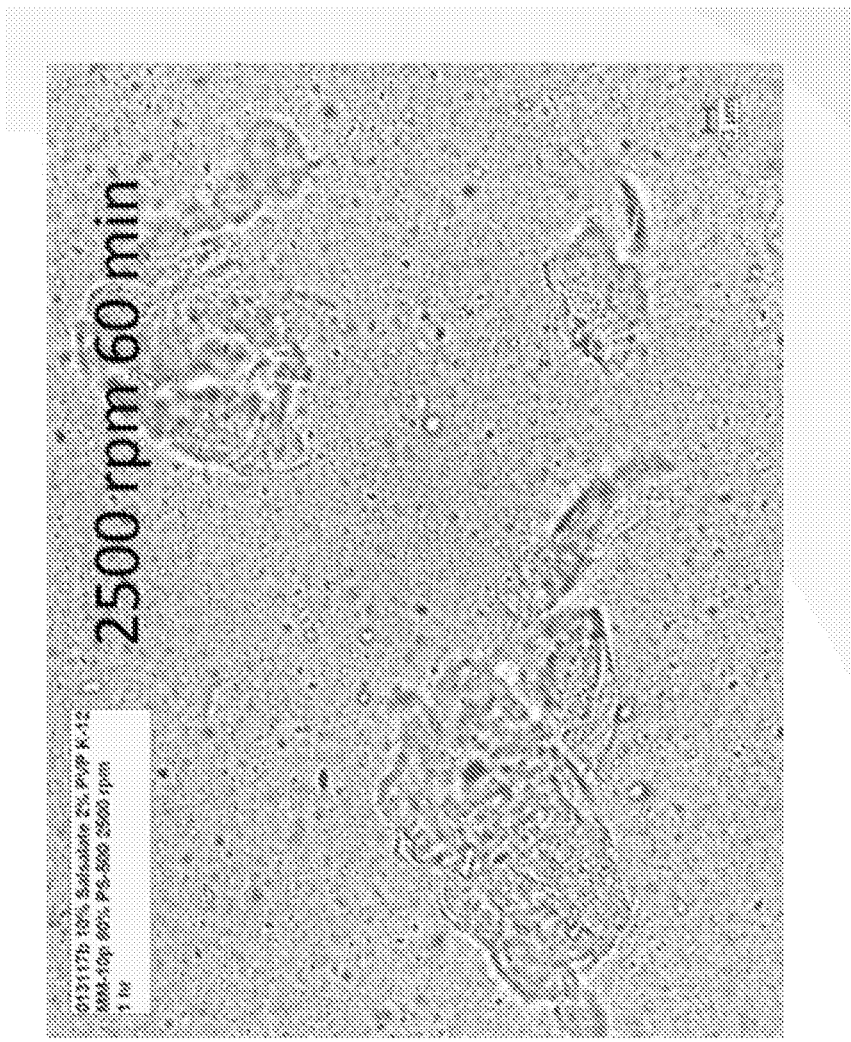
FIG. 12C shows an OM of an aqueous dispersion of 10% salsalate and 2% PVP K-12 following high speed milling in a MM-10p High Speed Media Mill, with 80% PS-500 media, at 2500 rpm, for 60 min.
Figure 13A:
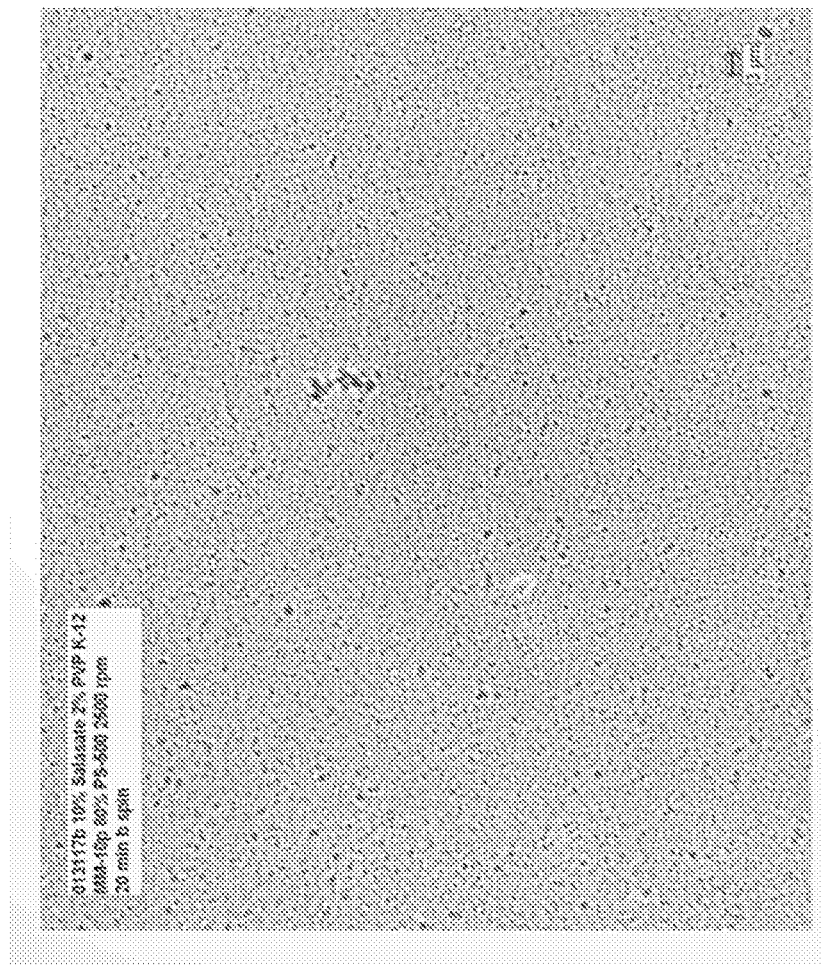
FIGS. 13A, B.
Figure 13B:
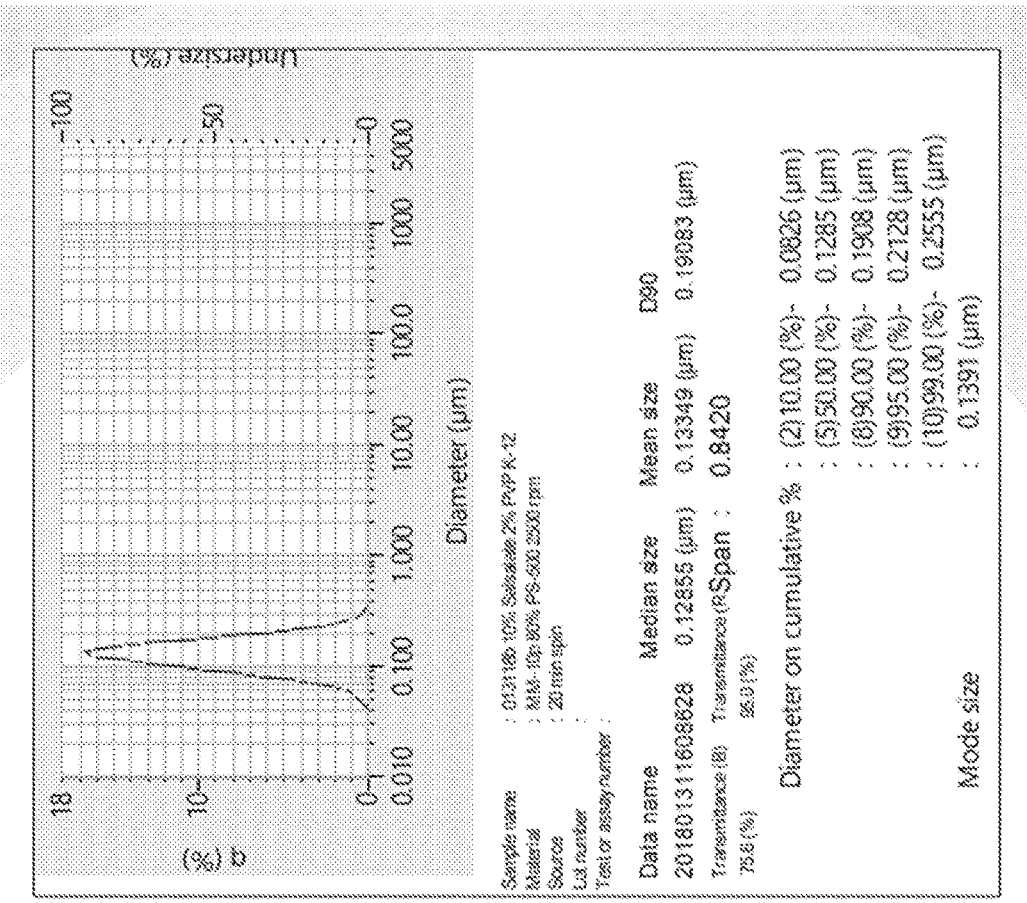
FIG. 13B shows the results of a particle size analysis.
Figure 14:
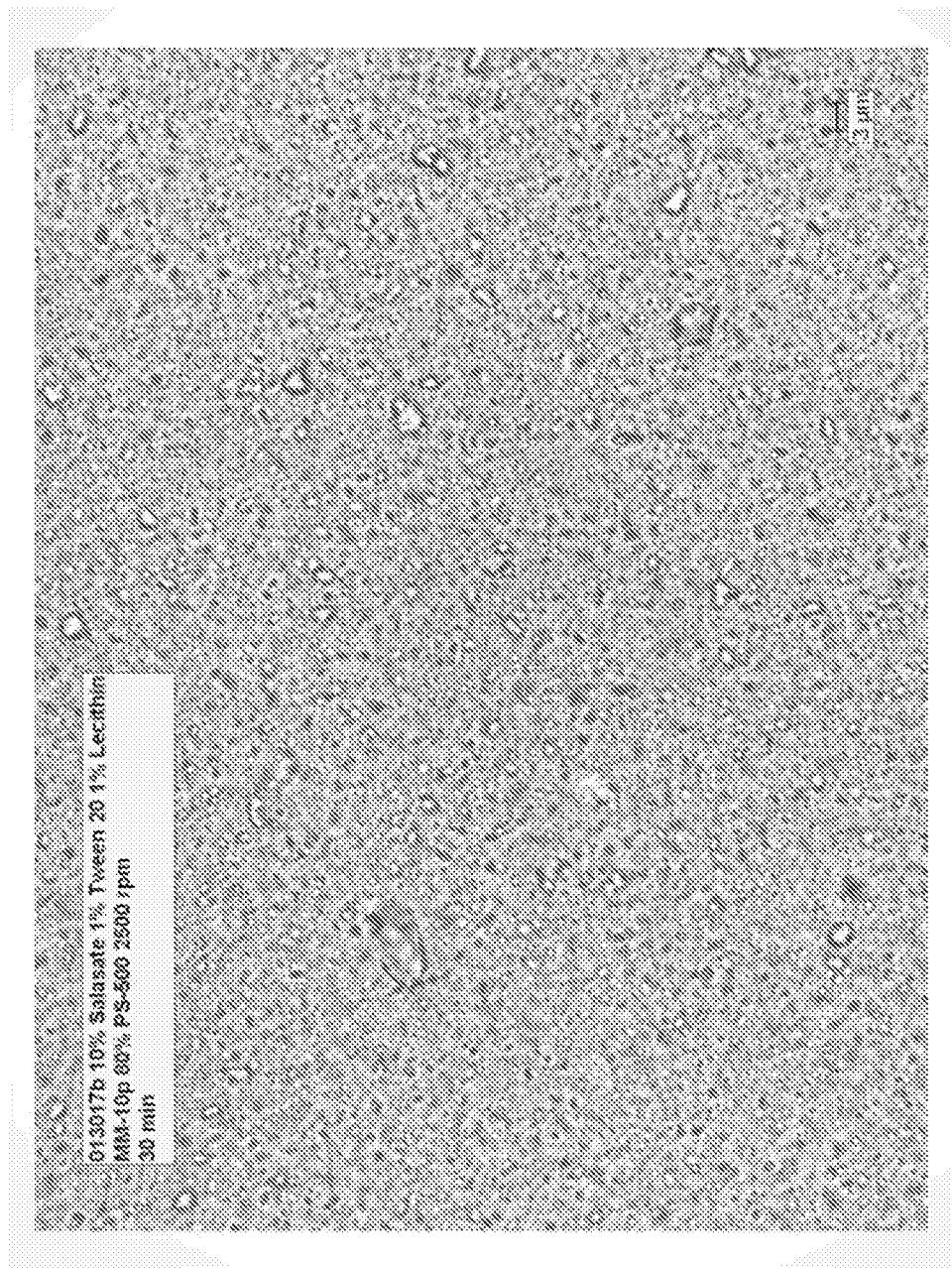
FIG. 14. Shows an OM of an aqueous dispersion of 10% salsalate, 1% Tween 20, and 1% lecithin following high speed media milling.

| FIG. | Formulation | Composition/Conditions | Process Conditions | Particle Sizes (μm) |
|---|---|---|---|---|
| FIGS. 2A, 2B | A | 5% Salsalate, 1% HPC-SL | RM-20 50% YTZ-800 192 rpm, 1 day | Median = 0.141 Mean = 0.177 D90 = 0.240 |
| FIGS. 3A, 3B | B | 5% Salsalate, 1% HPC-SL, 0.05% DOSS | RM-20 50% YTZ-800 192 rpm, 1 day | Median = 0.127 Mean = 0.133 D90 = 0.193 |
| FIGS. 4A, 4B | C | 5% Salsalate, 1% HPMC-606, 0.05% DOSS | RM-20 50% YTZ-800 192 rpm, 1 day | Median = 0.135 Mean = 0.142 D90 = 0.211 |
| FIGS. 5A, 5B | D | 5% Salsalate, 1% PVP K-30, 0.05% DOSS | RM-20 50% YTZ-800 192 rpm, 1 day | Median = 0.118 Mean = 0.123 D90 = 0.175 |
| FIGS. 6A, 6B | E | 5% Salsalate, 1% Plasdone S-630, 0.05% DOSS | RM-20 50% YTZ-800 192 rpm, 1 day | Median = 0.104 Mean = 0.109 D90 = 0.153 |
| FIG. 7A | F | 5% Salsalate, 0.5% Tween 80 | RM-20 50% YTZ-800 192 rpm, 1 day | Large aggregates visible on the OM |
| FIG. 7B | G | 5% Salsalate, 1% Pluronic F-127 | RM-20 50% YTZ-800 media, 192 rpm, 1 day | Large aggregates visible on the OM |
| FIGS. 8A, 8B | H | 5% Salsalate, 0.5% Tween 80 | RM-20 50% YTZ-800 192 rpm, 1 day | Median = 0.146 Mean = 0.244 D90 = 0.266 |
| FIGS. 9A, 9B | I | 15% Salsalate, 3% Plasdone S-630, 0.15% DOSS | MM-10p High Speed Media Mill, 80% PS-500 media, 5000 rpm, 1 hr | Median = 0.107 Mean = 0.112 D90 = 0.159 |

Results: The salsalate nanosuspension comprising Plasdone S-630 and DOSS as surfactants yielded a very fine, relatively homogenous nanocrystalline dispersion. Other salsalate nanodispersions were also successful, as detailed in Table 2. As depicted in FIGS. 6A and B, and 9A and 91B, the formulation is scalable from 5% (FIGS. 6A and B) to 15% (FIGS. 9A and B) with no apparent increase in particle size. The formulation may be milled using high speed media milling (FIGS. 9A and B). Further, the formulation had a very low viscosity, supporting the formulation of higher concentration nanosuspensions. The formulations have good drying characteristics.

Example 2

This example describes preparation of formulations of salsalate nanosuspensions.
Formulation Summary
A roller mill excipient screen was conducted with salsalate using standard IV Center for Drug Evaluation and Research ("CDER") listed inactive ingredients. See e.g., Table 3 below. The samples were analyzed using oil immersion photomicroscopy (OM). As shown in Table 4 below, none of the aqueous formulations formed totally acceptable dispersions in the Roller Mill screen. Milling with increased energy in a high speed milling process reduced the particle size, but over milling can result in agglomeration of the milled salsalate particles.

TABLE 3

CDER Listing IV Solutions

| Ingredient | Route | Dosage Form | Max Potency |
|---|---|---|---|
| Polysorbate 20 | intravenous | Injection | 4.8% |
| Polysorbate 20 | Intravenous | Powder, for injection solution | 0.044% |
| Polysorbate 20 | Intravenous | Solution, injection | 1% |
| Polysorbate 20 | IV (infusion) | Injectable | 0.003% |
| Polysorbate 20 | IV (infusion) | Injection | 2.4% |
| Polysorbate 20 | IV (infusion) | Powder, for injection solution | 0.023% |
| Polysorbate 20 | IV (infusion) | Solution, injection | 0.003% |
| Polyethylene glycol 400 | IM - IV | Injection | 20.3% |
| Polyethylene glycol 400 | IM- IV | Solution, injection | 18% |
| Polyethylene glycol 400 | Intravenous | injectable | 0.67 ml/ml |
| Polyethylene glycol 400 | Intravenous | injection | 11.25% |
| Polyethylene glycol 400 | intravenous | Solution, injection | 75.58% |
| Polyethylene glycol 400 | IV (infusion) | injection | 11.25% |

TABLE 4

| FIG. | Formulation | Composition | Process Conditions | Particle Sizes (μm) | Comments |
|---|---|---|---|---|---|
| 10A | J | 5% salsalate, 1% PVP K-12 | RM-20 50% YTZ-800 192 rpm, 1 day | n/a | Significant salsalate aggregates observed |
| 10B | K | 5% salsalate, 1% Poloxamer 188 (Pluronic F-68) | RM-20 50% YTZ-800 192 rpm, 1 day | n/a | Significant salsalate aggregates observed |

TABLE 4-continued

Figure 15A:
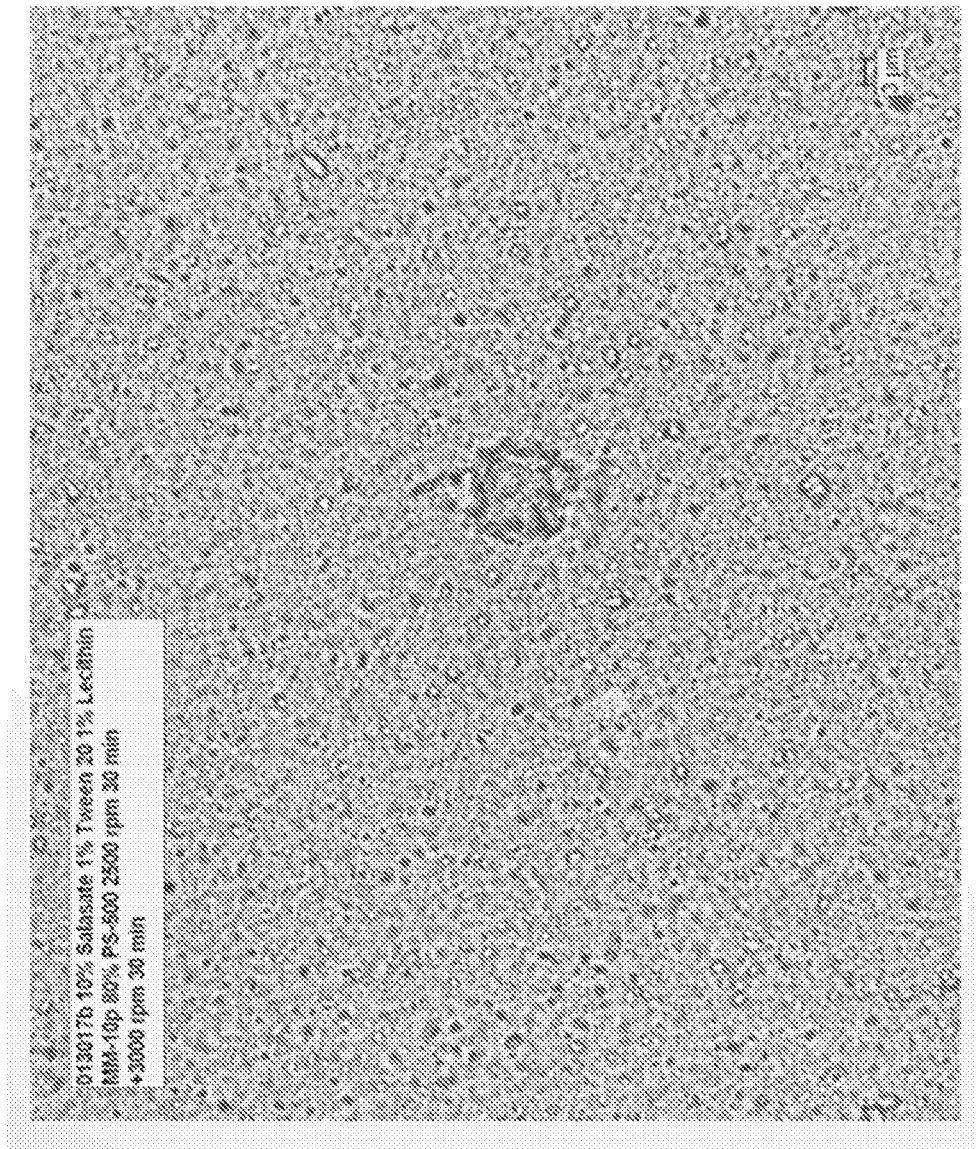
FIGS. 15A, B.
Figure 15B:
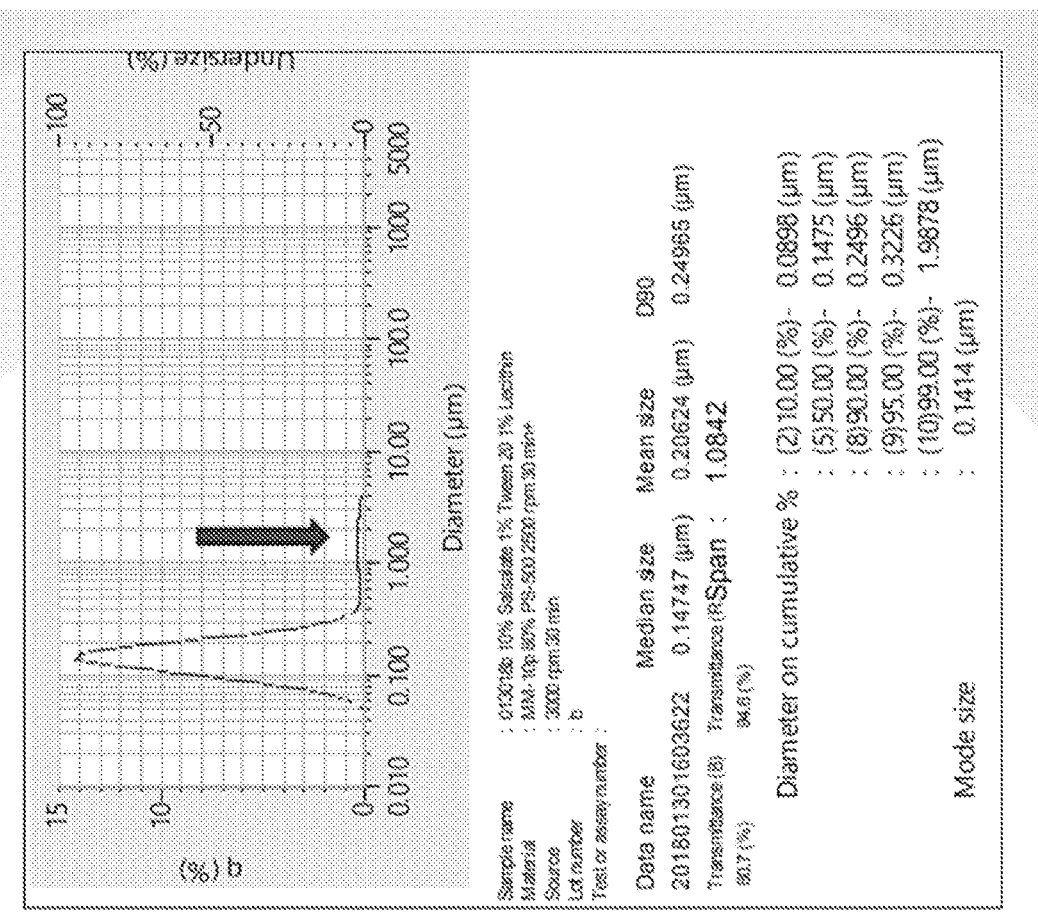
FIG. 15B shows the results of a particle size analysis.
Figure 16A:
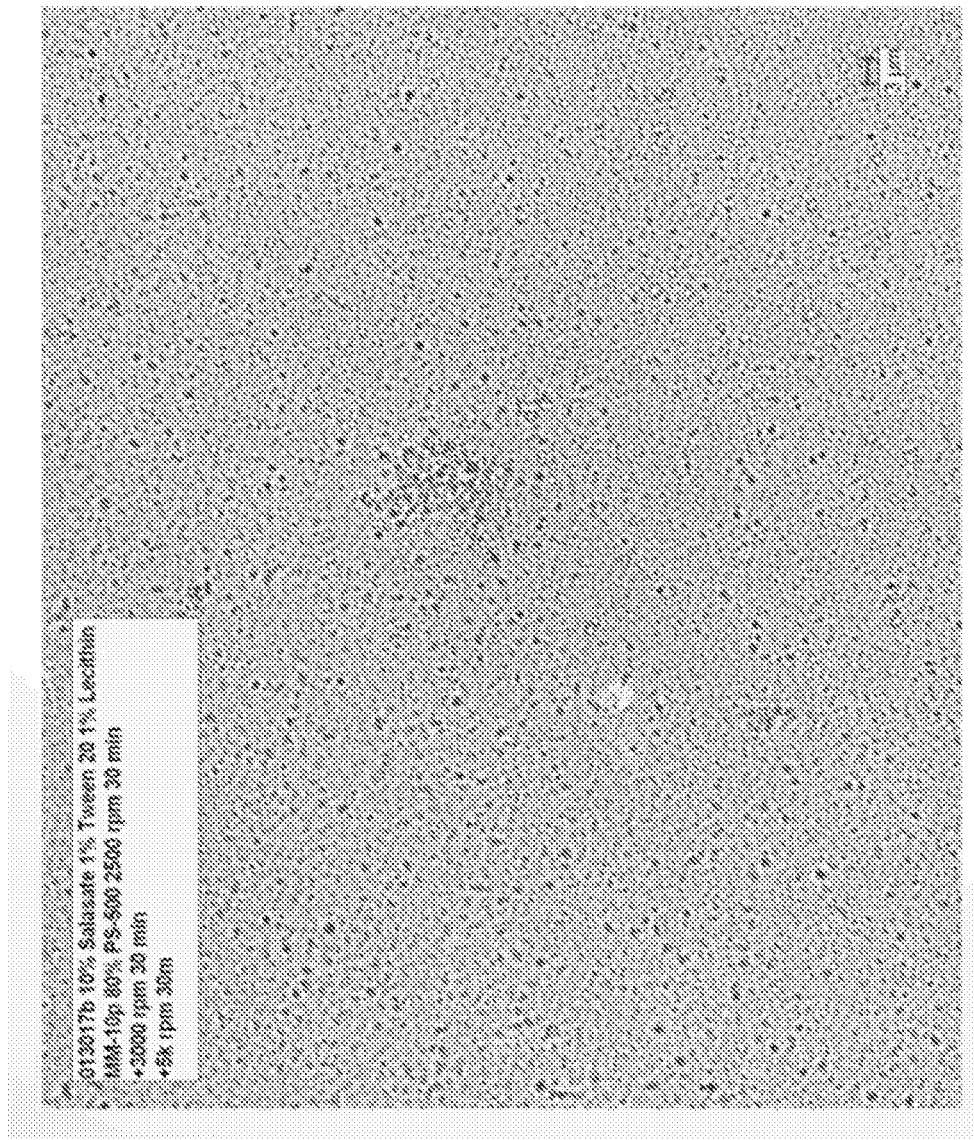
FIGS. 16A, B.
Figure 16B:
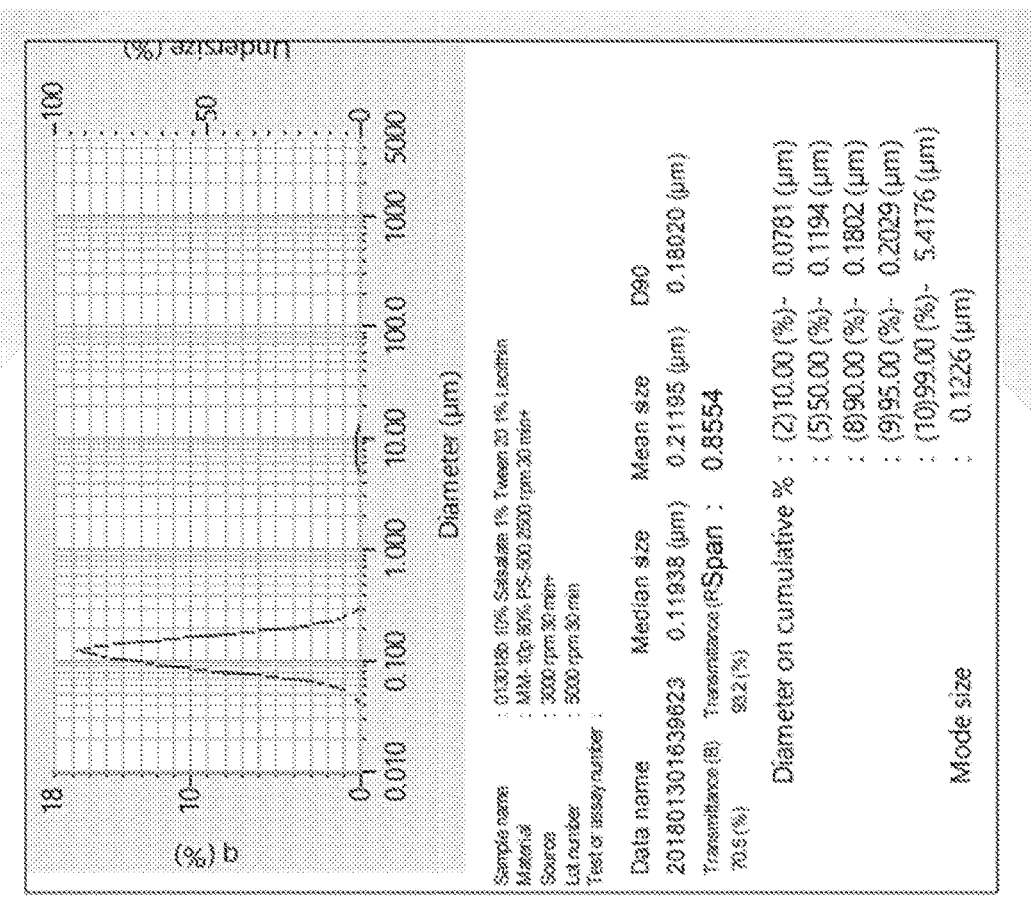
FIG. 16B shows the results of a particle size analysis.
Figure 17A:
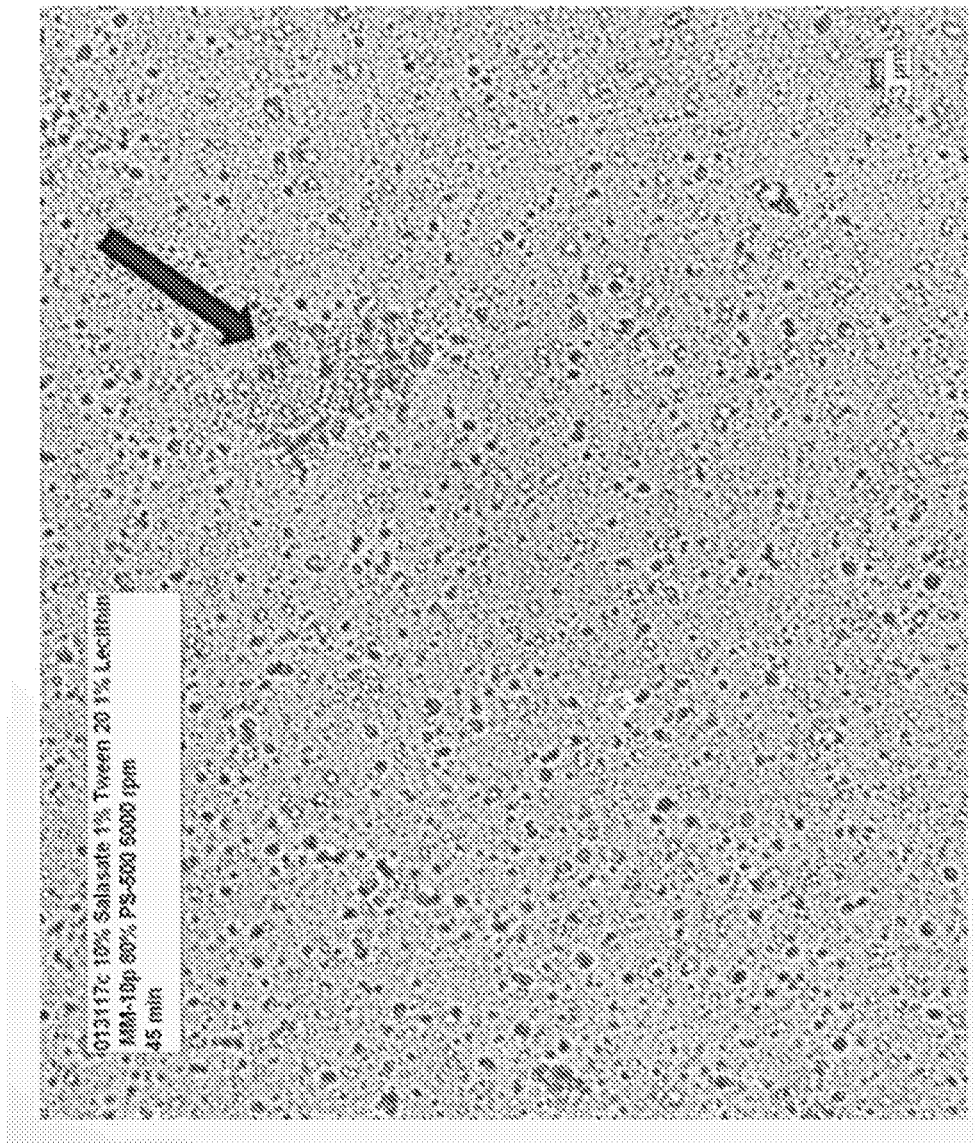
FIGS. 17A, B.
Figure 17B:
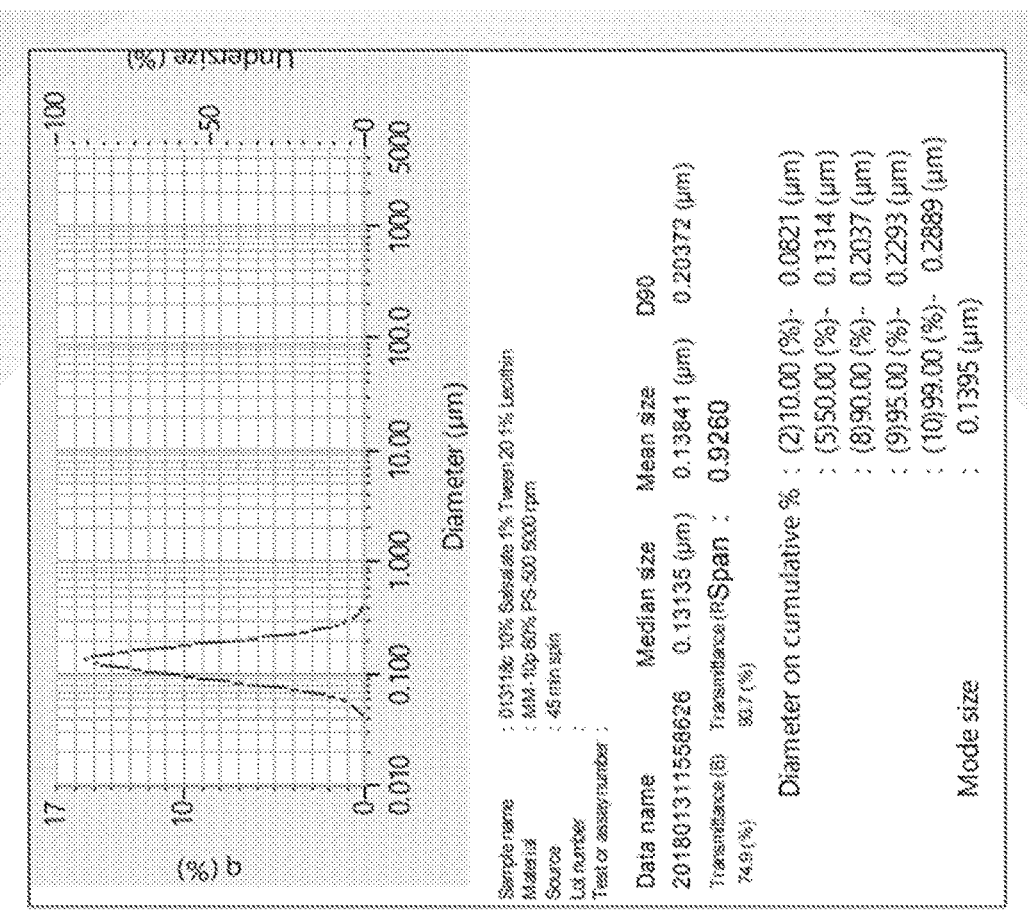
FIG. 17B shows the results of a particle size analysis.

| FIG. | Formulation | Composition | Process Conditions | Particle Sizes (μm) | Comments |
|---|---|---|---|---|---|
| 10C | L | 5% salsalate, 0.5% Tween 80 | RM-20 50% YTZ-800 192 rpm, 1 day | n/a | Significant salsalate aggregates observed |
| 10D | M | 5% salsalate, 0.5% Tween 20 | RM-20 50% YTZ-800 192 rpm, 1 day | n/a | Significant salsalate aggregates observed |
| 11A | N | 5% salsalate, 0.5% Tween 80, 0.5% lecithin | RM-20 50% YTZ-800 192 rpm, 1 day | n/a | Significant salsalate aggregates observed |
| 11B | O | 5% salsalate, 1% PEG-35 Castor Oil | RM-20 50% YTZ-800 192 rpm, 1 day | n/a | Significant salsalate aggregates observed |
| 11C | P | 5% salsalate, 0.5% Tween 20, 0.5% lecithin | RM-20 50% YTZ-800 192 rpm, 1 day | n/a | Significant salsalate aggregates observed |
| 11D | Q | 5% salsalate, 1% Poloxamer 338 (Pluronic F-108) | RM-20 50% YTZ-800 192 rpm, 1 day | n/a | Significant salsalate aggregates observed |
| 12A | R | 10% salsalate, 2% PVP K-12 | MM-10p High Speed Media Mill, 80% PS-500 media, 5000 rpm, 30 min spin | n/a | Salsalate particles agglomerated, likely from overmilling |
| 12B | S | 10% salsalate, 2% PVP K-12 | MM-10p High Speed Media Mill, 80% PS-500 media, 2500 rpm, 20 min spin | n/a | Better salsalate particle uniformity, but still some particle aggregation |
| 12C | T | 10% salsalate, 2% PVP K-12 | MM-10p High Speed Media Mill, 80% PS-500 media, 2500 rpm, 60 min spin | n/a | Significant salsalate particle aggregation |
| 13A, B | U | 10% salsalate, 2% PVP K-12 | MM-10p High Speed Media Mill, 80% PS-500 media, 2500 rpm, 20 min spin | Median = 0.128 Mean = 0.133 D90 = 0.191 | Following milling the composition was centrifuged to remove larger salsalate particulates. This produced a good nanosuspension, but the salsalate concentration was unknown and would have to be assayed |
| 14A, B | V | 10% salsalate, 1% Tween 20, 1% lecithin | MM-10p High Speed Media Mill, 80% PS-500 media, 2500 rpm, 30 min spin | n/a | Initial screen showed milling occurred though some larger salsalate particles observed |
| 15A, B | W | 10% Salsalate, 1% Tween 20, 1% lecithin | MM-10p High Speed Media Mill, 80% PS-500 media, 2500 rpm, 30 min spin; followed by 30 min at 3000 rpm | Median = 0.147 Mean = 0.206 D90 = 0.250 | Most salsalate parttices in the nano range, but some particles still at about 1 micron (see the arrow on FIG. 15B) |
| 16A, B | X | 10% salsalate, 1% Tween 20, 1% lecithin | MM-10p High Speed Media Mill, 80% PS-500 media, 2500 rpm, 30 min spin; followed by 30 min at 3000 rpm, followed by 5000 rpm for 30 min | Median = 0.119 Mean = 0.212 D90 = 0.180 | Milling for an additional 30 min at 5000 rpm resolved the salsalate particle peak at ~1 micron, although a salsalate particle population was observed at ~10 microns, likely due to agglomeration from overmilling |
| 17A, B | Y | 10% salsalate, 1% Tween 20, 1% lecithin | MM-10p High Speed Media Mill, 80% PS-500 media, 5000 rpm, 45 min spin | Median = 0.131 Mean = 0.138 D90 = 0.204 | Milling for 45 min at 5000 rpm resulted in most salsalate particles in the nano range, although some agglomerates are seen in the optical micrograph (FIG. 17A). The sample was then centrifuged to remove this material. |
| 18A, B | Z | 10% salsalate, 1% Tween 80, 1% lecithin | MM-10p High Speed Media Mill, 80% PS-500 media, 5000 rpm, | Median = 0.118 Mean = 0.156 D90 = 0.183 | Milling for 60 min at 5000 rpm resulted in most salsalate particles in the nano range, although a |

TABLE 4-continued

Figure 18A:
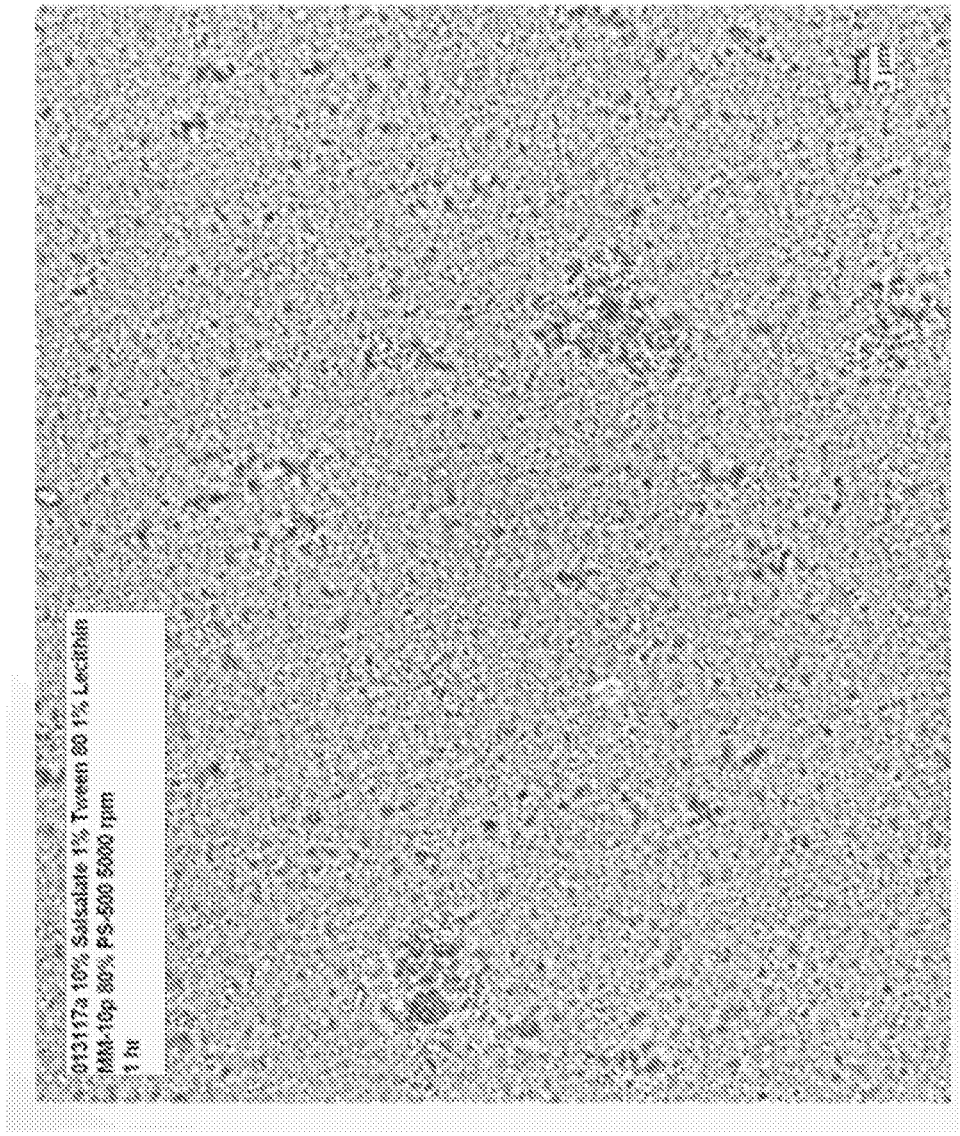
FIGS. 18A, B.
Figure 18B:
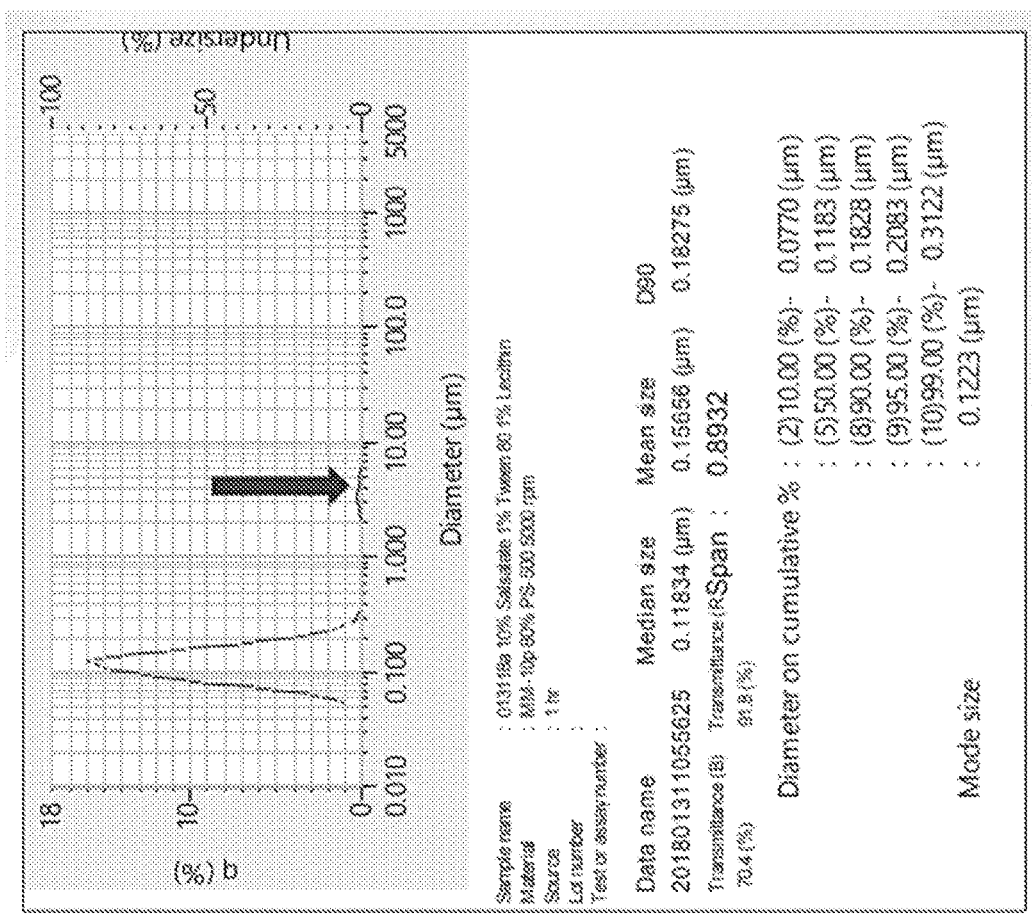
FIG. 18B shows the results of a particle size analysis.
Figure 19A:
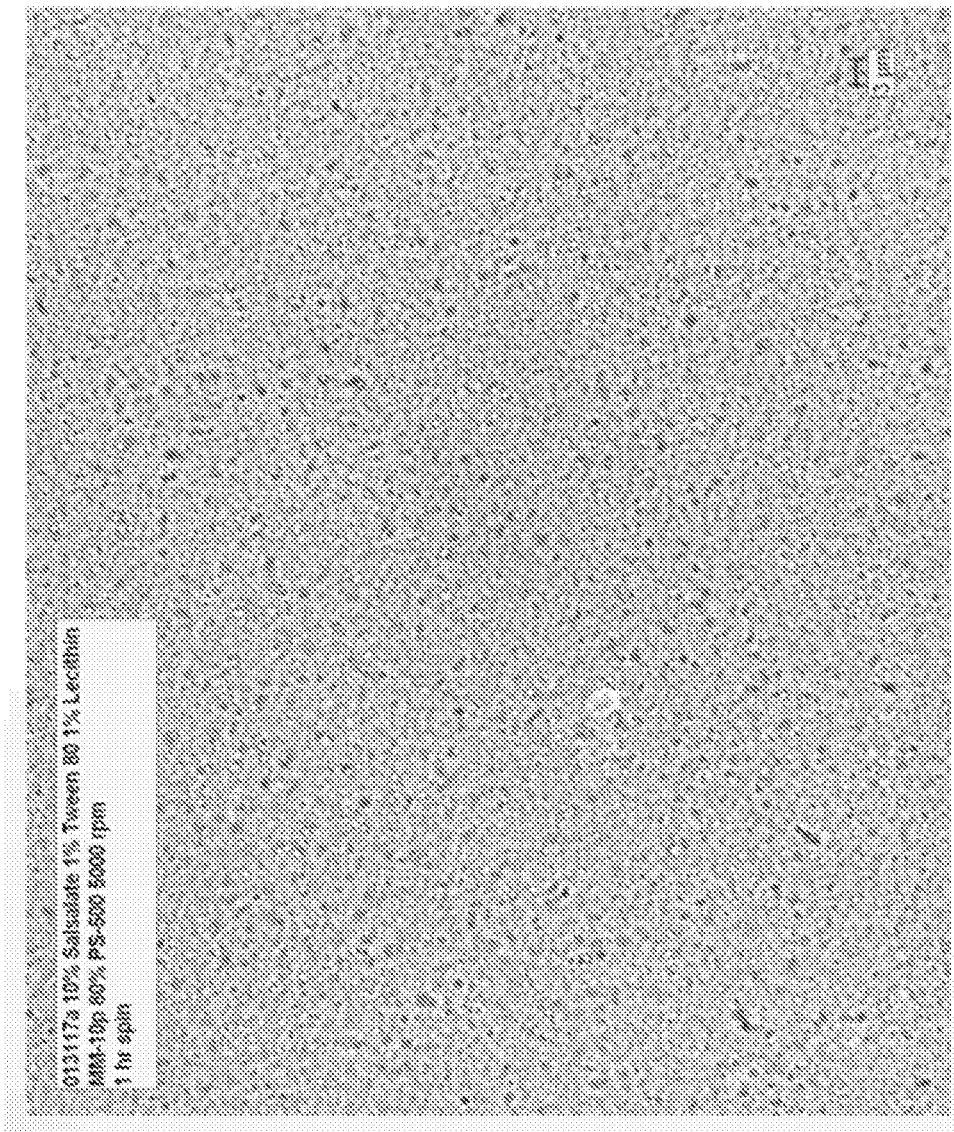
FIGS. 19A, B.
Figure 19B:
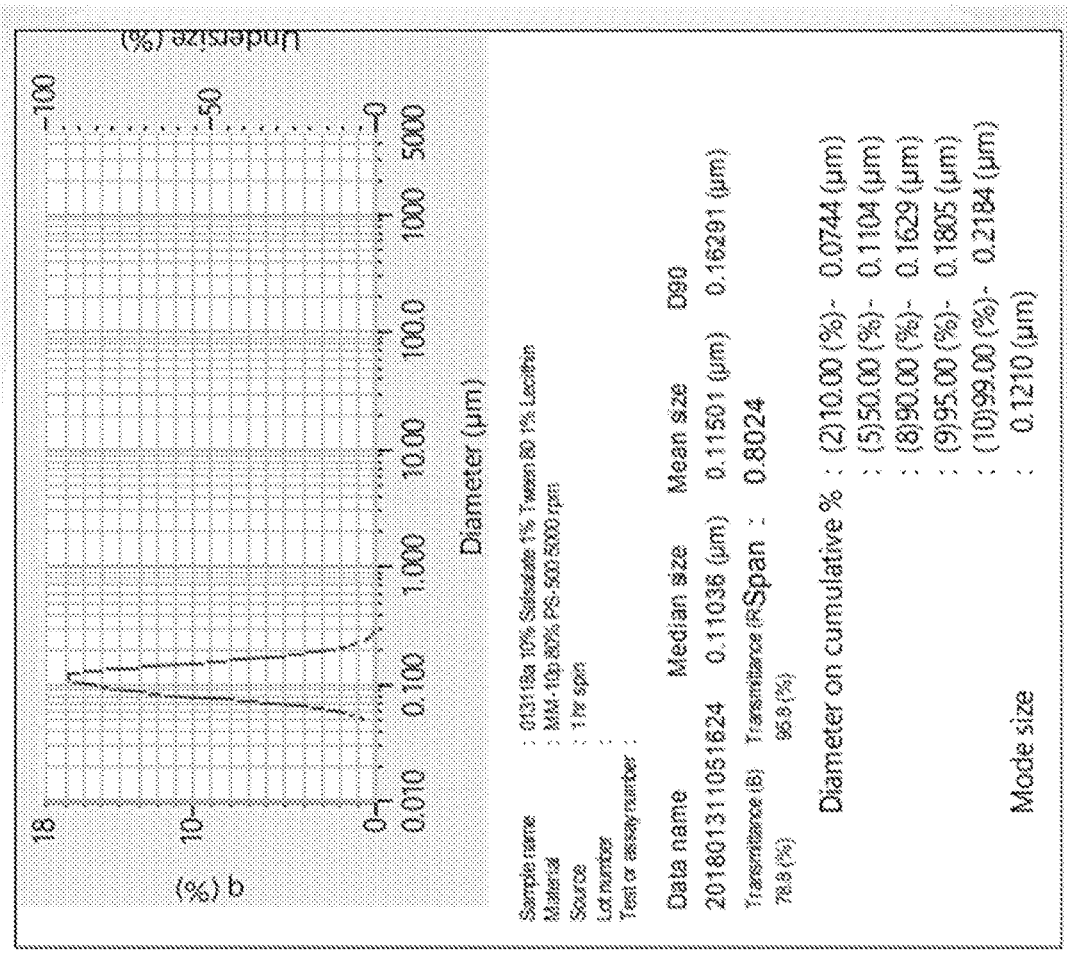
FIG. 19B shows the results of a particle size analysis.
Figure 20:
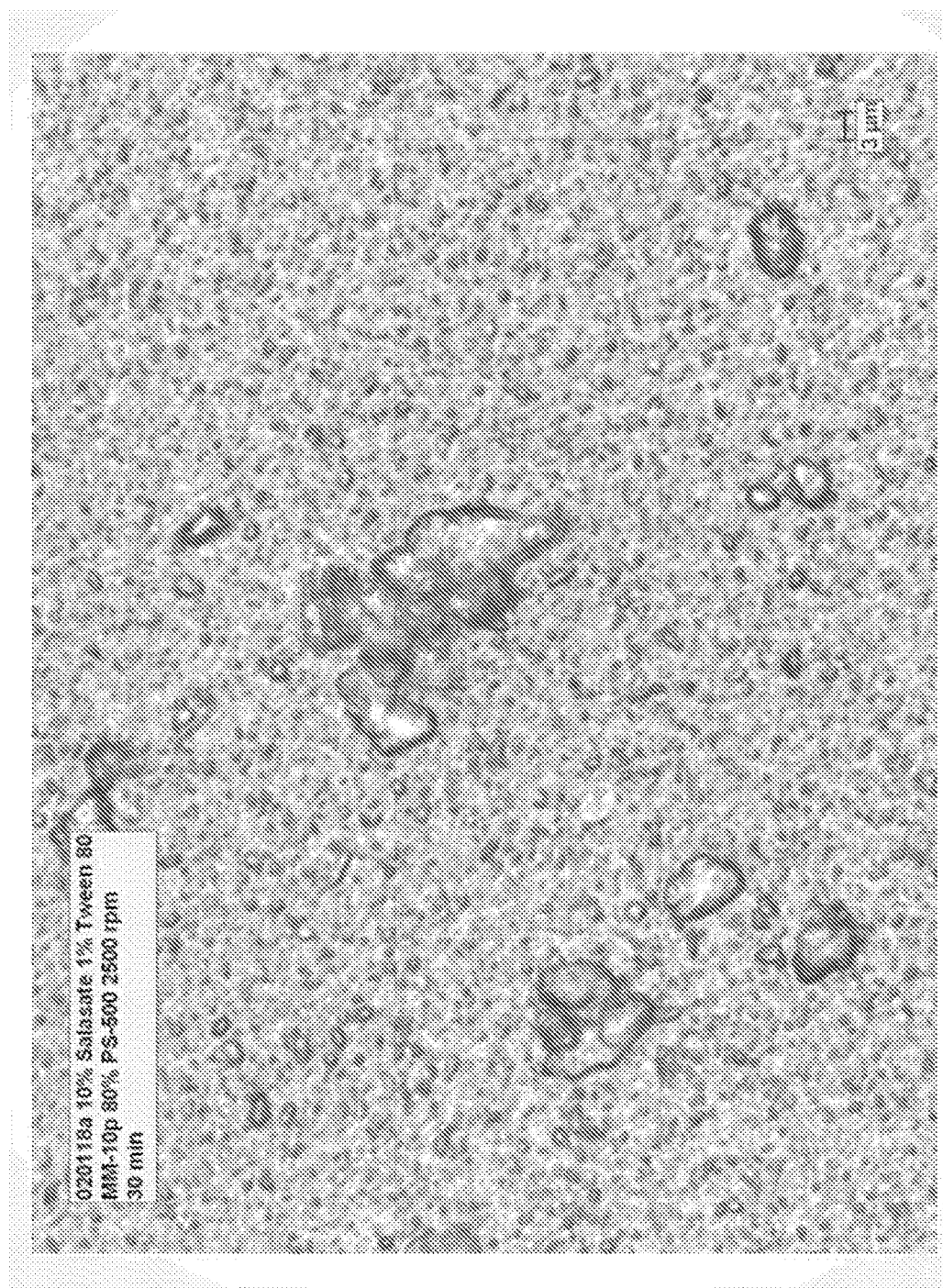
FIG. 20.
Figure 21A:
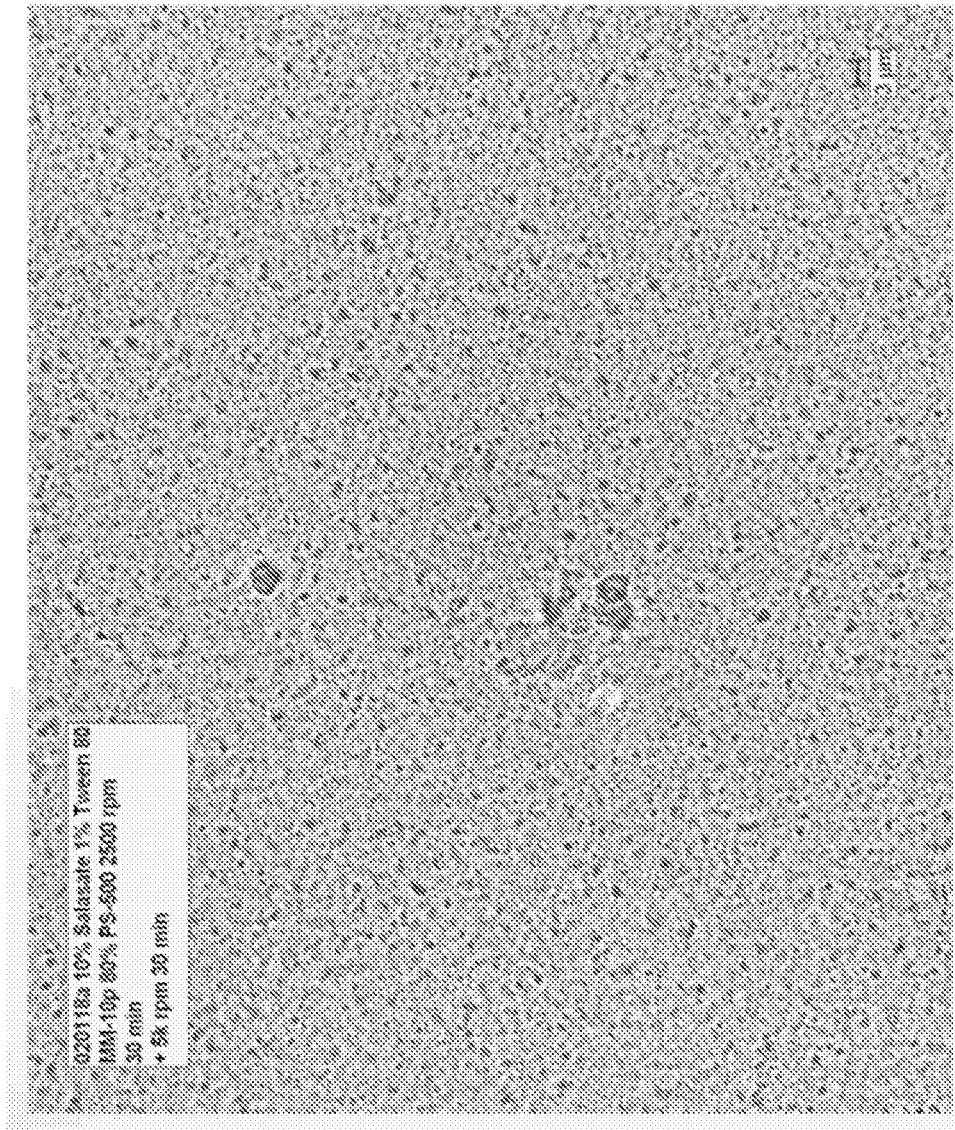
FIGS. 21A, B.
Figure 21B:
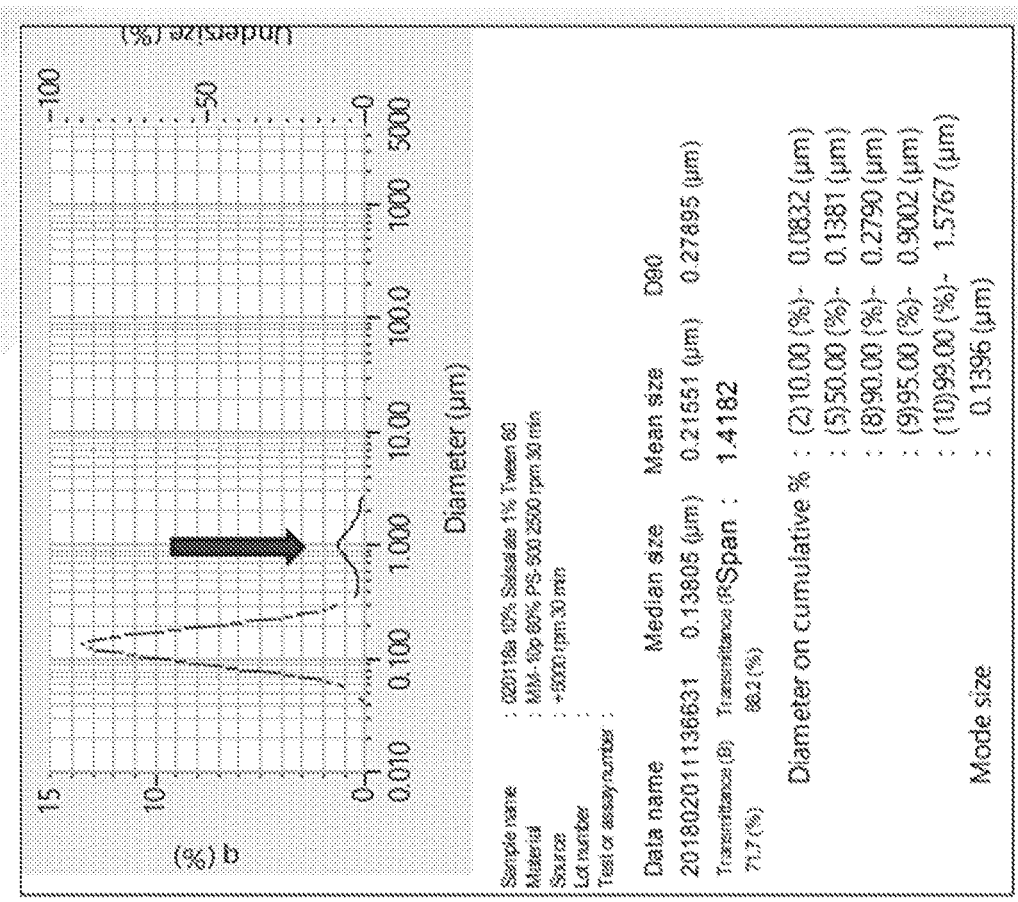
FIG. 21B shows the results of a particle size analysis.
Figure 22A:
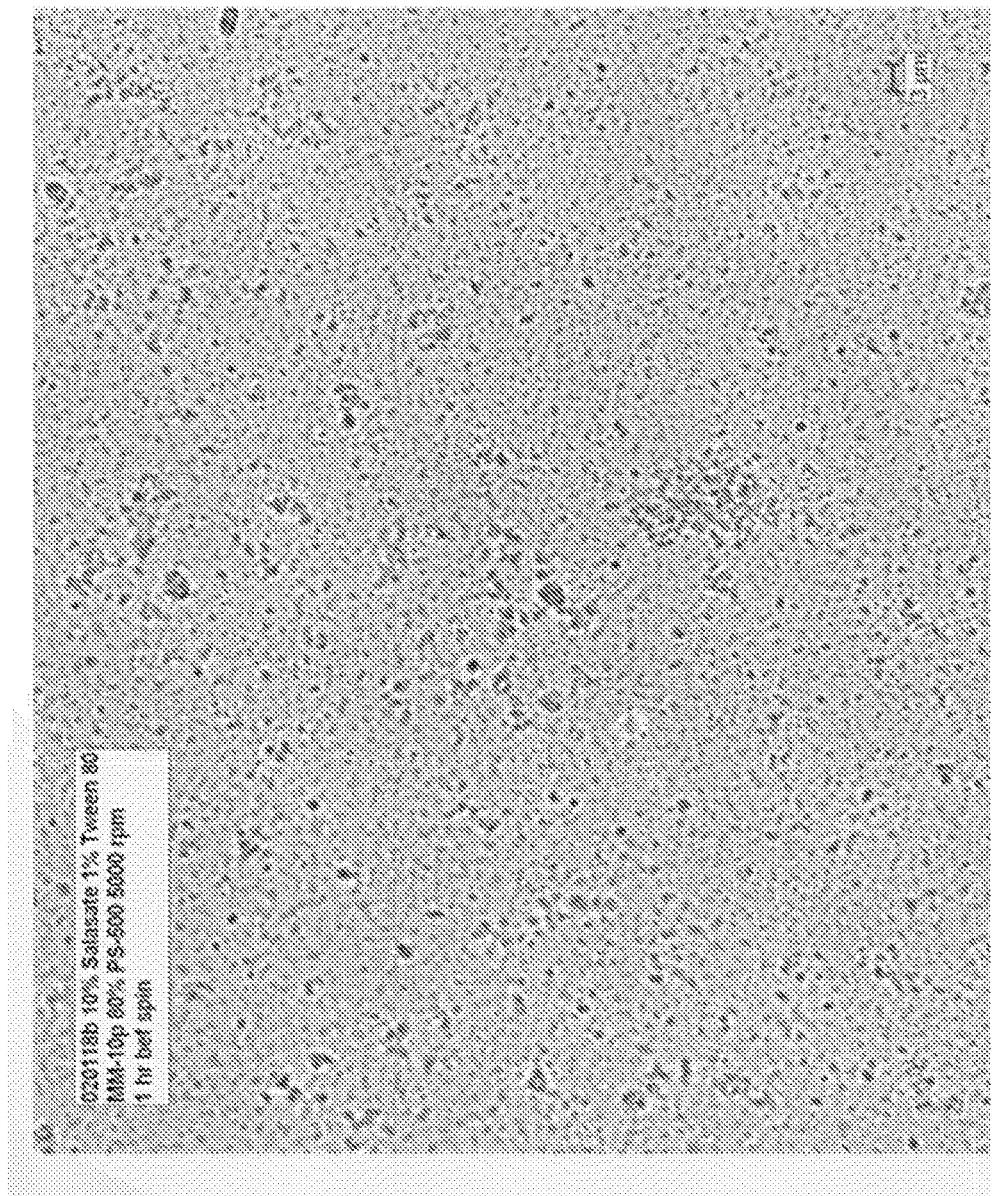
FIGS. 22A, B.
Figure 22B:
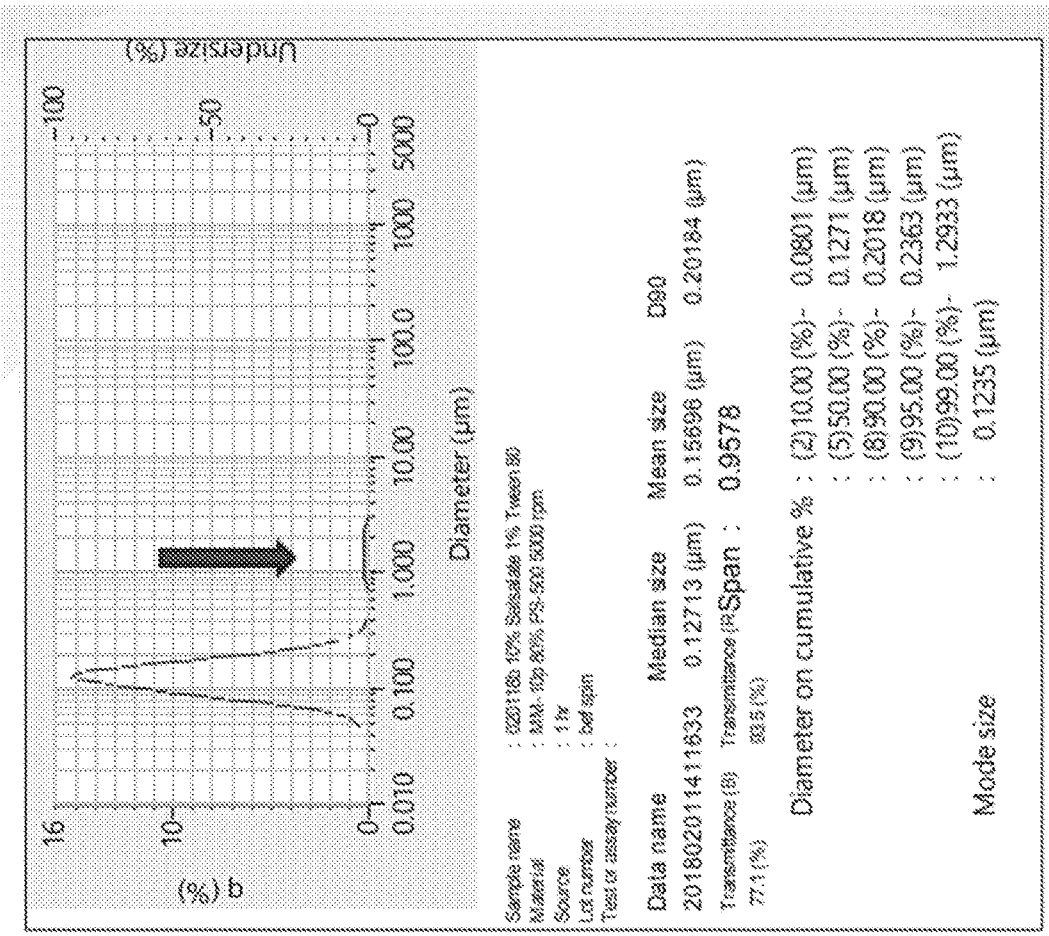
FIG. 22B shows the results of a particle size analysis.
Figure 23A:
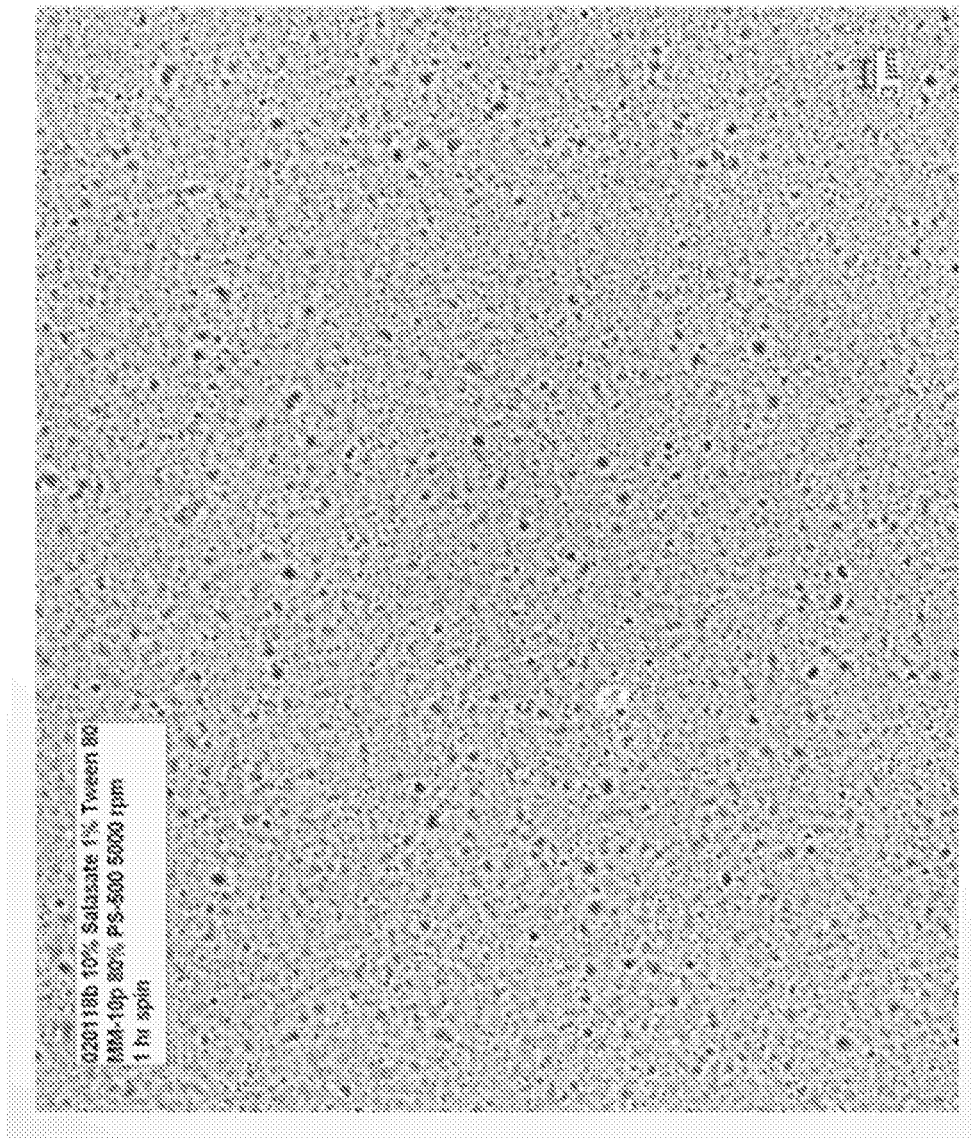
FIGS. 23A, B.
Figure 23B:
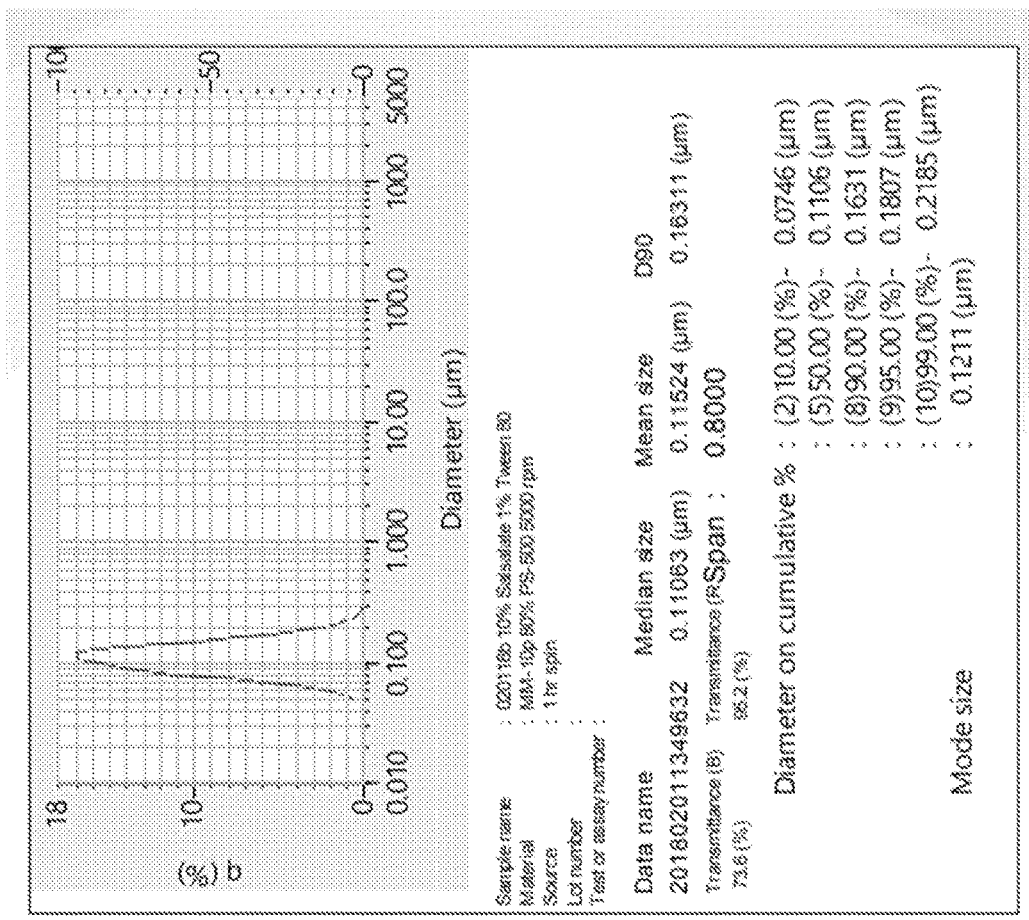
FIG. 23B shows the results of a particle size analysis.

| FIG. | Formulation | Composition | Process Conditions | Particle Sizes (μm) | Comments |
|---|---|---|---|---|---|
| | | | 1 hr spin | | population of salsalate particles existed at 1-10 microns (see the arrow on FIG. 18B) |
| 19A, B | AA | 10% salsalate, 1% Tween 80, 1% lecithin | MM-10p High Speed Media Mill, 80% PS-500 media, 5000 rpm, 1 hr spin | Median = 0.110 Mean = 0.115 D90 = 0.163 | Larger salsalate particles (FIG. 19A) can be removed by centrifugation resulting in a clean salsalate nanosuspension. |
| 20 | BB | 10% salsalate, 1% Tween 80 | MM-10p High Speed Media Mill, 80% PS-500 media, 2500 rpm, 30 min spin | n/a | Initial screen showed milling occurring though some larger salsalate particles were observed (FIG. 20) |
| 21A, B | CC | 10% salsalate, 1% Tween 80 | MM-10p High Speed Media Mill, 80% PS-500 media, 2500 rpm, 30 min spin, followed by 5000 rpm for 30 min spin | Median = 0.138 Mean = 0.215 D90 = 0.279 | Most salsalate particles were milled into the nano range, although a population of salsalate particles existed at ~1 micron (see the arrow on FIG. 21B) |
| 22A, B | DD | 10% salsalate, 1% Tween 80 | MM-10p High Speed Media Mill, 80% PS-500 media, 5000 rpm, 1 hr | Median = 0.127 Mean = 0.157 D90 = 0.202 | Most salsalate particles were milled into the nano range, although a population of salsalate particles existed at ~1 micron (see the arrow on FIG. 22B) |
| 23A, B | EE | 10% salsalate, 1% Tween 80 | MM-10p High Speed Media Mill, 80% PS-500 media, 5000 rpm, 1 hr spin | Median = 0.110 Mean = 0.115 D90 = 0.163 | Larger salsalate particles shown in FIG. 23A can be removed by centrifugation |

The data shown in Table 4 demonstrates that low energy milling is insufficient for preparing an acceptable salsalate nanodispersion with the tested IV-suitable CDER surfactants. However, high energy milling produces salsalate nanodispersions that have a low percentage of extraneous salsalate particle clusters, and therefore are successful salsalate nanodispersions.

Example 3

This example describes preparation of formulations of salsalate nanosuspensions.

Formulations

Aqueous nanosuspensions comprising 10% salsalate and 1% Tween 80 as a surfactant were prepared and analyzed for particle size before and after centrifugation and/or storage at 5° C. The formulations were made via high speed media milling (5000 rpm) in PS-500 media. The particle sizes of the resultant compositions were then analyzed using oil immersion photo microscopy and a Horiba light scattering particle size analyzer. The compositions and results of the particle size analyses are shown below in Table 5 and in FIGS. 33A, 33B, 34A, 34B, 35A, 35B, 36A, 36B, 37A, and 37B.

TABLE 5

Figure 33A:
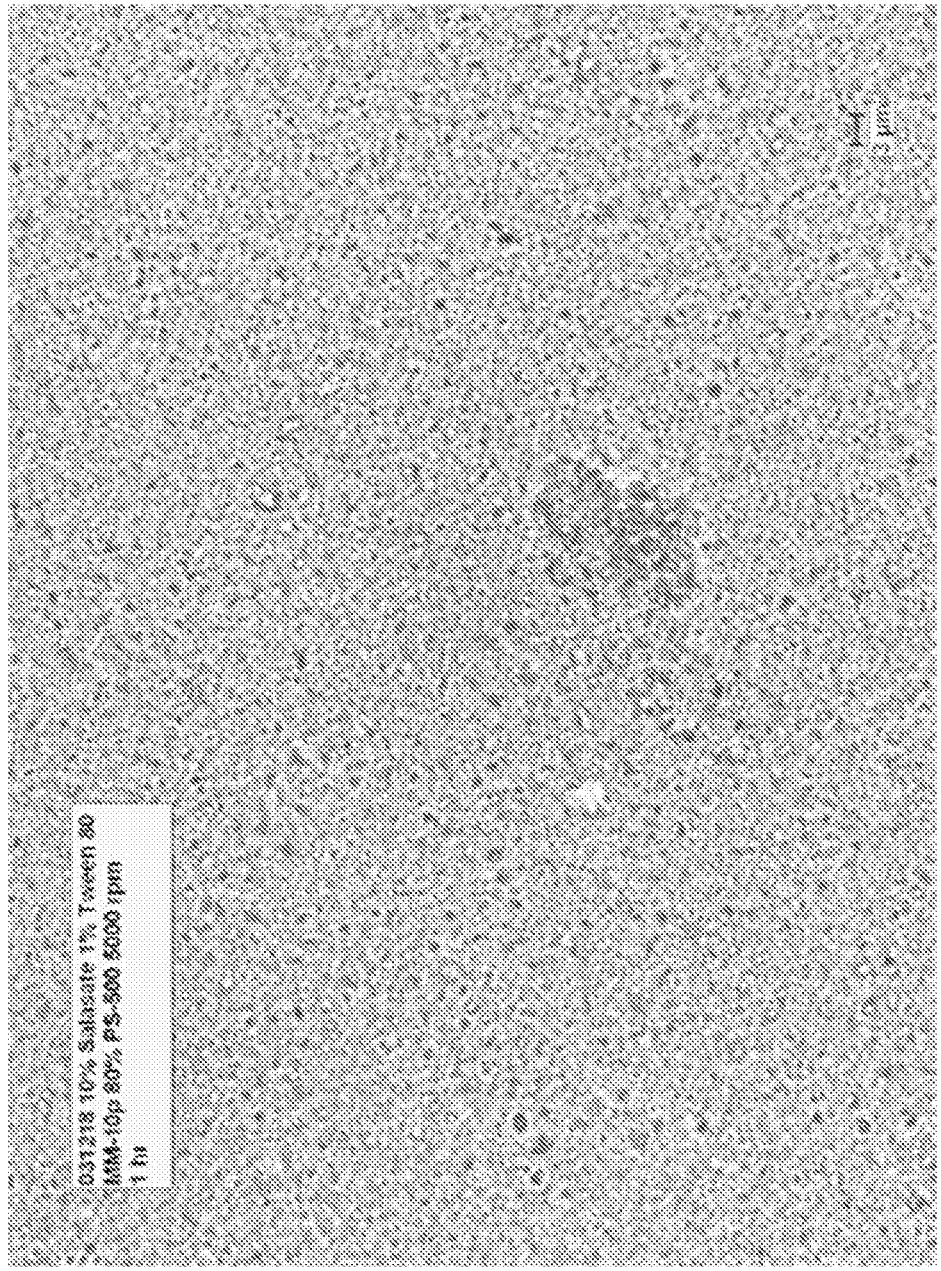
FIGS. 33A, B.
Figure 33B:
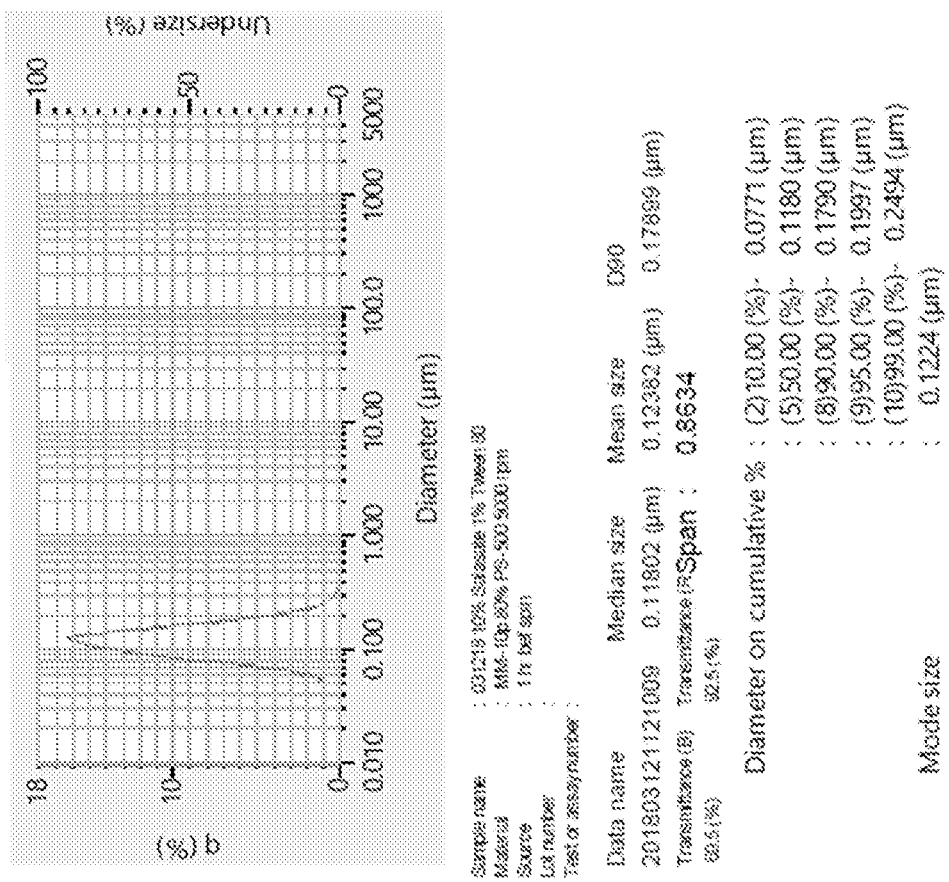
FIG. 33B shows the results of a particle size analysis.
Figure 34A:
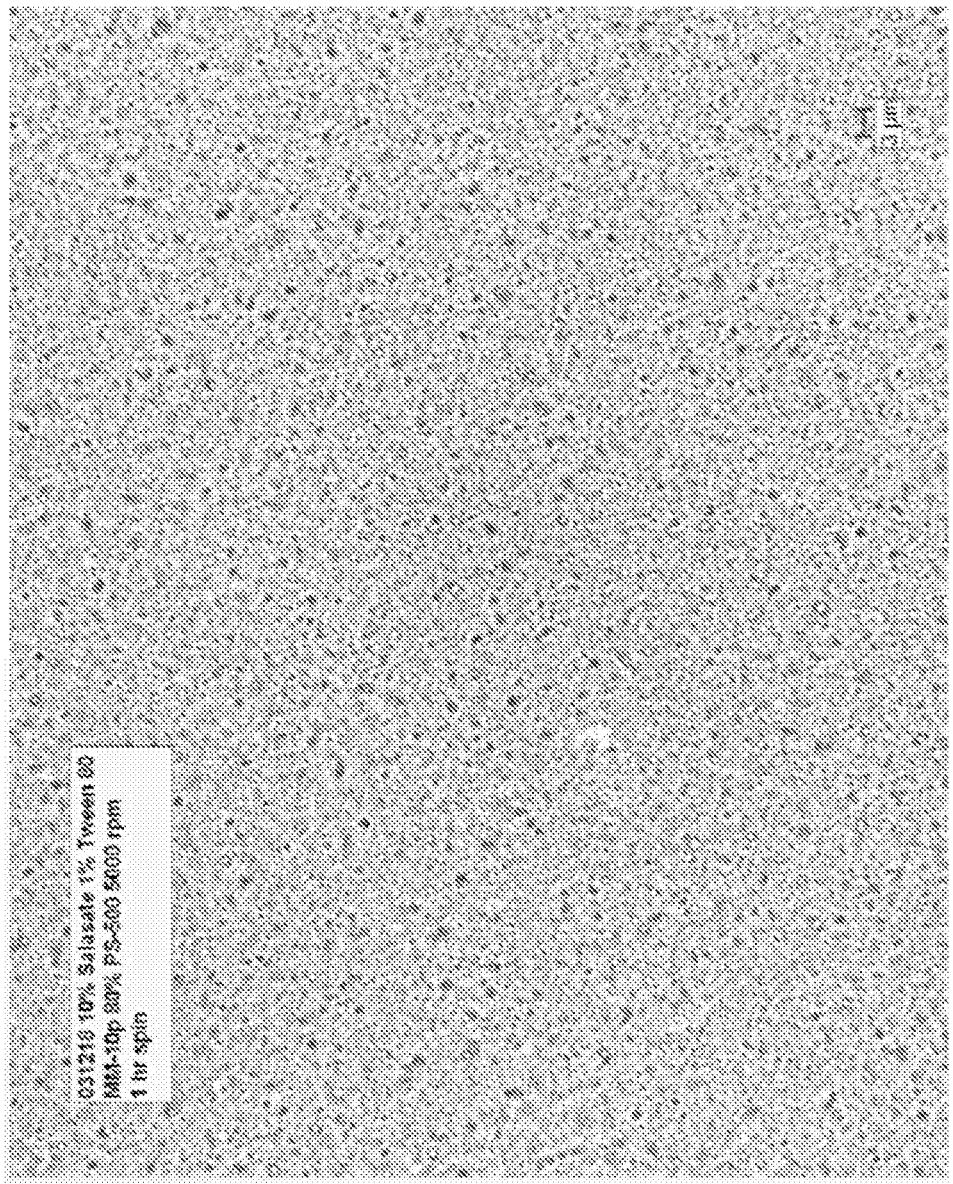
FIGS. 34A, B.
Figure 34B:
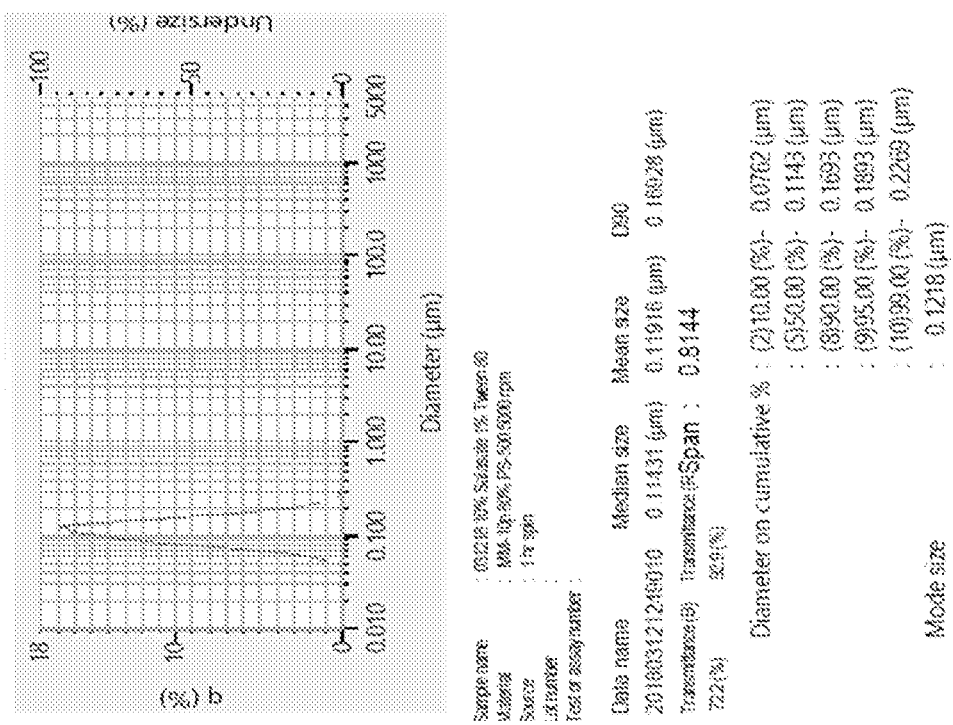
FIG. 34B shows the results of a particle size analysis.
Figure 35A:
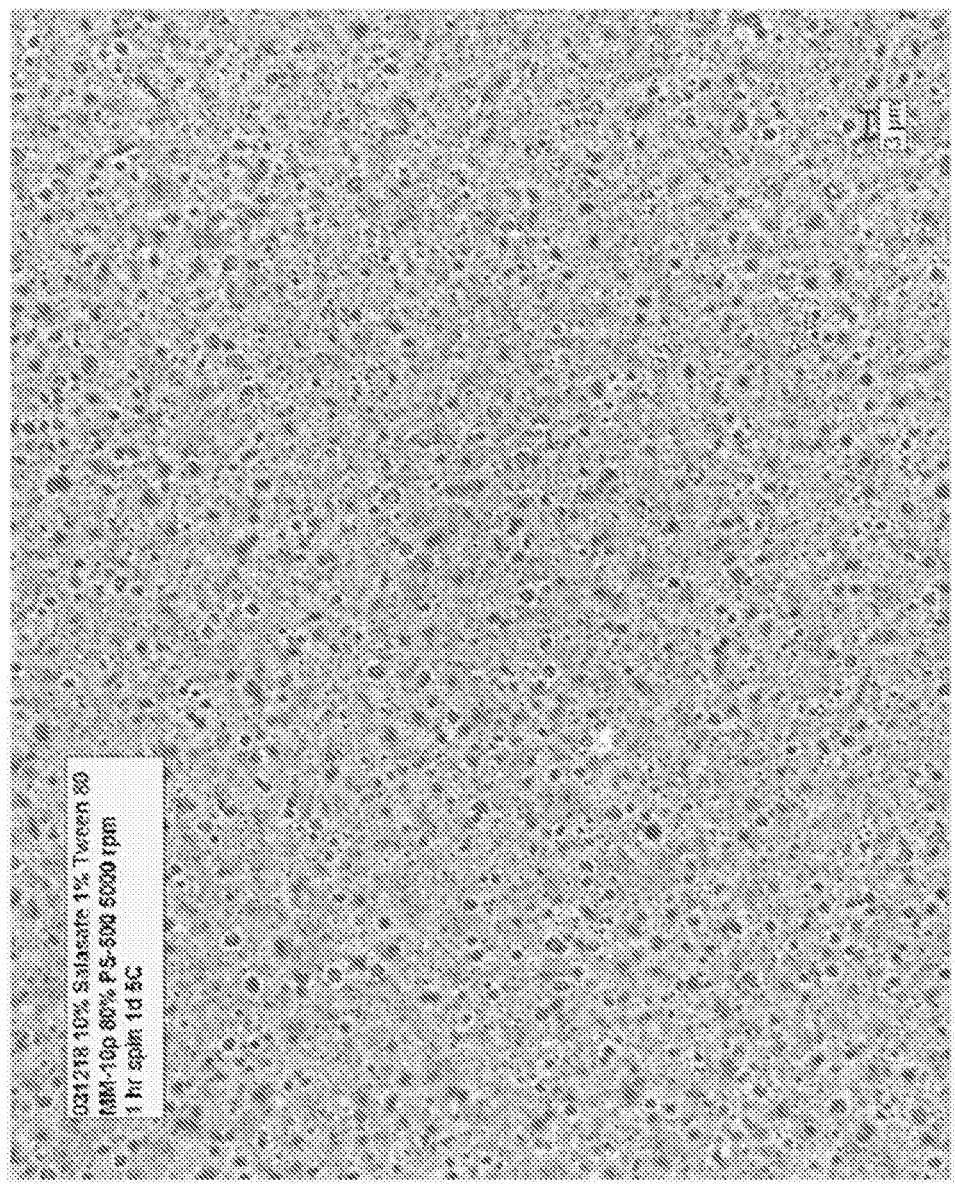
FIGS. 35A, B.
Figure 35B:
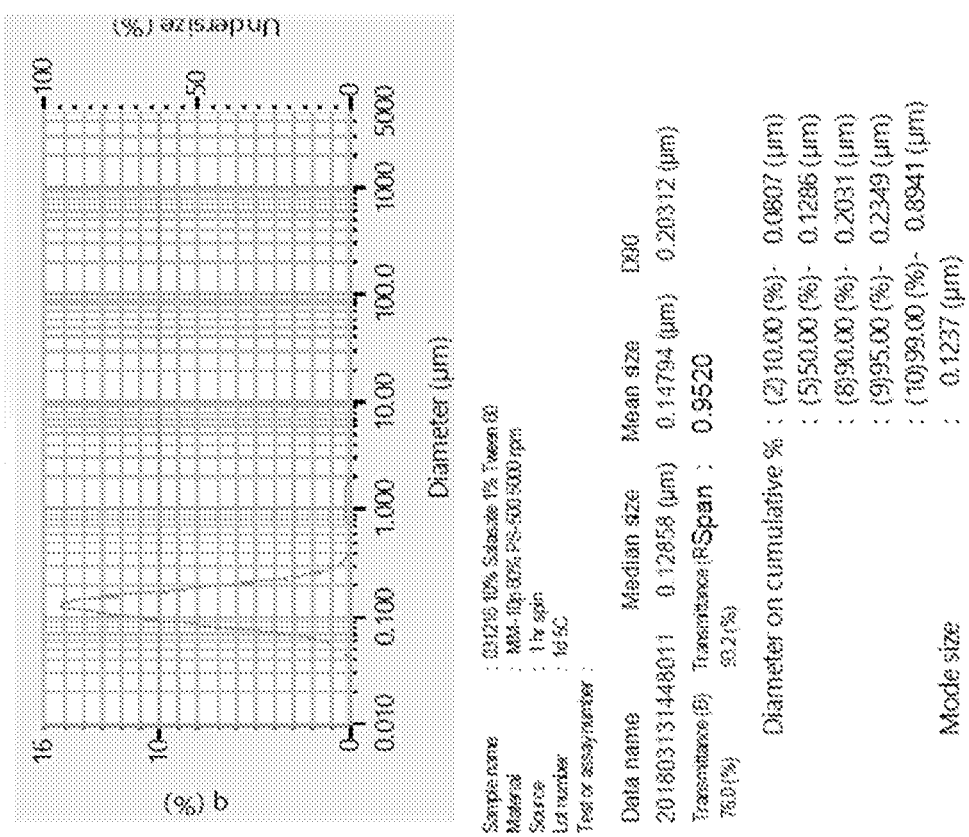
FIG. 35B shows the results of a particle size analysis.

| FIG. | Formulation | Composition | Process Conditions | Particle Sizes (μm) | Comments |
|---|---|---|---|---|---|
| 33A, B | FF | 10% salsalate, 1% Tween 80 | MM-10p High Speed Media Mill, 80% PS-500 media, 5000 rpm | Median = 0.118 Mean = 0.124 D90 = 0.179 | Larger salsalate agglomerates shown in the optical micrograph in FIG. 33A can be subsequently removed by centrifugation |
| 34A, B | GG | 10% salsalate, 1% Tween 80 | MM-10p High Speed Media Mill, 80% PS-500 media, 5000 rpm, 1 hr spin | Median = 0.114 Mean = 0.119 D90 = 0.169 | Larger salsalate particles have been removed by centrifugation, representing only approximately 5% of the API concentration |
| 35A, B | HH | 10% salsalate, 1% Tween 80 | MM-10p High Speed Media Mill, 80% PS-500 media, 5000 rpm, 1 hr spin, 1 day at 5° C. | Median = 0.129 Mean = 0.148 D90 = 0.203 | Larger salsalate particles can be seen ripening in the optical micrograph (FIG. 35A). A small tail is visible in the particle size analysis at about 1 μm in diameter (FIG. 35B). |

TABLE 5-continued

Figure 36A:
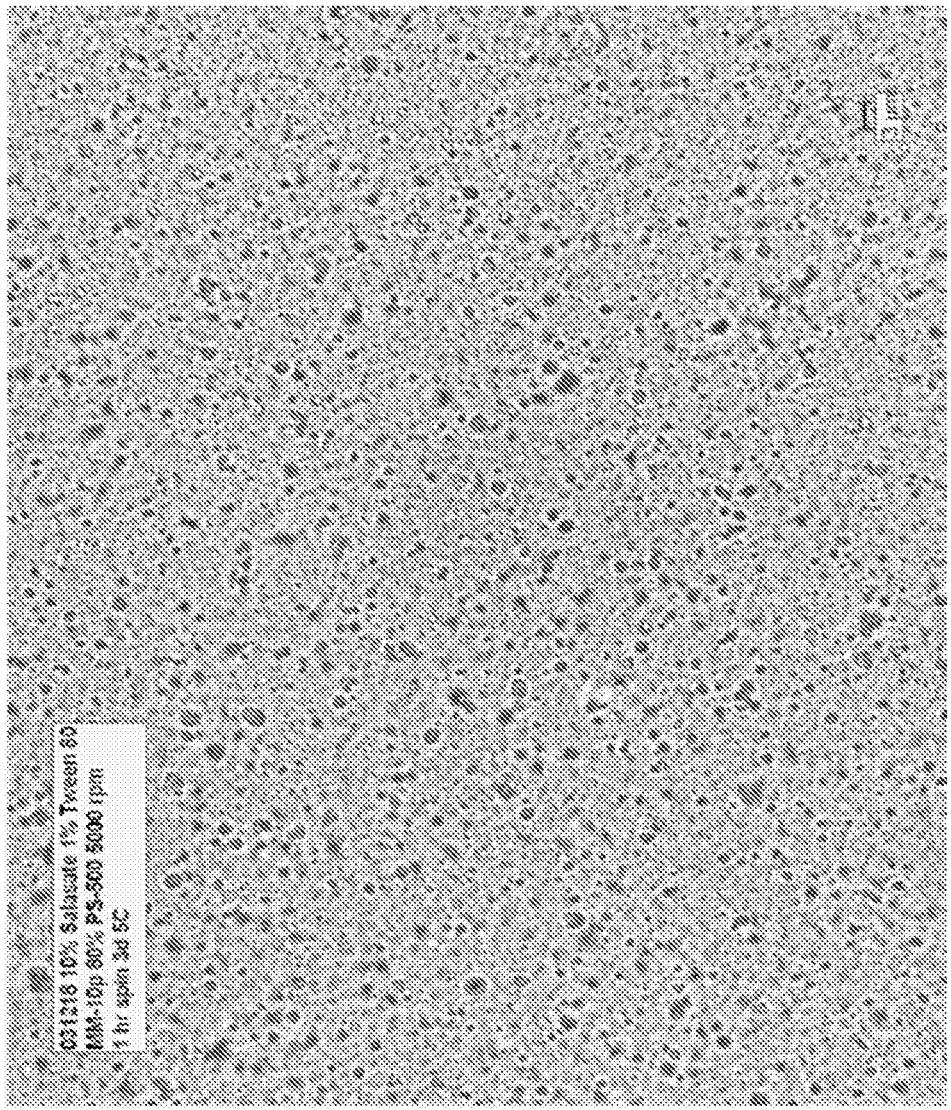
FIGS. 36A, B.
Figure 36B:
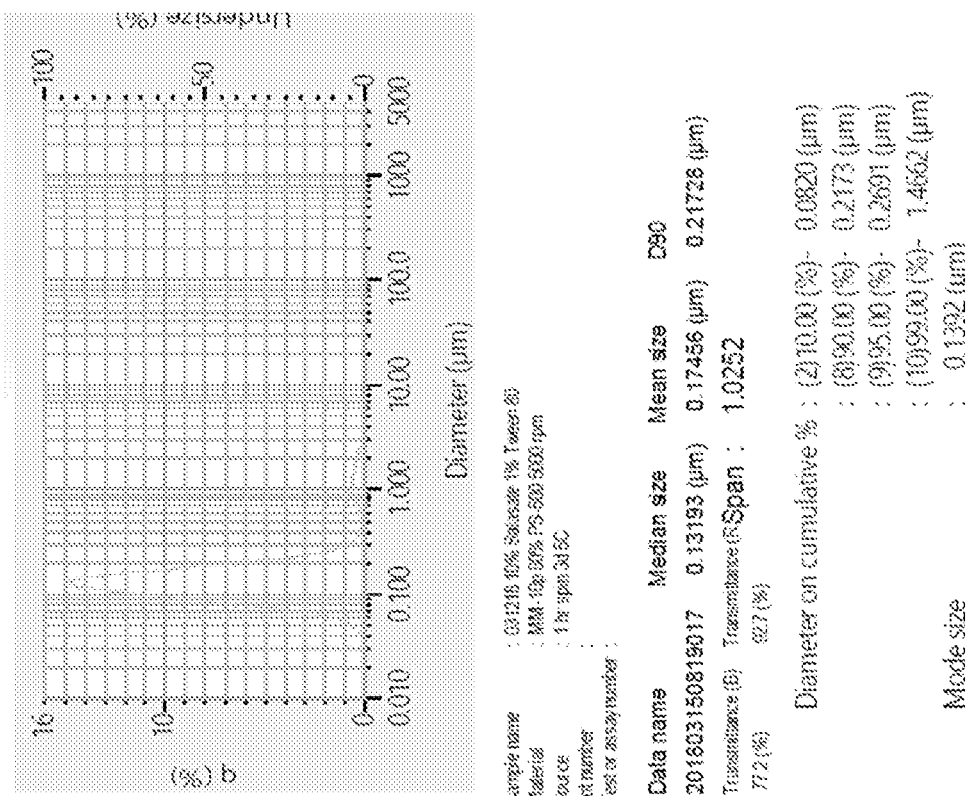
FIG. 36B shows the results of a particle size analysis.
Figure 37A:
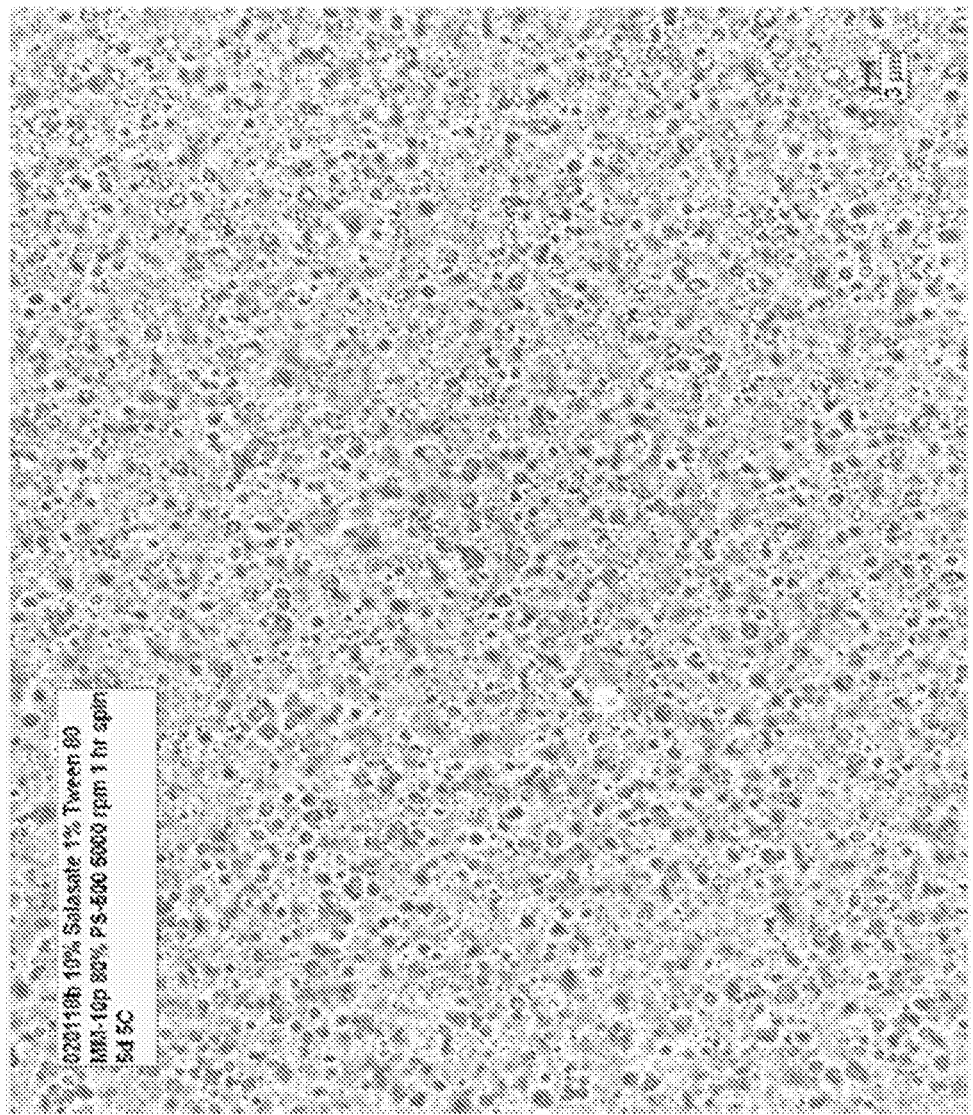
FIGS. 37A, B.
Figure 37B:
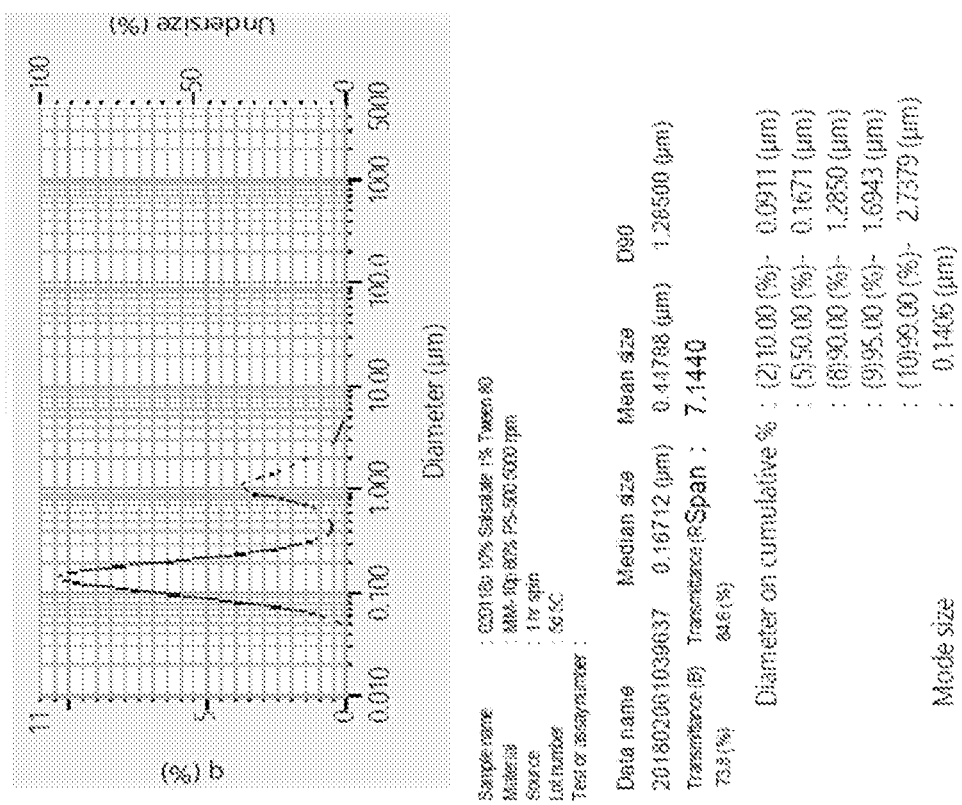
FIG. 37B shows the results of a particle size analysis.

| FIG. | Formulation | Composition | Process Conditions | Particle Sizes (μm) | Comments |
|---|---|---|---|---|---|
| 36A, B | II | 10% salsalate, 1% Tween 80 | MM-10p High Speed Media Mill, 80% PS-500 media, 5000 rpm, 1 hr spin, 3 days at 5° C. | Median = 0.132 Mean = 0.175 D90 = 0.217 | Larger salsalate particles than those in FIG. 35A can be seen ripening in the optical micrograph (FIG. 36A). A secondary peak is visible in in the particle size analysis at about 1 μm in diameter (FIG. 36B). |
| 37A, B | JJ | 10% salsalate, 1% Tween 80 | MM-10p High Speed Media Mill, 80% PS-500 media, 5000 rpm, 1 hr spin, 5 days at 5° C. | Median = 0.167 Mean = 0.448 D90 = 1.285 | Pronounced salsalate particle size growth is visible in the optical micrograph (FIG. 37A). A large secondary peak is visible in in the particle size analysis at about 1 μm in diameter (FIG. 37B). Growth is linear over time when compared to 0 days, 1 day, and 3 days at 5° C. |

The data shown in Table 5 demonstrates that high energy milling produces salsalate nanodispersions that have a low percentage of extraneous salsalate particle clusters, which can be removed by centrifugation, and therefore are successful salsalate nanodispersions. In addition, storage of formulations prepared by high speed milling at low temperatures (5° C.) results in salsalate particle size growth that is linear over time.

Example 4

This example describes impurity testing of a salsalate nanosuspension prepared for use in an animal study.

A formulation comprising salsalate and Tween 80 was prepared as described herein. The formulation was then immediately diluted and submitted for impurity analysis. Analysis was performed in duplicate and compared to freshly prepared standard solutions. The amount of individual and total impurities detected in the formulation was consistent with amounts found in the bulk API, as shown in Table 6 below.

TABLE 6

| Formulation | Target Salsalate Concentration (mg/g) | Salsalate Assay (% label claim) | Actual Salsalate Concentration (mg/g) | Salicylic Acid (% label claim) | Tri-salicyclic Acid (% label claim) | Total Impurities (% label claim) |
|---|---|---|---|---|---|---|
| Salsalate-Tween 80 | 93.9 | 101.1 | 94.9 | 0.07 | 0.18 | 0.25 |

This example describes a pharmacokinetic analysis of an in vivo administration of a salsalate nanosuspension in a human subject.

A subject was administered a single 750 mg dose of a salsalate nanosuspension. The nanosuspension was formulated for oral administration and consisted of 175 mg/g salsalate, 3.5% (w/w) Plasdone S-630, and 0.175% (w/w) dioctyl sodium sulfosuccinate ("DOSS"). The composition was prepared as described above in Example 1.

Figure 24:
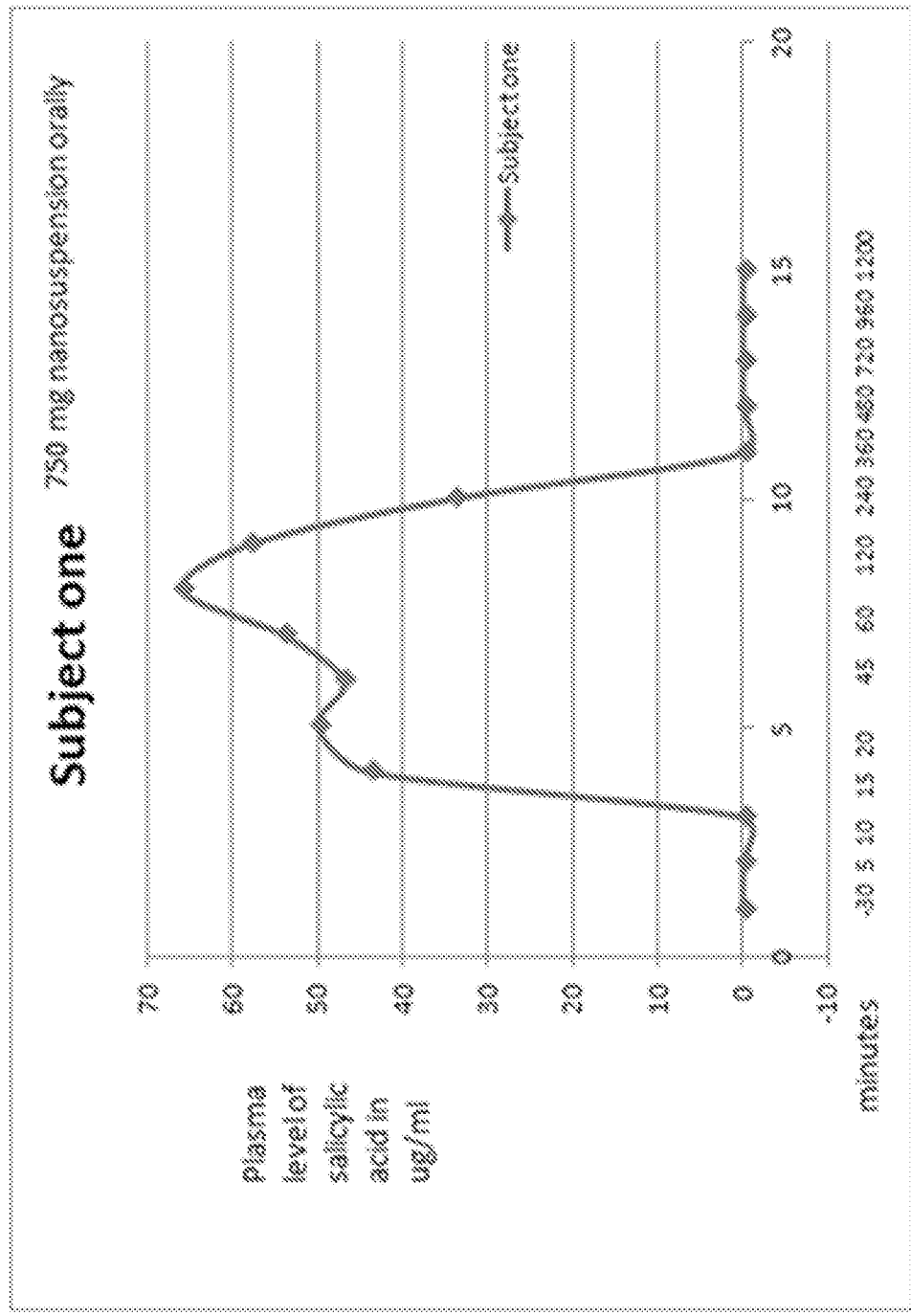
FIG. 24. Plasma level of salicyclic acid (the only known metabolie of salsalate, "SA") in a human subject ("Subject one") administered a single 750 mg dose of a salsalate nanosuspension. The nanosuspension was formulated for oral administration and consisted of 175 mg/g salsalate, 3.5% Plasdone S-630, and 0.175% dioctyl sodium sulfosuccinate ("DOSS"). The x-axis depicts the number of minutes following oral administration. The y-axis depicts the plasma level of SA in µg/mL.

As shown in FIG. 24, which shows a graph of plasma level of salicylic acid in μg/ml (y axis) vs time (x axis), the maximum salicylic acid (SA) concentration in plasma was reached between 10 and 360 minutes following administration. The data exhibits a bimodal curve with peaks in SA metabolite concentration at about 20 minutes and at about 90 minutes.

This data demonstrate that the salsalate nanodispersions of the invention are useful in in vivo applications. Plasma levels of SA remain high for a period of about 11 hours, showing usefulness for example of a 12 hour dosing period.

Example 6

This example describes a pharmacokinetic analysis of an in vivo administration of a salsalate nanosuspension in a human subject.

Two human subjects were administered a single dose of 750 mg of 4.28 ml of an oral nanosuspension of salsalate. The nanosuspension was formulated for oral administration and consisted of 175 mg/g salsalate, 3.5% (w/w) Plasdone S-630, and 0.175% (w/w) dioctyl sodium sulfosuccinate ("DOSS"). The composition was prepared as described above in Example 1.

Figure 25A:
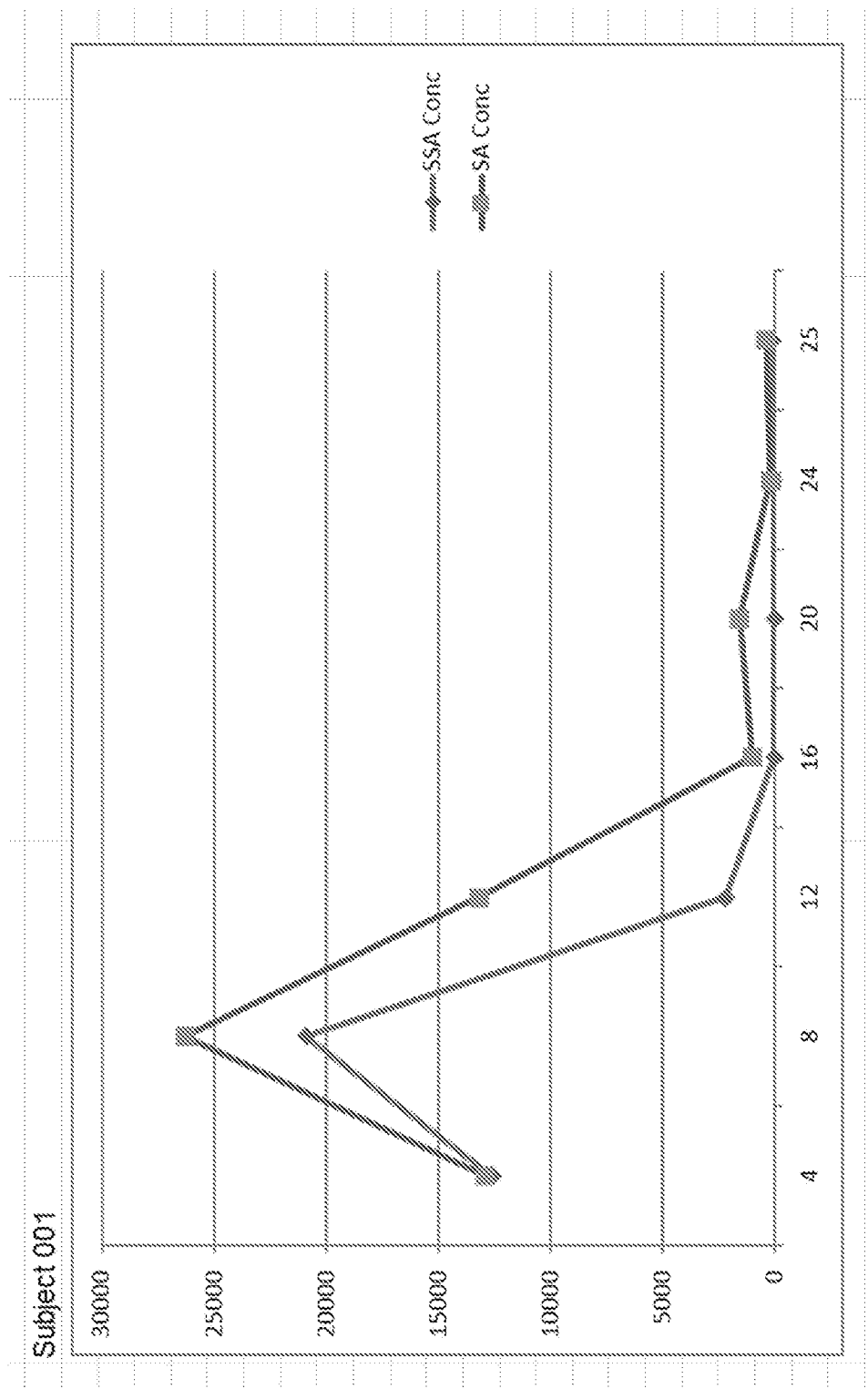
FIGS. 25A-C. Urine analyses for salsalate (parent drug, "SSA") and SA.
Figure 25B:
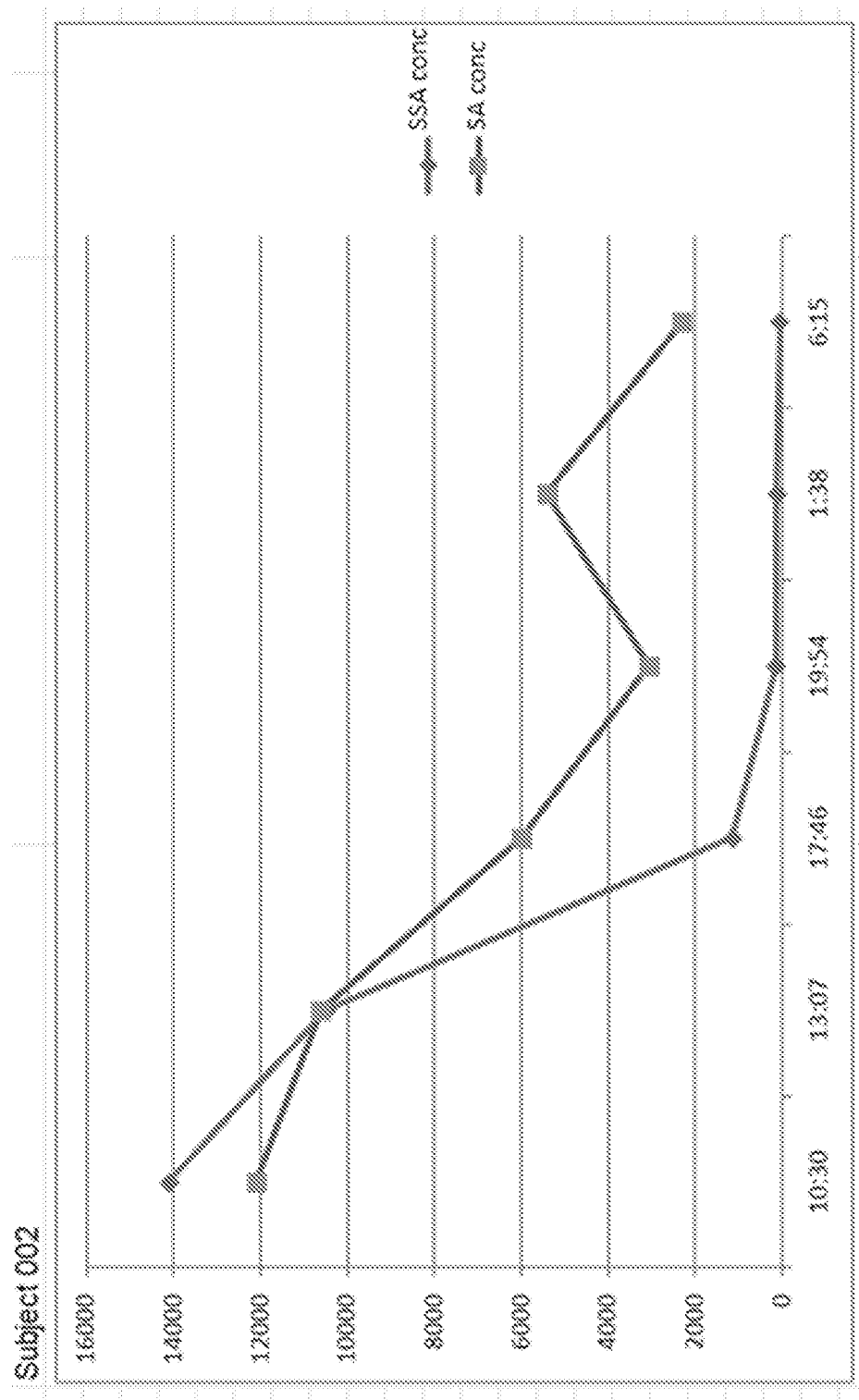
Figure 25C:
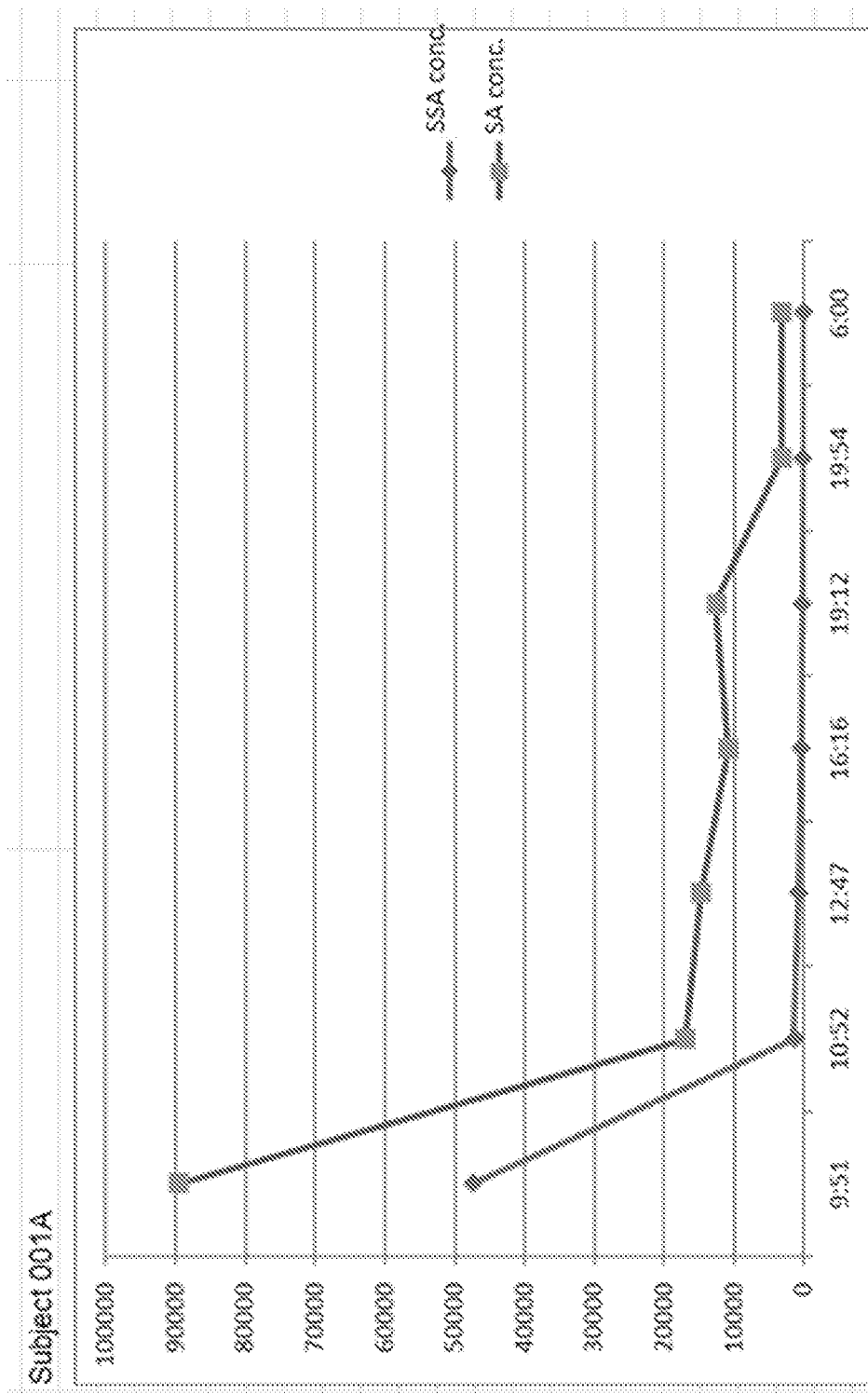

The concentration of SSA (parent drug, salsalate) and SA (only known metabolite salicylic acid) in the subjects' urine (μg/ml) vs time (hours) is shown in FIGS. 25A and 25B. For comparison, FIG. 25C depicts the urine concentration of a third human subject that was administered one tablet of microcrystalline salsalate distributed and/or manufactured by ECI Pharma (Florida, USA), also a 750 mg dose.

FIG. 25A shows that the concentration of SA and SSA peak at about 8 hours, and then steadily decline over time, with SSA and SA concentrations approaching 0 at about 16 hours. Substantial plasma levels of SA are present for 16 hours, and substantial levels of SSA are present for about 12 hours, again demonstrating the prolonged plasma levels of drug following administration. FIG. 25B shows that plasma concentrations of SSA and SA extend up to about 18 hours (SSA) and 21 hours (SA).

Finally, FIG. 25C shows that the conventional, microcrystalline formulation of salsalate does not have a peak plasma level, and that the AUC is significantly less for microcrystalline salsalate as compared to a salsalate nanosuspension given at the same dosage.

These data show that the salsalate nanosuspensions of the invention have a much longer plasma retention time as compared to microcrystalline salsalate, and suggest that lower doses of salsalate, combined with less frequent administration, can be utilized with salsalate nanosuspensions of the invention nanosuspensions as compared to microcrystalline salsalate.

Example 7

Treating Patients Diagnosed with Type II Diabetes with Once or Twice Daily Salsalate Nanosuspension in doses that result in a serum level that is kept within the following salicylic acid range of about 120-about 200 µg/ml is expected to achieve similar results as indicated by Goldfine et al., *Ann Intern Med.*, 152(6): 346-357 (2010).

FIGS. 28A-F summarizes various oral doses of twice daily non-nano (regular/standard formulation microcrystalline) salsalate at three different daily doses of 3.0, 3.5 and 4.0 grams over a 4 week period in patients with type two diabetes mellitus. Id. In contrast, it is expected that a lower dose of either once or twice daily salsalate nanosuspension will be required to achieve the same therapeutic serum level of salicylic acid. In particular, FIG. 26 demonstrates how rapidly the serum salsalate and serum salicylic acid levels rise after taking of a single dose of 750 mg nanosalsalate suspension vs a standard 750 mg oral tablet of microcrystalline salsalate.

In particular, data shown in FIG. 28 shows changes in circulating metabolic measures, by study group. All data are provided as unadjusted mean changes. Each data point represents the mean value for all patients examined. 27 patients were analyzed at baseline in each group. This decreased to 26 patients in the 4.0-g/d group at 4 weeks; 26 and 25 patients in the 3.5- and 4.0-g/d groups, respectively, at 8 weeks; and 26 patients in the placebo and 3.5-g/d groups and 25 in the 4.0-g/d group at 14 weeks (FIG. 28). FBG=fasting blood glucose; HbA1c=hemoglobin A1c; HDL=high-density lipoprotein. FIG. 28A=Trends in HbA1c level over time. The F test for the overall effect of treatment group was significant (P=0.003) as was each pairwise test between placebo and salsalate. FIG. 28B=Trends in FBG concentration over time. To convert results from mg/dL to mmol/L, multiply by 0.0555. FIG. 28C=Trends in glycated albumin level over time. FIG. 28D=Trends in adiponectin concentration over time. FIG. 28E=triglyceride concentration over time. FIG. 28F=total HDL-cholesterol ratio over time.

Thus, it is expected that a lower dose of either once or twice daily salsalate nanosuspension will be required to achieve the same therapeutic serum level of salicylic acid as compared to microcrystalline salsalate. In an exemplary embodiment, adult patients diagnosed with Type II Diabetes can be administered an oral salsalate nanosuspension once or twice daily including 3000 to 4500 mg to achieve serum salicylate levels of between about 120 to about 200 µg/mL of salicylic acid for 12 weeks, with outcome measure fasting and postprandial blood sugars as well as HbA1c levels at 12 weeks.

Example 8

Treating Patients Diagnosed with Traumatic TBI with Once or Twice Daily Salsalate Nanosuspension.

Patients diagnosed with TBI or at risk for TBI are administered an oral nanosalsalate suspension formulation once or twice daily including about 2000 to about 4000 mg to achieve a serum level of about 120 to about 200 µg/mL over a six month period with neuropsychological outcomes as a primary efficacy measurement.

Example 9

This example describes treatment of a subject diagnosed with dry eye syndrome with a salsalate nanosuspension.

A subject diagnosed with dry eye syndrome is administered a topical nanosalsalate suspension formulation every six to 12 hours, or once daily. The topical nanosalsalate suspension formulation is an eye drop, ointment, or gel that comprises salsalate at about 0.01% to about 0.1%, about 0.1% to about 1%, or about 1% to about 5%, or about 1% to about 10%.

Success of the treatment is determined by detecting an improvement or amelioration of one or more symptoms associated with dry eye syndrome in the subject, and/or detecting an increase in the subject's tear formation.

Example 10

This example describes treatment of a subject diagnosed with osteoarthritis with a salsalate nanosuspension.

A subject diagnosed with osteoarthritis is administered a nanosalsalate suspension once or twice daily at about 1000 mg to about 4500 mg to achieve a serum plasma concentration of salsalate ranging from about 120 to about 200 µg/ml over a period of at least about 12 to about 24 hours. The salsalate nanosuspension is formulated for oral administration as a tablet and can comprise, for example, 175 mg/g salsalate, 3.5% (w/w) Plasdone S-630, and 0.175% (w/w) DOSS. Other exemplary salsalate nanodispersions are described herein. The composition is prepared as described above in Example 1. The treatment duration lasts for several weeks or as needed until improvement in the subject's condition is detected.

Success of the treatment is determined by detecting one or more of: (1) delay in the progression of osteoarthritis, (2) improvement or amelioration of one or more symptoms associated with osteoarthritis such as decreased pain and improved mobility, (3) decreased thickness of articular cartilage or the synovial membrane, and/or (4) decreased or maintained density of subchondral bone in the subject.

Example 11

This example describes treatment of a subject diagnosed with hemophilia with a salsalate nanosuspension.

A subject diagnosed with hemophilia is administered a nanosalsalate suspension once or twice daily at about 1000 mg to about 4500 mg to achieve serum plasma concentration of salsalate ranging from about 120 to about 200 µg/ml over a period of at least about 12 to about 24 hours. The nanosuspension is formulated for oral administration as a tablet and comprises, for example, 175 mg/g salsalate, 3.5% (w/w) Plasdone S-630, and 0.175% (w/w) DOSS. Other exemplary salsalate nanodispersions are described herein. The composition is prepared as described above in Example 1. The treatment duration lasts for several weeks or as needed until improvement in the subject's condition is detected.

Success of treatment is determined by a reduction in the amount or degree of pain experienced by the subject, detecting decreased inflammation in the subject, and/or detecting a reduction or amelioration of one or more symptoms associated with hemophilia in the subject.

Example 12

This example describes treatment of a subject diagnosed with coronary artery disease with a salsalate nanosuspension.

A subject diagnosed with coronary artery disease is administered a nanosalsalate suspension once or twice daily of about 1000 mg to about 4500 mg to achieve serum plasma concentration of salsalate ranging from about 120 to about 200 µg/ml over a period of at least about 12 to about 24 hours. The nanosuspension is formulated for oral administration as a tablet and comprises, for example, 175 mg/g salsalate, 3.5% (w/w) Plasdone S-630, and 0.175% (w/w) DOSS. Other exemplary salsalate nanosdispersions are described herein. The composition is prepared as described above in Example 1. The treatment duration lasts for several weeks or as needed until improvement in the subject's condition is detected.

Success of treatment can be determined by a reduction in the amount or degree of pain experienced by the subject, detecting decreased inflammation in the subject, and/or detecting a reduction or amelioration of one or more symptoms associated with CAD in the subject.

Example 13

This example describes treatment of a subject with chronic pain with a salsalate nanosuspension.

A subject diagnosed with chronic pain is administered a salsalate nanosuspension once or twice daily at about 1000 mg to about 4500 mg to achieve serum plasma concentration of salsalate ranging from about 120 to about 200 µg/ml over a period of at least about 12 to about 24 hours. The nanosuspension is formulated for oral administration as a tablet and comprises, for example, 175 mg/g salsalate, 3.5% (w/w) Plasdone S-630, and 0.175% (w/w) DOSS. Other exemplary salsalate nanosdispersions are described herein. The composition is prepared as described above in Example 1. The treatment duration lasts until the pain is improved or resolved.

Success of treatment can be determined by resolution of the subject's pain or by detecting a reduction in the amount, degree, or frequency of pain experienced by the subject. In some embodiments, pain reduction is identified by an improvement in the subject's VAS score, IASP classification, and/or MPI identification.

It will be apparent to those skilled in the art that various modifications and variations can be made in the methods and compositions of the present disclosure without departing from the spirit or scope of the invention. Thus, it is intended that the present disclosure cover the modifications and variations of this invention provided they come within the scope of the appended claims and their equivalents.

REFERENCES

Anderson et al., American Health & Drug Benefits, 7 (4): 231-235 (2014).
Harrison et al., J. Clin. Pharmacol., 21: 401-404 (1981).
Harrison et al., Therapeutic Drug Monitoring, 14: 87-91 (1992).
Lagraouri et al., Brain, Behavior, and Immunity, 61: 96-109 (2017).
Maude et al., "Managing Cytokine Release Syndrome Associated with Novel T Cell-Engaging Therapies," Cancer J., 20(2): 1-9 (2014).
Lee Daniel W, et al., "Current Concepts in the diagnosis and management of cytokine release syndrome," Blood, 128 (11): 1533 (Sep. 15, 2006).

What is claimed is:

1. A salsalate nanosuspension comprising:
   (a) an aqueous dispersion of salsalate or a salt thereof, wherein the salsalate comprises salsalate particles having an effective average particle size of less than 1 micron;
   (b) at least two surfactants; and
   (c) citric acid,
   wherein the at least two surfactants are polysorbate 80 and Carbowax® polyethylene glycol 3350.

2. The salsalate nanosuspension of claim 1, wherein the salsalate has an effective average particle size selected from the group consisting of about 900 nm, less than 900 nm, less than 800 nm, less than 700 nm, less than 600 nm, less than 500 nm, less than 400 nm, less than 300 nm, less than 275 nm, less than 250 nm, less than 225 nm, less than 200 nm, less than 175 nm, less than 150 nm, less than 125 nm, less than 100 nm, less than 75 nm, and less than 50 nm.

3. The salsalate nanosuspension of claim 1, wherein:
   (a) the nanosuspension is formulated for administration selected from the group consisting of oral, pulmonary, rectal, opthalmic, colonic, parenteral, intravenous, intracisternal, intravaginal, intraperitoneal, local, buccal, nasal, and topical administration; or
   (b) the nanosuspension is formulated for oral administration; or
   (c) the nanosuspension is formulated for intravenous administration; or
   (d) the nanosuspension is formulated for topical administration to the eye of the subject; or
   (e) the nanosuspension is formulated into a dosage form selected from the group consisting of liquid dispersions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

4. The salsalate nanosuspension of claim 1, wherein the nanosuspension further comprises one or more pharmaceutically acceptable excipients, carriers, or a combination thereof.

5. The salsalate nanosuspension of claim 1, wherein:
   (a) salsalate is present in an amount selected from the group consisting of from about 99.5% to about 0.001%, from about 95% to about 0.1%, and from about 90% to about 0.5%, by weight, based on the total combined weight of salsalate and at least two surfactants, not including other excipients; and
   (b) the at least two surfactants are present in an amount selected from the group consisting of from about 0.5% to about 99.999%, from about 5.0% to about 99.9%, and from about 10% to about 99.5%, by weight, based on the total combined weight of salsalate and at least two surfactants, not including other excipients.

6. The salsalate nanosuspension of claim 1, further comprising at least one non-salsalate active agent.

7. The salsalate nanosuspension of claim 1, wherein upon administration:
- (a) the $T_{max}$ of the salsalate nanosuspension is less than that of a conventional non-nanosuspension or microcrystalline composition of salsalate, administered at the same dosage;
- (b) the $C_{max}$ of the salsalate nanosuspension is greater than that of a conventional non-nanosuspension or microcrystalline composition of salsalate, administered at the same dosage; and/or
- (c) the AUC of the salsalate nanosuspension is greater than that of a conventional non-nanosuspension or microcrystalline composition of salsalate, administered at the same dosage.

8. The salsalate nanosuspension of claim 1, wherein in comparative pharmacokinetic testing with a conventional non-nanosuspension or microcrystalline composition of salsalate, administered at the same dosage, the salsalate nanosuspension exhibits:
- (a) a $T_{max}$ selected from the group consisting of about 100%, less than 100%, less than 90%, less than 80%, less than 70%, less than 60%, less than 50%, less than 40%, less than 30%, less than 25%, less than 20%, less than 15%, and less than 10% of the $T_{max}$ exhibited by the conventional non-nanosuspension or microcrystalline composition of salsalate;
- (b) a $C_{max}$ selected from the group consisting of about 5%, greater than 5%, greater than 10%, greater than 15%, greater than 20%, greater than 30%, greater than 40%, greater than 50%, greater than 60%, greater than 70%, greater than 80%, greater than 90%, greater than 100%, greater than 110%, greater than 120%, greater than 130%, greater than 140%, and greater than 150% than the $C_{max}$ exhibited by the conventional non-nanosuspension or microcrystalline composition of salsalate; and/or
- (c) an AUC selected from the group consisting of about 5%, greater than 5%, greater than 10%, greater than 15%, greater than 20%, greater than 30%, greater than 40%, greater than 50%, greater than 60%, greater than 70%, greater than 80%, greater than 90%, greater than 100%, greater than 110%, greater than 120%, greater than 130%, greater than 140%, and greater than 150% than the AUC exhibited by the conventional non-nanosuspension or microcrystalline composition of salsalate.

9. The salsalate nanosuspension of claim 1, wherein following administration:
- (a) the nanosuspension has a $T_{max}$ selected from the group consisting of about 10 hours, less than 10 hours, less than 9 hours, less than 8 hours, less than 7 hours, less than 6 hours, less than 5.5 hours, less than 5 hours, less than 4.5 hours, less than 4 hours, less than 3.5 hours, less than 3 hours, less than 2.5 hours, less than 2.25 hours, less than 2 hours, less than 1.75 hours, less than 1.5 hours, less than 1.25 hours, less than 1.0 hours, less than 50 minutes, less than 40 minutes, less than 30 minutes, less than 25 minutes, less than 20 minutes, less than 15 minutes, and less than 10 minutes; and/or
- (b) the nanosuspension has a $T_{max}$ between 10 minutes to 10 hours.

10. A method of making a salsalate nanosuspension according to claim 1, comprising contacting particles of salsalate with at least two surfactants for a time and under conditions sufficient to provide a salsalate nanosuspension, wherein the resultant salsalate has an effective average particle size of less than 1 micron, and wherein optionally the contacting comprises grinding or homogenization.

11. A method of treating pain in a subject, the method comprising administering to the subject a therapeutically effective amount of the salsalate nanosuspension, wherein the salsalate nanosuspension comprises:
- (a) an aqueous dispersion of salsalate or a salt thereof, wherein the salsalate has an effective average particle size of less than 1 micron;
- (b) at least two surfactants, wherein the at least two surfactants polysorbate 80 and Carbowax® polyethylene glycol 3350; and
- (c) citric acid.

12. The method of claim 11 comprising:
- (a) oral, parenteral, or intravenous administration; and/or
- (b) once or twice daily administration.

13. The method of claim 11, wherein:
- (a) the salsalate nanosuspension comprises about 1000 mg to about 2000 mg of nanosalsalate suspension administered orally or parenterally; and/or
- (b) following administration the salsalate nanosuspension maintains a plasma concentration of salsalate ranging from about 120 to about 200 µg/ml over a period of at least about 12 to about 24 hours.

14. The method of claim 11, wherein the subject is a mammal.

15. The method of claim 14, wherein the mammal is a human.

16. The salsalate nanosuspension of claim 1, wherein the nanosuspension further comprises mannitol.

17. A salsalate nanosuspension comprising:
- (a) an aqueous dispersion of salsalate or a salt thereof, wherein the salsalate comprises salsalate particles having an effective average particle size of less than 1 micron;
- (b) at least two surfactants; and
- (c) citric acid,
wherein the at least two surfactants comprise (i) Plasdone S-630 and dioctyl sodium sulfosuccinate (DOSS); or (ii) polysorbate 80 and Carbowax® polyethylene glycol 3350.

18. The salsalate nanosuspension of claim 17, wherein the at least two surfactants comprise Plasdone S-630 and DOSS.

* * * * *